(12) United States Patent
Haydon et al.

(10) Patent No.: US 8,299,065 B2
(45) Date of Patent: Oct. 30, 2012

(54) ANTIBACTERIAL CONDENSED THIAZOLES

(75) Inventors: David John Haydon, Oxfordshire (GB); Lloyd George Czaplewski, Oxfordshire (GB)

(73) Assignee: Biota Europe Ltd., Oxfordshire (GB)

( * ) Notice: Subject to any disclaimer, the term of this patent is extended or adjusted under 35 U.S.C. 154(b) by 25 days.

(21) Appl. No.: 12/747,811

(22) PCT Filed: Dec. 12, 2008

(86) PCT No.: PCT/GB2008/004114
§ 371 (c)(1),
(2), (4) Date: Jul. 14, 2010

(87) PCT Pub. No.: WO2009/074812
PCT Pub. Date: Jun. 18, 2009

(65) Prior Publication Data
US 2010/0305067 A1    Dec. 2, 2010

(30) Foreign Application Priority Data
Dec. 13, 2007   (GB) .................................. 0724342.1

(51) Int. Cl.
| | | |
|---|---|---|
| A61K 31/5365 | (2006.01) |
| A61K 31/4427 | (2006.01) |
| A61K 31/4196 | (2006.01) |
| A61K 31/497 | (2006.01) |
| A61K 31/428 | (2006.01) |
| A61K 31/47 | (2006.01) |
| A61K 31/5377 | (2006.01) |
| A61K 31/506 | (2006.01) |
| C07D 417/14 | (2006.01) |
| C07D 417/02 | (2006.01) |
| C07D 265/28 | (2006.01) |
| C07D 241/10 | (2006.01) |
| C07D 277/62 | (2006.01) |
| C07D 401/14 | (2006.01) |
| C07D 265/30 | (2006.01) |
| C07D 241/04 | (2006.01) |
| C07D 239/20 | (2006.01) |

(52) U.S. Cl. ................. 514/230.5; 514/255.05; 514/338; 514/382; 514/367; 514/307; 514/235.5; 514/333; 514/252.13; 514/269; 544/242; 544/358; 544/124; 544/336; 544/105; 546/270.1; 546/272.4; 546/268.4; 546/139; 546/256; 548/152

(58) Field of Classification Search ............... 514/230.5, 514/235.5, 252.13, 255.05, 269, 307, 333, 514/338, 367, 382; 544/105, 124, 242, 336, 544/358; 546/139, 256, 268.4, 270.1, 272.4; 548/152

See application file for complete search history.

(56) References Cited

U.S. PATENT DOCUMENTS
| | | | |
|---|---|---|---|
| 3,725,428 A | 4/1973 | Janiak | |
| 4,028,374 A | 6/1977 | Pelosi, Jr. et al. | |
| 2011/0306615 A1* | 12/2011 | Tachibana et al. | ......... 514/235.8 |

FOREIGN PATENT DOCUMENTS
| | | |
|---|---|---|
| EP | 1 790 640 A | 5/2007 |
| NL | 6916457 A | 5/1970 |
| WO | 01/57008 A | 8/2001 |
| WO | 01/97786 A | 12/2001 |
| WO | 02/060879 A | 8/2002 |
| WO | 2005/012292 A | 2/2005 |
| WO | 2005/037845 A1 | 4/2005 |
| WO | 2006/028226 A | 3/2006 |
| WO | 2007148093 A | 12/2007 |

OTHER PUBLICATIONS

International Search Report for PCT/GB2008/004114, Issued Feb. 24, 2009.
Office Action for corresponding U.S. Appl. No. 13/154,592 mailed Feb. 14, 2012.
Snyder et al., J. Med. Liban 48(4): 208-214, 2000.

* cited by examiner

*Primary Examiner* — Joseph K. McKane
*Assistant Examiner* — Samantha Shterengarts
(74) *Attorney, Agent, or Firm* — Banner & Witcoff, Ltd.

(57) ABSTRACT

Compound of formula (I) have antibacterial activity: wherein: m is 0 or 1; Q is hydrogen or cyclopropyl; Alk is an optionally substituted, divalent $C_1$-$C_6$ alkylene, alkenylene or alkynylene radical which may contain an ether (—O—), thioether (—S—) or amino (—NR)— link, wherein R is hydrogen, —CN or $C_1$-$C_3$ alkyl; X is —C(=O)$NR_6$—, or —C(=O)O— wherein $R_6$ is hydrogen, optionally substituted $C_1$-$C_6$ alkyl, $C_2$-$C_6$ alkenyl or $C_2$-$C_6$ alkynyl; $Z_1$ is —N= or —CH=; $Z_2$ is —N= or —C($R_1$)=; $R_1$ is hydrogen, methyl, ethyl, ethenyl, ethynyl, methoxy, mercapto, mercaptomethyl, halo, fully or partially fluorinated ($C_1$-$C_2$)alkyl, ($C_1$-$C_2$)alkoxy or ($C_1$-$C_2$)alkylthio, nitro, or nitrile (—CN); $R_2$ is a group $Q^1$-[$Alk^1$]q-$Q^2$-, wherein q is 0 or 1; Alk1 is an optionally substituted, divalent, straight chain or branched $C_1$-$C_6$ alkylene, or $C_2$-$C_6$ alkenylene or $C_2$-$C_6$ alkynylene radical which may contain or terminate in an ether (—O—), thioether (—S—) or amino (—NR)— link; $Q^2$ is an optionally substituted divalent monocyclic carbocyclic or heterocyclic radical having 5 or 6 ring atoms or an optionally substituted divalent bicyclic carbocyclic or heterocyclic radical having 9 or 10 ring atoms; $Q^1$ is hydrogen, an optional substituent, or an optionally substituted carbocyclic or heterocyclic radical having 3-7 ring atoms.

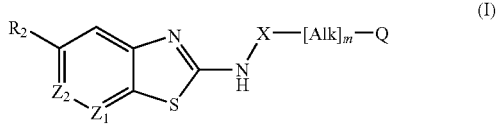

23 Claims, No Drawings

ANTIBACTERIAL CONDENSED THIAZOLES

CROSS REFERENCE TO RELATED APPLICATIONS

This application is a National Stage application of co-pending PCT application PCT/GB2008/004114 filed Dec. 12, 2008, which claims priority from Great Britain application 0724342.1 filed Dec. 13, 2007, which applications are incorporated herein by reference in their entirety.

This invention relates to substituted benzothiazoles, thiazolopyridines and thiazolopyridazines that are useful as antibacterial agents.

BACKGROUND TO THE INVENTION

Type II topoisomerases catalyse the interconversion of DNA topoisomers by transporting one DNA segment through another. Bacteria encode two type II topoisomerase enzymes, DNA gyrase and DNA topoisomerase IV. Gyrase controls DNA supercoiling and relieves topological stress. Topoisomerase IV decatenates daughter chromosomes following replication and can also relax supercoiled DNA. Bacterial type II topoisomerases form a heterotetrameric complex composed of two subunits. Gyrase forms an $A_2B_2$ complex comprised of GyrA and GyrB whereas topoisomerase forms a $C_2E_2$ complex comprised of ParC and ParE. In contrast eukaryotic type II topoisomerases are homodimers. Ideally, an antibiotic based on the inhibition of bacterial type II topoisomerases would be selective for the bacterial enzymes and be relatively inactive against the eukaryotic type II isomerases. The type II topoisomerases are highly conserved enzymes allowing the design of broad-spectrum inhibitors. Furthermore, the GyrB and ParE subunits are functionally similar, having an ATPase domain in the N-terminal domain and a C-terminal domain that interacts with the other subunit (GyrA and ParC respectively) and the DNA. The conservation between the gyrase and topoisomerase IV active sites suggests that inhibitors of the sites might simultaneously target both type II topoisomerases. Such dual-targeting inhibitors are attractive because they have the potential to reduce the development of target-based resistance.

Type II topoisomerases are the target of a number of antibacterial agents. The most prominent of these agents are the quinolones. The original quinolone antibiotics included nalidixic acid, cinoxacin and oxolinic acid. The addition of fluorine yielded a new class of drugs, the fluoroquinolones, which have a broader antimicrobial spectrum and improved pharmacokinetic properties. The fluoroquinolones include norfloxacin, ciprofloxacin, and fourth generation quinolones gatifloxacin and moxifloxacin. The coumarins and the cyclothialidines are further classes of antibiotics that inhibit type H topoisomerases, however they are not widely used because of poor permeability in bacteria, eukaryotic toxicity, and low water solubility. Examples of such antibiotics include novobiocin and coumermycin A1, cyclothialidine; cinodine, and clerocidin. However, the continuous emergence of antibiotic resistance demands that novel classes of antibiotics continue to be developed and alternative compounds that inhibit bacterial topoisomerases are required.

BRIEF SUMMARY OF THE CONTEXT OF THE INVENTION

This invention is based on the finding that a class of substituted benzothiazoles, thiazolopyridines and thiazolopyridazines has antibacterial activity, as evidenced by inhibition of bacterial growth by members of that class. The compounds exhibit activity against strains of Gram-positive and/or Gram-negative classes, such as staphylococci, enterococci, streptococci, propionibacteria and moraxellas for example *Staphylococcus aureus, Staphylococcus epidermidis, Enterococcus faecalis, Enterococcus faecium, Streptococcus pneumoniae, Streptococcus pyogenes, Propionibacterium acnes, Haemophilus influenzae* and *Moraxella catarrhalis*. The compounds with which the invention is concerned are therefore useful for the treatment of bacterial infection or contamination, for example in the treatment of, inter alia, Gram-positive infections, community acquired pneumonias, acne vulgaris, impetigo and infected atopic dermatitis.

Whilst the invention is not limited by any particular hypothesis as to the mechanism of action of the compounds, it is presently believed that such activity is due, at least in part, to the compounds inhibiting the type II bacterial topoisomerases.

The invention therefore encompasses the antibacterial use of the class of substituted benzothiazole, thiazolopyridine and thiazolopyridazines compounds defined herein, and to novel members of that class of compounds.

International Patent Applications WO 03/105846 and WO 2005/012292 relate to benzimidazole, and pyridoimidazole compounds which inhibit bacterial gyrase activity. Many benzimidazoles and a single 1H-imidazo[4,5-b]pyridine were synthesized, characterized and tested for gyrase and antibacterial activity. Although they were claimed, no 3H-imidazo[4,5-c]pyridine was synthesized. Therefore, no "proof of principle" that 3H-imidazo[4,5-c]pyridines have the asserted gyrase inhibitory and antibacterial activities was provided.

Co-pending patent application PCT/GB2007/002314 describes substituted benzothiazole and thiazolopyridine compounds that inhibit bacterial gyrase activity. The benzothiazoles and thiazolopyridines of that application have a substituent in the 7-position, and antibacterial activity is demonstrated for those 7-substituted compounds.

International Patent Application No. WO 2001057008 relates to benzothiazoles said to be useful for treatment of cancer and conditions in which angiogenesis is a contributory mechanism. That document does not state or imply that the compounds with which it is concerned have antibacterial activity, nor does it disclose the substituted benzothiazole, thiazolopyridine and thiazolopyridazine compounds claimed herein.

DESCRIPTION OF THE INVENTION

According to the invention, there is provided a compound of formula (I) or a salt or N-oxide thereof, in the preparation of an antibacterial composition:

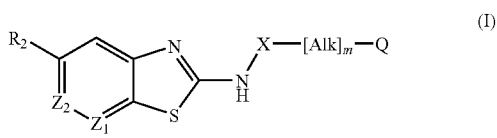

wherein:
m is 0 or 1;
Q is hydrogen or cyclopropyl;
Alk is an optionally substituted, divalent $C_1$-$C_6$ alkylene, alkenylene or alkynylene radical which may contain an ether (—O—), thioether (—S—) or amino (—NR)— link, wherein R is hydrogen, —CN or $C_1$-$C_3$ alkyl;

X is —C(=O)$NR_6$—, or —C(=O)O— wherein $R_6$ is hydrogen, optionally substituted $C_1$-$C_6$ alkyl, $C_2$-$C_6$ alkenyl or $C_2$-$C_6$ alkynyl;

$Z_1$ is —N= or —CH=

$Z_2$ is —N= or —C($R_1$)=;

$R_1$ is hydrogen, methyl, ethyl, ethenyl, ethynyl, methoxy, mercapto, mercaptomethyl, halo (including fluoro, bromo and chloro), fully or partially fluorinated ($C_1$-$C_2$)alkyl, ($C_1$-$C_2$)alkoxy or ($C_1$-$C_2$)alkylthio such as trifluoromethyl, trifluoromethoxy, and trifluoromethylthio, nitro, or nitrile (—CN);

$R_2$ is a group $Q^1$-[$Alk^1$]$_q$-$Q^2$-, wherein q is 0 or 1;

$Alk^1$ is an optionally substituted, divalent, straight chain or branched $C_1$-$C_6$ alkylene, or $C_2$-$C_6$ alkenylene or $C_2$-$C_6$ alkynylene radical which may contain or terminate in an ether (—O—), thioether (—S—) or amino (—NR—) link;

$Q^2$ is an optionally substituted divalent monocyclic carbocyclic or heterocyclic radical having 5 or 6 ring atoms or an optionally substituted divalent bicyclic carbocyclic or heterocyclic radical having 9 or 10 ring atoms;

$Q^1$ is hydrogen, an optional substituent, or an optionally substituted carbocyclic or heterocyclic radical having 3-7 ring atoms;

In other broad aspects, the invention includes:

(i) the use of a compound (I) as defined above in the preparation of an antibacterial composition;

(ii) a method of treatment of a subject suffering a bacterial infection, or preventing bacterial infection in a subject, comprising administering to the subject an amount of a compound (I) as defined above, sufficient to inhibit bacterial growth;

(iii) a method treating or preventing bacterial contamination of a substrate comprising applying to the site of such contamination or potential contamination an amount of a compound (I) as defined above, sufficient to inhibit bacterial growth;

(iv) a compound (I) as defined above for use in a method of treatment of the human body;

(v) a compound (I) as defined above for use in treating or preventing bacterial infection.

Terminology

As used herein, the term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent ($C_a$-$C_b$)alkylene radical" wherein a and b are integers refers to a saturated hydrocarbon chain having from a to b carbon atoms and two unsatisfied valences. The term includes, for example, methylene, ethylene, n-propylene and n-butylene.

As used herein the term "($C_a$-$C_b$)alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent ($C_a$-$C_b$)alkenylene radical" means a hydrocarbon chain having from a to b carbon atoms, at least one double bond, and two unsatisfied valences. The term includes, for example, —CH=CH— (vinylene), —CH=CH—$CH_2$—, —$CH_2$—CH=CH—, —CH=CH—$CH_2$—$CH_2$—, $CH_2$—CH=CH—$CH_2$—$CH_2$—, —CH=CH—CH=CH—, —CH=CH—CH=CH—$CH_2$—, —CH=CH—$CH_2$—, —CH=CH—CH=CH—$CH_2$—$CH_2$—, —CH=CH—$CH_2$—CH=CH—, and —CH=CH—$CH_2$—$CH_2$—CH=CH—.

As used herein the term "$C_a$-$C_b$ alkynyl" wherein a and b are integers refers to straight chain or branched chain hydrocarbon groups having from a to b carbon atoms and having in addition at least one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent ($C_a$-$C_b$)alkynylene radical" wherein a and b are integers refers to a divalent hydrocarbon chain having from a to b carbon atoms, and at least one triple bond. The term includes, for example, —C≡C—, —C≡C—$CH_2$—, and —$CH_2$—C≡CH—.

As used herein the term "carbocyclic" refers to a mono-, bi- or tricyclic radical having up to 16 ring atoms, all of which are carbon, and includes aryl and cycloalkyl.

As used herein the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl. cyclooctyl and bicyclo [2.2.1]hept-1-yl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and naphthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzothienyl, furyl, benzfuryl, pyrrolyl, imidazolyl, benzimidazolyl, thiazolyl, benzothiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in its non-aromatic meaning relates to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are azetidinyl, pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, ($C_1$-$C_6$) alkyl, ($C_2$-$C_6$)alkenyl, ($C_2$-$C_6$)alkynyl, ($C_1$-$C_6$)alkoxy, hydroxy, hydroxy($C_1$-$C_6$)alkyl, ($C_1$-$C_3$)alkoxy($C_1$-$C_3$)alkyl, mercapto, mercapto($C_1$-$C_6$)alkyl, ($C_1$-$C_6$)alkylthio, halo (including fluoro, bromo and chloro), fully or partially fluorinated ($C_1$-$C_3$)alkyl, ($C_1$-$C_3$)alkoxy or ($C_1$-$C_3$)alkylthio such as trifluoromethyl, trifluoromethoxy, and trifluoromethylthio, nitro, nitrile (—CN), oxo (=O), phenyl, phenyl($C_1$-$C_3$) alkyl-, phenoxy, monocyclic heteroaryl, heteroaryl($C_1$-$C_3$)

alkyl-, or heteroaryloxy with 5 or 6 ring atoms, cycloalkyl having 3 to 6 ring carbon atoms, —COOR$^A$, —COR$^A$, —OCOR$^A$, —SO$_2$R$^A$, —CONR$^A$R$^B$, —CONHNH$_2$, —SO$_2$NR$^A$R$^B$, —NR$^A$R$^B$, —NHNH$_2$, —OCONR$^A$R$^B$, —NR$^B$COR$^A$, —NR$^B$COOR$^A$, —NR$^B$SO$_2$OR$^A$ or —NR$^A$CONR$^A$R$^B$ wherein R$^A$ and R$^B$ are independently hydrogen or a (C$_1$-C$_6$)alkyl, hydroxy(C$_1$-C$_6$)alkyl, or (C$_1$-C$_3$)alkoxy(C$_1$-C$_3$)alkyl group or, in the case where R$^A$ and R$^B$ are linked to the same N atom, R$^A$ and R$^B$ taken together with that nitrogen may form a cyclic amino ring such as morpholinyl, piperidinyl. piperazinyl, or 4-(C$_1$-C$_6$)alkyl-piperizinyl such as 4-methyl-piperazinyl. Where the substituent is phenyl, phenyl(C$_1$-C$_3$)alkyl-, phenoxy or monocyclic heteroaryl, heteroaryl(C$_1$-C$_3$)alkyl-, or heteroaryloxy with 5 or 6 ring atoms, the phenyl or heteroaryl ring thereof may itself be substituted by any of the above substituents except phenyl, phenyl(C$_1$-C$_3$)alkyl-, phenoxy, heteroaryl, heteroaryl(C$_1$-C$_3$)alkyl-, or heteroaryloxy. An "optional substituent" or "substituent" may be one of the foregoing specified groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesunfonic, glutamic, lactic, and mandelic acids and the like. For a review on suitable salts, see *Handbook of Pharmaceutical Salts: Properties, Selection, and Use* by Stahl and Wermuth (Wiley-VCH, Weinheim, Germany, 2002).

Compounds of the invention may be prepared in crystalline form, and may be in the form of hydrates and solvates. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water. Reference herein to a compound of the invention is to be understood as including hydrates and solvates thereof.

Compounds with which the invention is concerned which may exist in one or more stereoisomeric form, because of the presence of asymmetric atoms or rotational restrictions, can exist as a number of stereoisomers with R or S stereochemistry at each chiral centre or as atropisomeres with R or S stereochemistry at each chiral axis. The invention includes all such enantiomers and diastereoisomers and mixtures thereof.

Some compounds of formula (I) may be administered as prodrugs, which are considered to be derivatives of compounds of formula (I) which may have little or no pharmacological activity themselves but which, when administered into or onto the body, are converted into compounds of formula (I) having the desired activity, for example, by hydrolytic cleavage. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs can, for example, be produced by replacing appropriate functionalities present in the compounds of formula (I) with certain moieties known to those skilled in the art as 'pro-moieties' as described, for example, in Design of Prodrugs by H. Bundgaard (Elsevier, 1985).

Metabolites of compounds of formula (I), that is, compounds formed in vivo upon administration of the drug may also have antibacterial activity. Some examples of metabolites include:
(i) where the compound of formula (I) contains a methyl group, an hydroxymethyl derivative thereof (—CH$_3$→—CH$_2$OH):
(ii) where the compound of formula (I) contains an alkoxy group, an hydroxy derivative thereof (—OR→—OH);
(iii) where the compound of formula (I) contains a tertiary amino group, a secondary amino derivative thereof (—NR$^1$R$^2$→—NHR$^1$ or —NHR$^2$);
(iv) where the compound of formula (I) contains a secondary amino group, a primary derivative thereof (—NHR$^1$→—NH$_2$);
(v) where the compound of formula (I) contains a phenyl moiety, a phenol derivative thereof (-Ph→-PhOH); and
(vi) where the compound of formula (I) contains an amide group, a carboxylic acid derivative thereof (—CONH$_2$→COOH).

Structural Features

The compounds with which the invention is concerned may have, for example, the following features, in any compatible combination:

$Z_1$ is —N═ or —CH═, and $Z_2$ is —N═ or —C(R$_1$)═, wherein R$_1$ is hydrogen, methyl, ethyl, ethenyl, ethynyl, methoxy, mercapto, mercaptomethyl, halo (including fluoro, bromo and chloro), fully or partially fluorinated (C$_1$-C$_2$)alkyl, (C$_1$-C$_2$)alkoxy or (C$_1$-C$_2$)alkylthio such as trifluoromethyl, trifluoromethoxy, and trifluoromethylthio, nitro, or nitrile (—CN)). Thus, one example of $Z_2$ is —CF═. In one class of compounds $Z_1$ and $Z_2$ are both —CH═. However, presently it is preferred that $Z_1$ be —CH═ and $Z_2$ be —CF═, so that the compounds (I) are substituted benzothiazoles.

X may be, for example, —C(O)O— or —C(O)NH—. Within this subclass, m may be 0 and Q may be, for example, hydrogen, cyclopropyl, cyclobutyl, cyclopentyl or cyclohexyl. Also within this subclass, m may be 1 and Q hydrogen, with Alk being, for example —CH$_2$—, —(CH$_2$)$_2$— or —(CH$_2$)$_3$—. Presently, when m is 1 it is preferred that X be —C(O)NH—, Alk be —(CH$_2$)$_2$— and Q be hydrogen.

R$_2$ is a group Q$^1$-[Alk$^1$]$_q$-Q$^2$-.

Alk$^1$ when present is an optionally substituted, divalent, straight chain or branched C$_1$-C$_6$ alkylene, or C$_2$-C$_6$ alkenylene or C$_2$-C$_6$ alkynylene radical which may contain or terminate in an ether (—O—), thioether (—S—) or amino (—NR)— link. Examples of such radicals include —CH$_2$—, —CH(OH)—, —CH$_2$CH$_2$—, —CH$_2$CH$_2$CH$_2$—, —CH═CH—, —C≡C—, —CH$_2$CH═CH—, —CH$_2$C≡C—, —CH$_2$NH—, —C(═O)NH—, —CH$_2$OCH$_2$—, —CH$_2$CH$_2$C(═O)NH—.

Q$^2$ is an optionally substituted divalent monocyclic carbocyclic or heterocyclic radical having 5 or 6 ring atoms or an optionally substituted divalent bicyclic carbocyclic or heterocyclic radical having 9 or 10 ring atoms. Examples of such radicals include those having optionally substituted thienyl, benzothienyl, furyl, benzfuryl, pyrrolyl, imidazolyl, benzimidazolyl, thiazolyl, benzothiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl, indazolyl. azetidinyl, pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, piperidinyl, piperazinyl, indolyl, morpholinyl, benzfuranyl, pyranyl, isoxazolyl, benzimidazolyl, cyclopropyl, cyclobutyl, cyclopentyl, cyclohexyl, phenyl, and naphthyl rings.

$Q^1$ is hydrogen, an optional substituent, or an optionally substituted carbocyclic or heterocyclic radical having 3-7 ring atoms. Optional substituents include those particularised above in the discussion of the term "optional substituent". Carbocyclic or heterocyclic rings having 3-7 ring atoms include those monocyclic rings listed in the preceding paragraph, as well as cyclopentyl and homopiperazinyl rings.

In the group $R_2$, $Q^2$ may be an optionally substituted divalent nitrogen-containing heterocyclic radical having 5 or 6 ring atoms, such as an optionally substituted divalent pyridonyl, pyridyl, pyrazolyl, pyrimidinyl, thiazolyl, or pyrrolyl radical, or $Q^2$ when present may be a divalent nitrogen-containing bicyclic carbocyclic or heterocyclic radical having 9 or 10 ring atoms, such as quinolinyl, isoquinolinyl, benzimidazolyl or 5-azaindolyl. Presently preferred $Q^2$ rings include optionally substituted pyridine, pyrimidine, pyrazine, pyran-2-one, pyrimidine-4-one or pyridine-2-one rings, such as an optionally substituted pyridine-3-yl ring, an optionally substituted pyrimidine-5-yl ring, an optionally substituted pyrazine-2-yl ring, an optionally substituted pyran-2-one-4-yl ring or an optionally substituted pyridine-2-one-4-yl ring. Presently preferred optional substituents in $Q^2$ include $CH_3$—, $CH_3O$—, —CN, and —$NH_2$.

In the group $R_2$, q is 0 or 1. When q is 1, $Alk^1$ is present and may be, for example, an optionally substituted divalent $C_1$-$C_3$ alkylene radical which may optionally include an —NH— link, or optionally terminate in an —NH— link to $Q^2$. In a particular case, $Alk^1$ is a divalent $C_2$-$C_3$ alkylene radical which terminates in an —NH— link to $Q^2$, and which is oxo-substituted on the C atom adjacent that —NH— link, whereby $Alk^1$ has the formula —$(CH_2)_{0-2}C(=O)NH$—. In other cases $Alk^1$ has the formula —$(CH_2)_{1-2}NHC(=O)$—, with the (C=O) being linked to $Q^2$.

In the group $R_2$, $Q^1$ may be, for example, hydrogen, or an optional substituent as particularised above. In some embodiments $Q^1$ is a group of formula —$NR^AR^B$, wherein $R^A$ and $R^B$ are independently hydrogen or a $(C_1$-$C_6)$alkyl, hydroxy$(C_1$-$C_6)$alkyl, or $(C_1$-$C_3)$alkoxy$(C_1$-$C_3)$alkyl group, or $R^A$ and $R^B$ taken together with that nitrogen form a cyclic amino ring, for example, a piperidine, morpholine, thiomorpholine, azetidine, pyrrolidine or piperazine ring, the latter being optionally N-substituted, for example by $C_1$-$C_3$ alkyl, or hydroxy-$C_1$-$C_3$ alkyl or $C_1$-$C_3$ alkoxy-$C_1$-$C_3$ alkyl.

In the group $R_2$, $Q^2$ may be, for example, an optionally substited heterocyle such as pyridinyl, pyrimidinyl or pyrazinyl radical. In some embodiments q may be 0 and $Q^1$ may be, for example, an optionally substited heterocyle such as oxadiazolyl, tetrazolyl, piperidinyl or pyrrolidinyl. In the latter two cases, a currently preferred optional substituent in $Q^1$ is —COON.

In the group $R_2$, $Q^2$ may be an optionally substituted heterocyle such as pyrimidine-4-one or pyridine-2-one, q may be 1 and $Q^1$ may be an optionally substituted heterocyclic radical having 3-7 ring atoms, such as an optionally substituted pyridinyl group. In this substet of compounds of the invention $Alk^1$ may be, for example —$CH_2$—.

The examples herein provide specific examples of $Q^1$, and $Q^2$ radicals which may be present in $R_2$.

Examples of $R_2$ groups include the following:

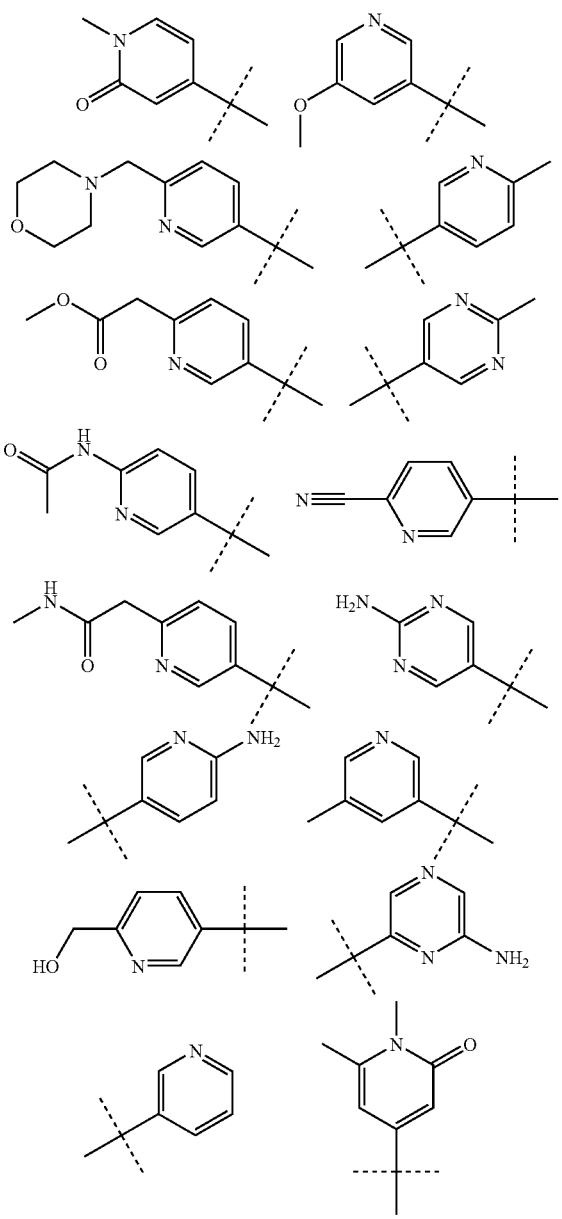

Specific compounds of the invention include those of the Examples herein, and their salts and N-oxides.

Utilities and Compositions

As mentioned above, the compounds with which the invention are concerned are antimicrobially active, and may therefore be of use as topical antibacterial disinfectants, or in the treatment of microbial infection in humans and non-human animals e.g. other mammals, birds and fish. Since the type II topoisomerase target of the compounds of the invention is a universal bacterial enzyme, the compounds of the invention inhibit growth of a variety of bacterial species, of the Gram-positive and/or Gram negative classes, such as staphylococci, enterococci, streptococci, propionibacteria, haemophili and moraxellas for example *Staphylococcus aureus, Staphylococcus epidermidis, Enterococcus faecalis, Enterococcus faecium, Streptococcus pneumoniae, Streptococcus pyogenes, Propionibacterium acnes, Haemophilus influenzae* and *Moraxella catarrhalis*. The compounds with which the invention is concerned are therefore useful for the treatment of bacterial infection or contamination, for example in the treatment of, inter alia, Gram-positive infections community acquired pneumonias, acne vulgaris, impetigo and infected atopic dermatitis.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy. Optimum dose levels and frequency of dosing will be determined by clinical trial as is required in the art.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may be inhaled using a suitable device such as a dry powder inhaler, a nebuliser, a metered dose inhaler or a liquid spray system.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Synthesis and Example Compounds

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to the one skilled in the art. Typical literature sources are "*Advanced organic chemistry*", 4$^{th}$ Edition (Wiley), J March, "*Comprehensive Organic Transformation*", 2$^{nd}$ Edition (Wiley), R. C. Larock, "*Handbook of Heterocyclic Chemistry*", 2$^{nd}$ Edition (Pergamon), A. R. Katritzky), review articles such as found in "*Synthesis*", "*Acc. Chem. Res.*", "*Chem. Rev*", or primary literature sources identified by standard literature searches online or from secondary sources such as "*Chemical Abstracts*" or "*Beilstein*".

Examples of synthetic approaches and schemes for the preparation of compounds (I) are given in the Examples herein.

The invention will now be illustrated by reference to the following Examples:

Abbreviations
DMSO—dimethylsulfoxide
HPLC—high performance liquid chromatography
MS—mass spectrometry
NMR—nuclear magnetic resonance
Rt—retention time
THF—tetrahydrofuran
TLC—thin layer chromatography
HOBT—N-hydroxybenzotriazole
Boc—t-butoxycarbonyl
EDC.HCl—1-ethyl-3-(3-dimethylaminopropyl)carbodiimide hydrochloride
Pd2(dba)3—tris(dibenzyledineacetone)dipalladium(0)
DIPEA—N,N-Diisopropylethylamine
PdCl2(dppf)—Dichlorobis(triphenylphosphine)-palladium (II)
NMP—N-methylpyrrolidinone
DMF—N,N-dimethylformamide
TBAB—Tetra-n-butylammonium bromide
EtOAc—Ethyl acetate
DCM—dichloromethane Scheme-1:

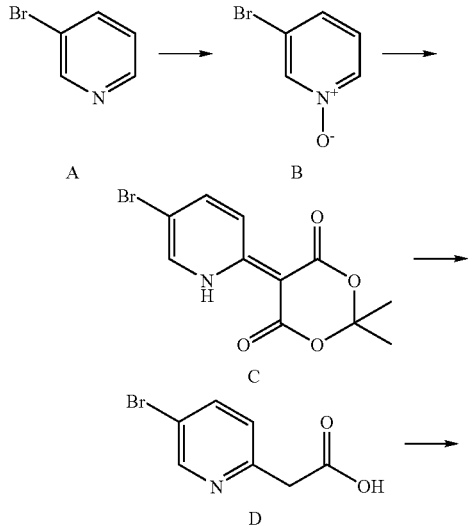

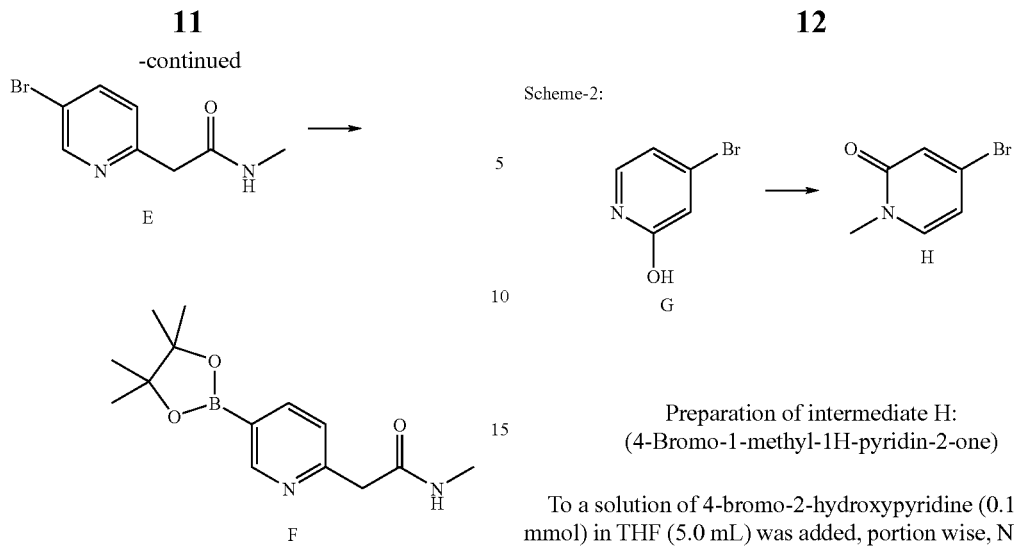

Synthesis up to intermediate D:
[(5-Bromo-pyridin-2-yl)-acetic acid]

As Per Reference: *Tetrahedron*, 53, 24, 1997, 8257-8268.

Synthesis of intermediate E:
[2-(5-Bromo-pyridin-2-yl)-N-methyl-acetamide]

To a suspension of 5-bromo-pyridin-2-yl-acetic acid (0.87 g, 4.0 mmol) in THF (12 mL) was added HOBt (0.74 g, 4.8 mmol) and EDCI.HCl (0.85 g, 4.4 mmol) and stirred the resulting reaction mixture for 15-20 min at room temperature followed by drop-wise addition of methyl amine (2.0 M in THF, 4.05 mL, 8.0 mmol). The resulting mixture was then continued to stir for 6-7 h at room temperature. After completion of reaction, water was added and extracted with ethyl acetate. The crude residue was purified over silica (60-120 M) using dichloromethane:methanol (97.5:2.5) to obtain the pale-yellow solid compound (0.25 g, 27%). $^1$H NMR (DMSO-d6, 400 MHz): δ 2.58 (d, J=4.8 Hz, 3H), 3.57 (s, 2H), 7.33 (d, J=1H), 7.96 (d, J=2.4 Hz & 8.4 Hz, 1H), 8.00 (br s, 1H) and 8.58 (d, J=2.4 Hz, 1H). MS: 229.11 (M+H$^+$).

Synthesis of intermediate F: N-methyl-2-[5-(4,4,5,5-tetramethyl-[1,3,2]dioxaborolan-2-yl)-pyridin-2-yl]-acetamide A solution of 2-(5-bromo-pyridin-2-yl)-N-methyl-acetamide] (0.5 g, 0.22 mmol) in 1,4-dioxane was degassed by bubbling nitrogen for 15-20 min followed by sequential addition of Pd$_2$(dba)$_3$ (0.01 g, 0.01 mmol), bis pinacolato diboron (0.06 g, 0.24 mmol), tricyclohexyl phosphine (0.007 g 0.03 mmol) and potassium acetate (0.03 g, 0.033 mmol). The reaction mixture was then again degassed for another 15-20 min and then heated up to 80° C. for overnight. After completion of reaction (TLC monitoring) the reaction mixture was cooled, diluted with ethyl acetate and filtered through celite bed. The filtrate was dried over Na$_2$SO$_4$, filtered, concentrated and washed with hexane. The crude oily compound (60 mg) was used further without purification. MS: 277.26 (M+H$^+$).

Scheme-2:

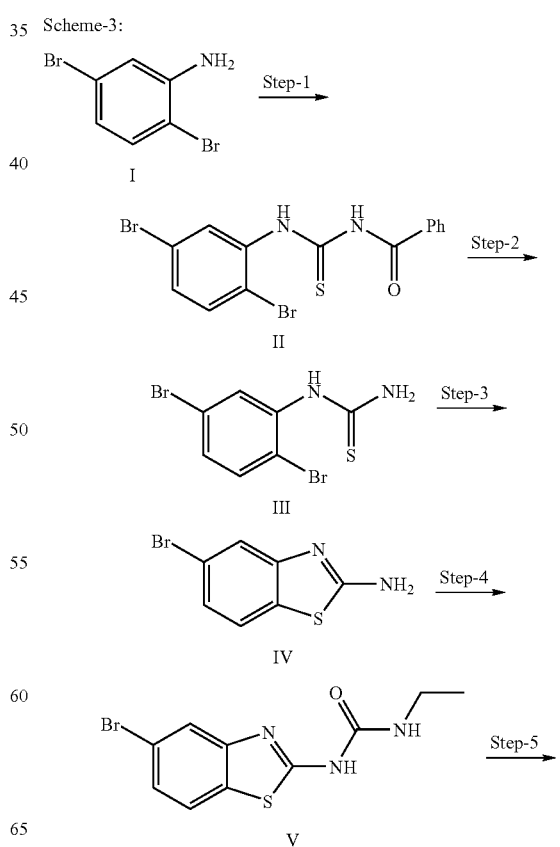

Preparation of intermediate H:
(4-Bromo-1-methyl-1H-pyridin-2-one)

To a solution of 4-bromo-2-hydroxypyridine (0.10 g, 0.57 mmol) in THF (5.0 mL) was added, portion wise, NaH (60% dispersion in mineral oil, 0.02 g, 0.86 mmol). The resulting solution was stirred at room temperature for 5 min followed by addition of methyl iodide (0.11 mL, 1.72 mmol). The reaction mixture was then allowed to stir overnight at room temperature. After the completion of reaction, THF was distilled off, added water and extracted with ethyl acetate (3×25 mL). The combined organics was washed with water, brine, dried (Na$_2$SO$_4$), filtered and concentrated to obtain the desired product (0.10 g, 92%). $^1$H NMR (DMSO-d6, 400 MHz): δ 3.43 (s, 3H), 6.45 (dd, J=2.40 and 7.20 Hz, 1H), 6.69 (d, J=2.40 Hz, 1H) and 7.68 (d, J=7.20 Hz, 1H). MS: 188.05 (M+H$^+$).

Scheme-3:

-continued

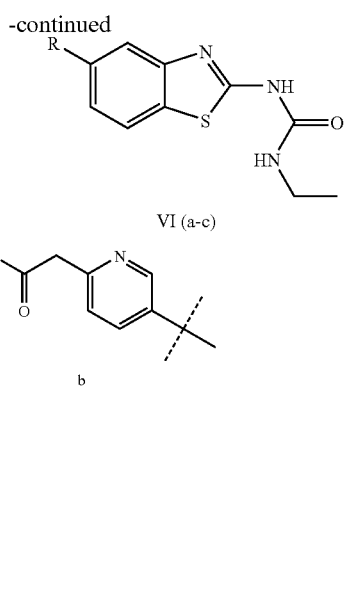

VI (a-c)

Preparation of 1-Benzoyl-3-(2,5-dibromo-phenyl)-thiourea (Step-1): (II)

To a solution of 2,5-dibromo-phenylamine I (2.44 g, 9.72 mmol) in acetone (60 mL) was added benzoylisothiocyanate (1.74 g, 26.0 mL, 10.6 mmol) at room temperature. After 15 min, solid precipitated out. The reaction mixture was continued to stir for 30 min at room temperature. After completion of reaction (TLC monitoring) acetone was distilled off and crude solid filtered with hexane (100 mL) and again washed with hexane (100 mL) to obtain the desired compound as pale-yellow solid (3.9 g, 97%). $^1$H NMR (DMSO-d6, 400 MHz): δ 7.47 (dd, J=6.4, 6.0 Hz, 1H), 7.53 (m, 2H), 7.66 (s, 1H), 7.70 (m, 1H), 7.99 (m, 1H), 8.01 (s, 1H), 8.17 (d, J=2.4 Hz, 1H), 11.91 (br s, 1H) and 12.63 (br s, 1H).

Preparation of 2,5-Dibromo-phenyl-thiourea (Step-2): (III)

To a solution of 1-benzoyl-3-(2,5-dibromo-phenyl)-thiourea II (3.90 g, 11.8 mmol) in THF (80 mL) was added NaOH solution (1.13 g in 20 mL H$_2$O) at room temperature. The reaction mixture was then heated up to 60-65° C. overnight. After completion of the reaction (TLC monitoring) THF was distilled off followed by addition of water, and extracted with ethyl acetate (2×50 mL). The combined organic layers were combined and dried over anhydrous Na$_2$SO$_4$, filtered and evaporated to dryness under reduced pressure. The crude residue was washed with mixture of hexane and diethyl ether (95:5) and dried under high vacuum to obtain the desired product as pale-yellow solid (2.5 g, 86%). $^1$H NMR (DMSO-d6, 400 MHz): δ 7.35 (dd, J=8.80 and 2.80 Hz, 1H), 7.48 (br s, 1H), 7.60 (d, J=8.40 Hz, 1H), 7.87 (d, J=2.40 Hz, 1H), 8.0 (br s, 1H) and 9.33 (br s, 1H). MS: 308.98 (M+H$^+$).

Preparation of 5-(Bromo-benzothiazol-2-yl)-amine (Step-3): (IV)

To a solution of 2,5-dibromo-phenyl)-thiourea III (2.0 g, 6.5 mmol) in N-methylpyrrolidone (10 mL) was added NaH (60% dispersion in mineral oil, 0.24 g, 9.70 mmol) at room temperature. The reaction mixture was heated up to 160° C. for 1 h. After completion of reaction (TLC monitoring), the reaction mixture was allowed to come to room temperature. Water (100 mL) was added to the reaction mixture and extracted with ethyl acetate (3×50 mL). The combined organic layers were dried over anhydrous Na$_2$SO$_4$, filtered and evaporated to dryness under reduced pressure. The crude residue was purified over silica gel (100-200M) using hexane and ethyl acetate (80:20) to obtain the desired product as white solid (0.23 g, 16%). $^1$H NMR (DMSO-d6, 400 MHz): δ 7.15 (dd, J=2.0 and 8.40 Hz, 1H), 7.47 (d, J=2.0 Hz, 1H), 7.62 (d, J=8.40 Hz, 1H) and 7.68 (br s, 2H). MS: 229.01 (M+H$^+$).

Preparation of 1-(5-Bromo-benzothiazol-2-yl)-3-ethyl-urea (Step-4): (V)

To a suspension of 5-bromo-benzothiazol-2-ylamine IV (0.23 g, 1.0 mmol) in 1,4-dioxane (10 mL) was added ethyl-isocyanate (0.36 g, 0.38 mL, 5.02 mmol). The reaction mixture was heated up to 78-80° C. overnight. After completion of reaction (TLC monitoring), 1,4-dioxane was distilled off and co evaporated with hexane. The resulting solid was treated with water to 60-70° C. for 3-5 h. The resulting solid was filtered off and again washed with hot water, dried under high vacuum to obtain the desired product as off-white solid (0.15 g, 50%). $^1$H NMR (DMSO-d6, 400 MHz): δ 1.08 (t, J=7.20 Hz, 3H), 3.18 (m, 2H), 6.70 (br s, 1H), 7.36 (dd, J=1.60 and 8.0 Hz, 1H), 7.79 (d, J=1.60 Hz, 1H), 7.84 (d, J=8.40 Hz, 1H) and 10.85 (br s, 1H). MS: 300.07 (M+H$^+$).

Preparation of 1-Ethyl-3-(5-pyridin-3-yl-benzothiazol-2-yl)-urea: (VI-a)

Example 1

To a solution of 1-(5-bromo-benzothiazol-2-yl)-3-ethyl-urea (0.20 g, 0.67 mmol) in N,N-dimethylformamide:H$_2$O (4:1, 5.0 mL) was added pyridine-3-boronic acid (0.16 g, 1.30 mmol) and potassium phosphate tribasic (0.28 g, 1.30 mmol) at room temperature under nitrogen atmosphere. The reaction mixture was degassed by bubbling nitrogen for 15-20 min followed by addition of PdCl$_2$(PPh$_3$)$_2$ (0.05 g, 0.07 mmol). The reaction mixture was then again degassed for another 15-20 min and then heated up to 90° C. for 30 min. After completion of reaction (TLC monitoring) the reaction mixture was cooled, water was added and extracted with ethyl acetate, dried over Na$_2$SO$_4$, filtered and evaporated to dryness. The crude residue was washed with ether to obtain the desired product as a pale yellow solid (0.13 g, 65%). $^1$H NMR (DMSO-d6, 400 MHz): δ 1.09 (t, J=7.2 Hz, 3H), 3.20 (m, 2H), 6.74 (br s, 1H), 7.48-7.51 (m, 1H), 7.56 (dd, J=2.0 and 8.40 Hz, 1H), 7.94 (s, 1H), 7.99 (d, J=8.0 Hz, 1H), 8.13 (dd, J=2.0 and 8.0 Hz, 1H), 8.56 (m, 1H), 8.94 (d, J=2.0 Hz, 1H) and 10.78 (br s, 1H). MS: 299.23 (M+H). HPLC Purity (Acquity BEH C-18, 2.1×100 mm, 1.7 μm, 253.0 nm): 98.15% (Rt=4.93 min).

Preparation of 2-{5-[2-(3-Ethyl-ureido)-benzothiazol-5-yl]-pyridin-2-yl}-N-methyl-acetamide: (VI-b)

Example 2

To a solution of 1-(5-bromo-benzothiazol-2-yl)-3-ethyl-urea (0.03 g, 0.10 mmol) in N,N-dimethylformamide:H$_2$O (3:0.5, 3.5 mL) was added N-methyl-2-[5-(4,4,5,5-tetramethyl-[1,3,2]dioxaborolan-2-yl)-pyridin-2-yl]-acetamide F (0.09 g, 0.30 mmol) and potassium phosphate tribasic (0.03 g, 0.12 mmol) at room temperature under nitrogen atmosphere. The reaction mixture was degassed by bubbling nitrogen for 15-20 min followed by addition of PdCl$_2$(PPh$_3$)$_2$ (0.007 g, 0.01 mmol). The reaction mixture was the again degassed for another 15-20 min and then heated up to 110° C. for 6 h. After completion of reaction (TLC monitoring) the reaction mixture was cooled, water was added and extracted with ethyl acetate, dried over Na$_2$SO$_4$, filtered and evaporated to dryness under high vacuum. The crude residue was purified over silica gel (230-400 M) using dichloromethane:methanol [88:12] to obtain the desired compound (0.007 g, 20%). $^1$H NMR (DMSO-d6, 400 MHz): δ 1.08 (t, J=7.20 Hz, 3H), 2.60 (d, J=4.8 Hz, 3H), 3.18 (m, 2H), 3.63 (s, 2H), 7.09 (br s, 1H), 7.23 (s, 1H), 7.42 (d, J=8.0 Hz, 1H), 7.52 (dd, J=1.6 &, 8.0 Hz, 1H), 7.86 (s, 1H), 7.92 (s, 1H), 8.05 (s, 1H), 8.82 (d, J=2.4 Hz, 1H) and 10.75 (br s, 1H). MS: 370.25 (M+H$^+$). Qualitative HPLC Purity (Acquity BEH C-18, 2.1×100 mm, 1.7 μm, 254.0 nm): 85.81% (Rt=4.47 min).

Preparation of 1-Ethyl-3-(5-(1-methyl-2-oxo-1,2-dihydro-pyridin-4-yl)-benzothiazol-2-yl)urea: (VI-c)

Example 3

To a solution of 1-(5-bromo-benzothiazol-2-yl)-3-ethyl-urea (0.13 g, 0.43 mmol) in DMSO (4 mL) was added bis neopentyl glycolatodiboron (0.20 g, 0.86 mmol) and potassium acetate (0.13 g, 1.30 mmol) at room temperature under nitrogen atmosphere. The reaction mixture was degassed by bubbling nitrogen for 15-20 min followed by addition of PdCl$_2$(dppf) (0.035 g, 0.043 mmol). The reaction mixture was again degassed for 15-20 min. The resulting solution was the heated up to 80° C. for 3 h. The reaction mixture was cooled followed by sequential addition of 4-bromo-1-methyl-1H-pyridin-2-one H (0.13 g, 0.65 mmol), Cs$_2$CO$_3$ solution in water (0.22 g in 0.2 mL H$_2$O, 0.65 mmol) and Pd(PPh$_3$)$_4$ (0.05 g, 0.043 mmol). The resulting mixture was degassed for 15 min and heated to 100° C. for further 18 h. After completion of reaction (TLC monitoring), the reaction mixture was cooled, diluted with ethyl acetate and washed with water (2×20 mL), brine, dried over Na$_2$SO$_4$, filtered and evaporated to dryness under high vacuum. The crude residue (0.10 g) was purified by Prep HPLC to obtain the desired product (0.01 g, 7%). $^1$H NMR (DMSO-d6, 400 MHz): δ 1.09 (t, J=7.20 Hz, 3H), 3.18 (q, J=6.8 Hz, 2H), 3.45 (s, 3H), 6.65 (dd, J=7.20 Hz & 2.0 Hz, 1H), 6.72 (s, 1H), 6.79 (br s, 1H), 7.54 (dd, J=8.0 Hz & 2.0 Hz, 1H), 7.77 (d, J=7.2 Hz, 1H), 7.91 (s, 1H), 7.96 (m, 1H), 10.37 (br s, 1H). MS: 329.29 (M+H$^+$). Qualitative HPLC Purity (Acquity BEH C-18, 2.1×100 mm, 1.7 μm, 264.0 nm): 91.08% (Rt=4.45 min).

Scheme-4:

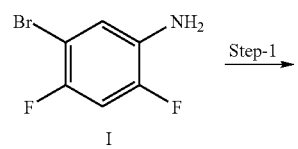

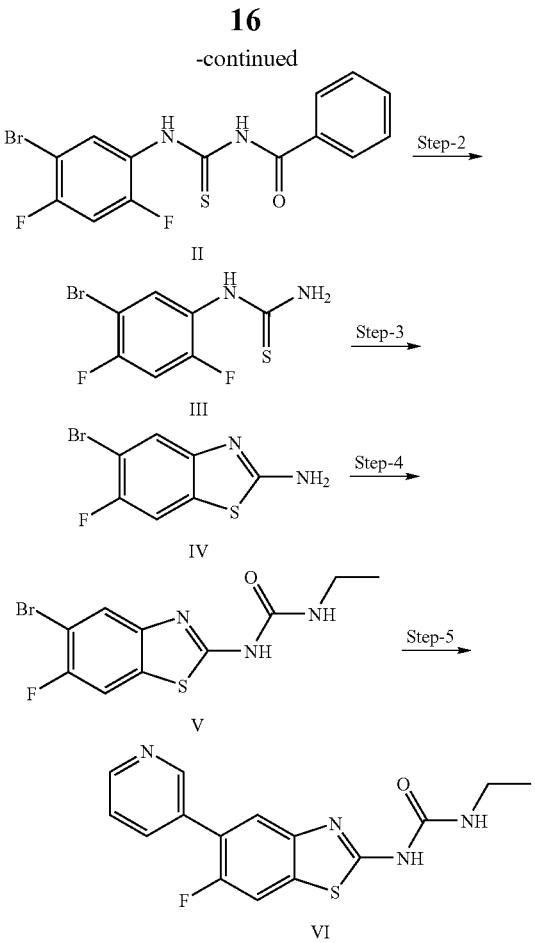

1-Benzoyl-3-(5-bromo-2,4-difluoro-phenyl)-thiourea (Step-1): II

To a solution of 5-bromo-2,4-difluoro aniline (1.0 g, 4.81 mmol) in acetone (25.0 mL) was added drop wise benzoyl isothiocyanate (0.71 mL, 5.29 mmol). The resulting reaction mixture was allowed to stir at room temperature for 30 min. After the completion of the reaction (TLC monitoring), the solvent was evaporated and the residue was washed with hexane and ether to get the title compound (1.70 g, quantitative yield) as a white solid. $^1$H-NMR (400 MHz, CDCl$_3$): δ 7.02-7.06 (m, 1H), 7.56 (t, J=8.0 Hz, 2H), 7.68 (t, J=7.60 Hz, 1H), 7.91 (d, J=7.60 Hz, 2H), 8.67 (t, J=7.60 Hz, 1H), 9.15 (br s, 1H) and 12.65 (br s, 1H).

(5-Bromo-2,4-difluoro-phenyl)-thiourea (Step-2): III

To a solution of 1-benzoyl-3-(5-bromo-2,4-difluoro-phenyl)-thiourea (1.70 g, 4.60 mmol) in THF (35.0 mL) was added a solution of NaOH (0.97 g, 24.25 mmol) in water (13.0 mL). The resulting reaction mixture was stirred at 70° C. for 15 h. After the completion of the reaction (TLC monitoring), THF was evaporated, added water and extracted with EtOAc (3×50 mL). The combined organics was washed with brine and concentrated to obtain the desired compound (1.0 g, 83%). MS: 267.03 (M+H)$^+$.

5-Bromo-6-fluoro-benzothiazol-2-ylamine (Step-3): IV

To a solution of (5-Bromo-2,4-difluoro-phenyl)-thiourea (0.75 g, 2.80 mmol) in NMP (5.0 mL) was added NaH (0.17 g, 4.21 mmol, 60% dispersion in oil) portion wise. The reaction mixture was then heated at 130° C. for 2 h. The reaction mixture was then poured onto crushed ice and extracted with EtOAc (3×50 mL). The combined organics was evaporated to get the crude residue that was purified over silica gel (100-200 M, 12% EtOAc-Hexane) to obtain the desired compound (0.36 g, 52%). $^1$H-NMR (400 MHz, DMSO-$d_6$): δ 7.57 (d, J=6.40 Hz, 1H), 7.66 (br s, 2H) and 7.79 (d, 8.80 Hz, 1H).

1-(5-Bromo-6-fluoro-benzothiazol-2-yl)-3-ethyl-urea (Step-4): V

To a solution of 5-bromo-6-fluoro-benzothiazol-2-ylamine (0.36 g, 1.45 mmol) in 1,4-dioxane (25.0 mL) was added ethyl isocyanate (0.69 mL, 8.74 mmol) and the resulting reaction mixture was heated at 80° C. for 15 h. After the completion of the reaction (TLC monitoring) the solvent was evaporated. The residue thus obtained was stirred with water at 60° C. for 5 h. The solution was then filtered and washed with ether to get the title compound (0.30 g, 69%). $^1$H-NMR (400 MHz, DMSO-$d_6$): δ 1.08 (t, J=6.80 Hz, 3H), 3.17 (m, 2H), 6.69 (br s, 1H), 7.92 (d, J=6.40 Hz, 1H), 8.0 (d, J=8.40 Hz, 1H) and 10.86 (br s, 1H).

1-Ethyl-3-(6-fluoro-5-pyridin-3-yl-benzothiazol-2-yl)-urea (Step-5)

Example 4

To a solution of 1-(5-Bromo-6-fluoro-benzothiazol-2-yl)-3-ethyl-urea (0.30 g, 0.94 mmol) in DMF:H$_2$O (10:1, 11 mL) was added pyridine-3-boronic acid (0.23 g, 1.88 mmol) and K$_3$PO$_4$ (0.24 g, 1.13 mmol) under nitrogen atmosphere at room temperature. The reaction mixture was then degassed for half an hour followed by the addition of [1,1'-bis(diphenylphosphino)ferrocene]dichloropalladium(II) complex with CH$_2$Cl$_2$ (0.13 g, 0.16 mmol). The reaction mixture was then again degassed for half an hour and heated at 120° C. for 1 h under nitrogen atmosphere. After the completion of the reaction (TLC monitoring), DMF was distilled off; water was added to the reaction mixture and extracted with ethyl acetate. The combined organic layers were dried over anhydrous Na$_2$SO$_4$, and evaporated to dryness under reduced pressure. The crude residue was purified over silica gel (100-200 M) using EtOAc-Hexane (55:45) to provide the title compound as beige solid (0.21 g, 70%). M.P. 199.10° C. $^1$H-NMR (400 MHz, DMSO-$d_6$): δ 1.10 (t, J=6.80 Hz, 3H), 3.20 (m, 2H), 6.71 (br s, 1H), 7.50-7.53 (m, 1H), 7.78 (d, J=6.80 Hz, 1H), 7.97 (d, J=10.40 Hz, 1H), 8.01 (dd, J=1.60 & 8.0 Hz, respectively, 1H), 8.61 (dd, J=1.20 & 4.80 Hz, respectively, 1H), 8.79 (s, 1H) and 10.81 (br s, 1H). MS: 317.21 (M+H)$^+$._Qualitative HPLC Purity_(Xbridge C18, 250×4.6 mm, 255 nm): 98.15 (Rt=13.49 min).

Scheme-5:

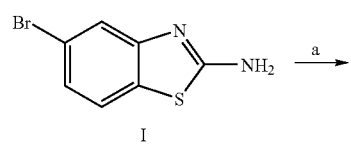

I

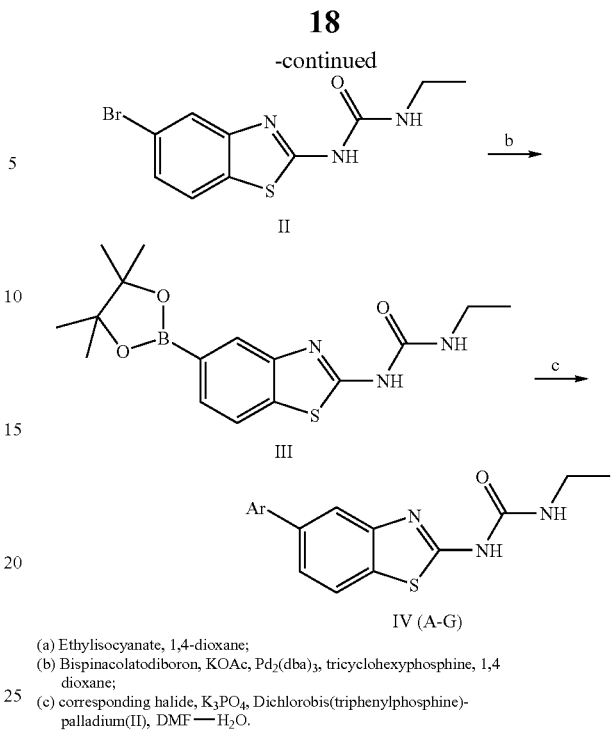

(a) Ethylisocyanate, 1,4-dioxane;
(b) Bispinacolatodiboron, KOAc, Pd$_2$(dba)$_3$, tricyclohexyphosphine, 1,4-dioxane;
(c) corresponding halide, K$_3$PO$_4$, Dichlorobis(triphenylphosphine)-palladium(II), DMF—H$_2$O.

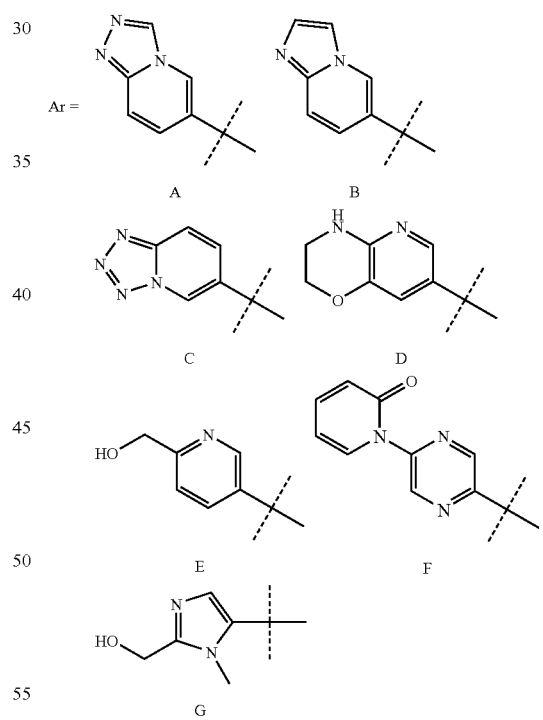

Preparation of 1-(5-bromobenzo[d]thiazol-2-yl)-3-ethylurea (II)

To a solution of 2-amino-5-bromo benzothiazole (0.23 g, 1.0 mmol) in 1,4-dioxane (8.0 mL) was added ethylisocyanate (3.96 mL, 5.0 mmol) and the resulting solution was heated to 80° C. for 16 h. After the completion of the reaction (TLC monitoring), 1,4-dioxane was distilled off followed by co-distillation with n-hexane (2 times). The residue was then stirred with water at 90° C. for 2 h followed by filtration to obtain the desired product that was further washed with hot water and then dried. The residue was finally washed with ether to obtain the desired product (0.18 g, 60%).

Preparation of 1-ethyl-3-(5-(4,4,5,5-tetramethyl-1,3, 2-dioxaborolan-2-yl)benzo[d]thiazol-2-yl)urea (III)

A solution of 1-(5-bromobenzo[d]thiazol-2-yl)-3-ethylurea II (0.20 g, 0.69 mmol), bispinacolatodiboron (0.19 g, 0.80 mmol) and KOAc (0.082 g, 1.03 mmol) in 1,4-dioxane (5.0 mL) was degassed by flushing with nitrogen for 15 min. Tricyclohexylphosphine (0.023 g, 0.08 mmol) and tris(dibenzyledineacetone)dipalladium(0) (0.03 g, 0.03 mmol) was then added to the reaction mixture, which was again degassed by nitrogen for 15 min. The resulting reaction mixture was heated to 80-85° C. for 2 h. After the completion of the reaction (TLC monitoring), the reaction mixture was filtered through celite bed and the filtrate was concentrated to get the crude residue that was carried forward to the next step without further purification. MS: 348.10 (M+H)$^+$.

Preparation of 1-(5-([1,2,4]triazolo[4,3-a]pyridin-6-yl)benzo[d]thiazol-2-yl)-3-ethylurea (IV-A)

Example 5

A solution of 6-bromo-[1,2,4]triazolo[4,3-a]pyridine (0.080 g, 0.40 mmol), 1-ethyl-3-(5-(4,4,5,5-tetramethyl-1,3,2-dioxaborolan-2-yl)benzo[d]thiazol-2-yl)urea III (0.21 g, 0.60 mmol) and K$_3$PO$_4$ (0.13 g, 0.60 mmol) in DMF-H$_2$O (7.0 mL, 2:1) was degassed by flushing with nitrogen for 15 min. Dichlorobis(triphenylphosphine)-palladium(II) (0.04 g, 0.05 mmol) was then added to the reaction mixture followed by degassing with nitrogen for another 15 min. The resulting reaction mixture was then heated to 80° C. for 16 h. After the completion of the reaction (TLC monitoring), the reaction mixture was cooled to room temperature and poured onto ice-cold water followed by extraction with EtOAc (2×50 mL). The combined organics was washed with brine, dried (Na$_2$SO$_4$), filtered and concentrated under reduced pressure. The crude was then purified over silica gel (230-400 M, 3.50% MeOH-DCM) to obtain the desired product (0.003 g, 2%). $^1$H-NMR (400 MHz, DMSO-d$_6$): δ 1.11 (t, J=7.20 Hz, 3H), 3.19 (m, 2H), 6.72 (br s, 1H), 7.55 (dd, J=1.60 and 8.40 Hz, 1H), 7.80-7.96 (m, 3H), 8.02 (d, J=8.0 Hz, 1H), 8.97 (s, 1H), 9.25 (s, 1H) and 10.82 (br s, 1H). MS: 339.24 (M+H)$^+$. Qualitative HPLC Purity (Acquity BEH C-18, 100×2.1 mm, 255 nm): 99.03% (Rt=4.63 min).

Preparation of 1-ethyl-3-(5-(imidazo[1,2-a]pyridin-6-yl)benzo[d]thiazol-2-yl)urea (IV-B)

Example 6

A solution of 6-bromoimidazo[1,2-A]pyridine (0.062 g, 0.32 mmol), 1-ethyl-3-(5-(4,4,5,5-tetramethyl-1,3,2-dioxaborolan-2-yl)benzo[d]thiazol-2-yl)urea III (0.10 g, 0.29 mmol) and K$_3$PO$_4$ (0.07 g, 0.34 mmol) in DMF-H$_2$O (6.0 mL, 2:1) was degassed by flushing with nitrogen for 15 min. Dichlorobis(triphenylphosphine)-palladium(II) (0.01 g, 0.014 mmol) was then added to the reaction mixture followed by degassing with nitrogen for another 15 min. The resulting reaction mixture was then heated to 100° C. for 4 h. After the completion of the reaction (TLC monitoring), the reaction mixture was cooled to room temperature and poured onto ice-cold water followed by extraction with EtOAc (2×50 mL). The combined organics was washed with brine, dried (Na$_2$SO$_4$), filtered and concentrated under reduced pressure. The crude was then purified over silica gel (100-200 M, 2.0% MeOH-DCM) to obtain the desired product (0.014 g, 14%). $^1$H-NMR (400 MHz, DMSO-d$_6$): δ 1.11 (t, J=7.20 Hz, 3H), 3.19 (m, 2H), 6.78 (br s, 1H), 7.54-7.65 (m, 4H), 7.93-7.99 (m, 3H), 8.99 (s, 1H) and 10.82 (br s, 1H). MS: 338.24 (M+H)$^+$. Qualitative HPLC Purity (Acquity BEH C-18, 100×2.1 mm, 257 nm): 94.35% (Rt=4.78 min).

Preparation of 1-ethyl-3-(5-(tetrazolo[1,5-a]pyridin-6-yl)benzo[d]thiazol-2-yl)urea (IV-C)

Example 7

A solution of 6-bromotetrazolo[1,5-A]pyridine (0.05 g, 0.24 mmol), 1-ethyl-3-(5-(4,4,5,5-tetramethyl-1,3,2-dioxaborolan-2-yl)benzo[d]thiazol-2-yl)urea III (0.08 g, 0.22 mmol) and K$_3$PO$_4$ (0.054 g, 0.25 mmol) in DMF-H$_2$O (6.0 mL, 2:1) was degassed by flushing with nitrogen for 15 min. Dichlorobis(triphenylphosphine)-palladium(II) (0.007 g, 0.009 mmol) was then added to the reaction mixture followed by degassing with nitrogen for another 15 min. The resulting reaction mixture was then heated to 80° C. for 3 h. After the completion of the reaction (TLC monitoring), the reaction mixture was cooled to room temperature and poured onto ice-cold water followed by extraction with EtOAc (2×50 mL). The combined organics was washed with brine, dried (Na$_2$SO$_4$), filtered and concentrated under reduced pressure. The crude was then purified over silica gel (100-200 M, 2.0% MeOH-DCM) to obtain the desired product (0.003 g, 4%). $^1$H-NMR (400 MHz, DMSO-d$_6$): δ 1.10 (t, J=7.20 Hz, 3H), 3.20 (m, 2H), 6.75 (br s, 1H), 7.72 (d, J=8.0 Hz, 1H), 8.06 (d, J=8.40 Hz, 1H), 8.12 (s, 1H), 8.29 (m, 2H), 9.75 (s, 1H) and 10.82 (br s, 1H). MS: 338.03 (M+H)$^+$. Qualitative HPLC Purity (Acquity BEH C-18, 100×2.1 mm, 254 nm): 98.57% (Rt=4.95 min).

Preparation of 1-(5-(3,4-dihydro-2H-pyrido[3,2-b][1, 4]oxazin-7-yl)benzo[d]thiazol-2-yl)-3-ethylurea (IV-D)

Example 8

A solution of 6-bromotetrazolo[1,5-A]pyridin7-bromo-3,4-dihydro-2H-pyrido[3,2-B][1,4]oxazine (0.10 g, 0.46 mmol), 1-ethyl-3-(5-(4,4,5,5-tetramethyl-1,3,2-dioxaborolan-2-yl)benzo[d]thiazol-2-yl)urea III (0.16 g, 0.46 mmol) and K$_3$PO$_4$ (0.20 g, 0.93 mmol) in DMF-H$_2$O (6.0 mL, 2:1) was degassed by flushing with nitrogen for 15 min. Dichlorobis(triphenylphosphine)-palladium(II) (0.033 g, 0.04 mmol) was then added to the reaction mixture followed by degassing with nitrogen for another 15 min. The resulting reaction mixture was then heated to 80° C. for 2 h. After the completion of the reaction (TLC monitoring), the reaction mixture was cooled to room temperature and poured onto ice-cold water followed by extraction with EtOAc (2×50 mL). The combined organics was washed with brine, dried (Na$_2$SO$_4$), filtered and concentrated under reduced pressure. The crude was then purified over silica gel (100-200 M, 3.0% MeOH-DCM) to obtain the desired product (0.012 g, 7%). $^1$H-NMR (400 MHz, DMSO-d$_6$): δ 1.11 (t, J=7.20 Hz, 3H), 3.20 (m, 2H), 3.43 (br s, 2H), 4.03 (m, 2H), 6.78 (br s, 1H), 6.85 (br s, 1H), 7.29 (s, 1H), 7.42 (d, J=8.40 Hz, 1H), 7.75 (s, 1H), 7.87 (d, J=8.40 Hz, 1H), 7.95 (d, J=1.20 Hz, 1H) and 10.71 (br s, 1H). MS: 356.19 (M+H)⁺. Qualitative HPLC Purity (Acquity BEH C-18, 100×2.1 mm, 235 nm): 87.51% (Rt=4.99 min).

Preparation of 1-ethyl-3-(5-(6-(hydroxymethyl)pyridin-3-yl)benzo[d]thiazol-2-yl)urea (IV-E)

Example 9

A solution of 5-bromo-2-hydroxymethyl pyridine (0.054 g, 0.29 mmol), 1-ethyl-3-(5-(4,4,5,5-tetramethyl-1,3,2-dioxaborolan-2-yl)benzo[d]thiazol-2-yl)urea III (0.10 g, 0.29 mmol) and K$_3$PO$_4$ (0.09 g, 0.43 mmol) in DMF-H$_2$O (5.0 mL, 3:2) was degassed by flushing with nitrogen for 15 min. Dichlorobis(triphenylphosphine)-palladium(II) (0.02 g, 0.03 mmol) was then added to the reaction mixture followed by degassing with nitrogen for another 15 min. The resulting reaction mixture was then heated to 85° C. for 4 h. After the completion of the reaction (TLC monitoring), the reaction mixture was cooled to room temperature and poured onto ice-cold water followed by extraction with EtOAc (2×50 mL). The combined organics was washed with brine, dried (Na$_2$SO$_4$), filtered and concentrated under reduced pressure. The crude was then purified over silica gel (100-200 M, 2.50% MeOH-DCM) to obtain the desired product (0.007 g, 5%). $^1$H-NMR (400 MHz, DMSO-d$_6$): δ 1.11 (t, J=7.20 Hz, 3H), 3.19 (m, 2H), 4.62 (d, J=6.0 Hz, 2H), 5.46 (t, J=5.60 Hz, 1H), 6.75 (br s, 1H), 7.56 (d, J=8.40 Hz, 2H), 7.93 (s, 1H), 7.99 (d, J=8.0 Hz, 1H), 8.15 (dd, J=2.0 and 8.0 Hz, 1H), 8.84 (s, 1H) and 10.76 (br s, 1H). MS: 329.25 (M+H)⁺. Qualitative HPLC Purity (Acquity BEH C-18, 100×2.1 mm, 254 nm): 97.81% (Rt=4.52 min).

Preparation of 1-ethyl-3-(5-(5-(2-oxopyridin-1(2H)-yl)pyrazin-2-yl)benzo[d]thiazol-2-yl)urea (IV-F)

Example 10

A solution of 2-bromo-5-(1H-pyridin-2-one)pyrazine (0.03 g, 0.12 mmol), 1-ethyl-3-(5-(4,4,5,5-tetramethyl-1,3,2-dioxaborolan-2-yl)benzo[d]thiazol-2-yl)urea III (0.082 g, 0.24 mmol) and K$_3$PO$_4$ (0.04 g, 0.18 mmol) in DMF-H$_2$O (9.0 mL, 2:1) was degassed by flushing with nitrogen for 15 min. Dichlorobis(triphenylphosphine)-palladium(II) (0.009 g, 0.012 mmol) was then added to the reaction mixture followed by degassing with nitrogen for another 15 min. The resulting reaction mixture was then heated to 80° C. for 4 h. After the completion of the reaction (TLC monitoring), the reaction mixture was cooled to room temperature and poured onto ice-cold water followed by extraction with EtOAc (2×50 mL). The combined organics was washed with brine, dried (Na$_2$SO$_4$), filtered and concentrated under reduced pressure. The crude was then purified over silica gel (100-200 M, 2.50% MeOH-DCM) to obtain the desired product (0.012 g, 26%). $^1$H-NMR (400 MHz, DMSO-d$_6$): δ 1.10 (t, J=7.20 Hz, 3H), 3.20 (m, 2H), 6.46 (t, J=7.20 Hz, 1H), 6.59 (d, J=9.20 Hz, 1H), 6.72 (br s, 1H), 7.60 (m, 1H), 7.95 (m, 1H), 8.06 (s, 2H), 8.43 (s, 1H), 9.15 (s, 1H), 9.38 (s, 1H) and 10.87 (br s, 1H). MS: 393.20 (M+H)⁺. Qualitative HPLC Purity (Acquity BEH C-18, 100×2.1 mm, 261 nm): 95.76% (Rt=4.94 min).

Preparation of 1-ethyl-3-(5-(2-(hydroxymethyl)-1-methyl-1H-imidazol-5-yl)benzo[d]thiazol-2-yl)urea (IV-G)

Example 11

A solution of 5-bromo-2-(hydroxymethyl)-1-methyl-1H-imidazole (0.06 g, 0.32 mmol), 1-ethyl-3-(5-(4,4,5,5-tetramethyl-1,3,2-dioxaborolan-2-yl)benzo[d]thiazol-2-yl)urea III (0.21 g, 0.64 mmol) and K$_3$PO$_4$ (0.10 g, 0.48 mmol) in DMF-H$_2$O (6.0 mL, 2:1) was degassed by flushing with nitrogen for 15 min. Dichlorobis(triphenylphosphine)-palladium(II) (0.023 g, 0.032 mmol) was then added to the reaction mixture followed by degassing with nitrogen for another 15 min. The resulting reaction mixture was then heated to 80° C. for 4 h. After the completion of the reaction (TLC monitoring), the reaction mixture was cooled to room temperature and poured onto ice-cold water followed by extraction with EtOAc (2×50 mL). The combined organics was washed with brine, dried (Na$_2$SO$_4$), filtered and concentrated under reduced pressure. The crude was then purified over silica gel (100-200 M, 3.0% MeOH-DCM) to obtain the desired product (0.007 g, 7%). $^1$H-NMR (400 MHz, DMSO-d$_6$): δ 1.11 (t, J=7.20 Hz, 3H), 3.19 (m, 2H), 3.66 (s, 3H), 4.56 (d, J=4.40 Hz, 2H), 5.36 (m, 1H), 6.77 (br s, 1H), 6.98 (s, 1H), 7.28 (d, J=8.40 Hz, 1H), 7.64 (s, 1H), 7.96 (d, J=8.0 Hz, 1H) and 10.74 (br s, 1H). MS: 332.11 (M+H)⁺. Qualitative HPLC Purity (Acquity BEH C-18, 100×2.1 mm, 256 nm): 94.64% (Rt=4.25 min).

Scheme-6:

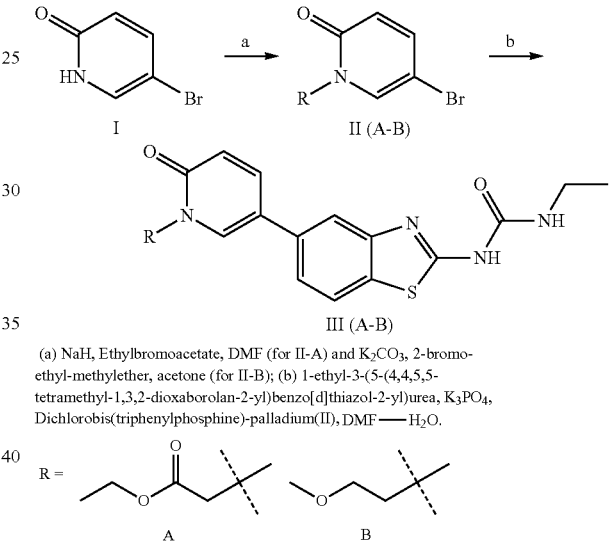

(a) NaH, Ethylbromoacetate, DMF (for II-A) and K$_2$CO$_3$, 2-bromo-ethyl-methylether, acetone (for II-B); (b) 1-ethyl-3-(5-(4,4,5,5-tetramethyl-1,3,2-dioxaborolan-2-yl)benzo[d]thiazol-2-yl)urea, K$_3$PO$_4$, Dichlorobis(triphenylphosphine)-palladium(II), DMF—H$_2$O.

Preparation of ethyl 2-(5-bromo-2-oxopyridin-1(2H)-yl)acetate (II-A)

To an ice-cold solution of 5-bromo-2(1H)-pyridone (1.0 g, 5.75 mmol) in DMF (5.0 mL) was added NaH (60% suspension in mineral oil, 0.25 g, 10.30 mmol) portion wise and the resulting solution was heated to 80° C. for 90 min. The reaction mixture was then again cooled to 0° C. followed by addition ethyl bromoacetate (1.92 g, 11.50 mmol). The reaction mixture was then heated to 80° C. for 16 h. After the completion of reaction (TLC monitoring), DMF was distilled off, added water and extracted with EtOAc (3×100 mL). The combined organics was dried over anhydrous Na$_2$SO$_4$, filtered and concentrated. The crude residue was purified over silica gel (100-200 M, 20% EtOAc-hexane) to obtain the desired product (0.90 g, 60%). MS: 260.10 (M+H)⁺.

Preparation of 5-bromo-1-(2-methoxyethyl)pyridin-2(1H)-one (II-B)

To a solution of 5-bromo-2(1H)-pyridone (0.10 g, 0.57 mmol) in acetone (5.0 ml) was added K$_2$CO$_3$ (0.18 g, 2.60 mmol followed by addition of 2-bromo-ethyl-methylether (0.24 g, 1.70 mmol). The resulting reaction mixture was heated to 60° C. for 16 h. After the completion of reaction (TLC monitoring), acetone was distilled off, added water and extracted with DCM (3×10 mL). The combined organics was washed with brine, dried ($Na_2SO_4$), filtered and concentrated. The crude residue was purified over silica gel (60-120 M, 1% MeOH-DCM) to obtain the desired product (0.10 g, 75%). MS: 232.01 $(M+H)^+$.

Preparation of ethyl 2-(5-(2-(3-ethylureido)benzo[d]thiazol-5-yl)-2-oxopyridin-1(2H)-yl)acetate (III-A)

Example 12

A solution of 1-ethyl-3-(5-(4,4,5,5-tetramethyl-1,3,2-dioxaborolan-2-yl)benzo[d]thiazol-2-yl)urea (0.20 g, 0.58 mmol), ethyl 2-(5-bromo-2-oxopyridin-1(2H)-yl)acetate II-A (0.30 g, 1.16 mmol) and $K_3PO_4$ (0.23 g, 1.08 mmol) in DMF-$H_2O$ (7.0 mL, 5:2) was degassed by flushing with nitrogen for 15 min. Dichlorobis(triphenylphosphine)-palladium (II) (0.02 g, 0.03 mmol) was then added to the reaction mixture followed by degassing with nitrogen for another 15 min. The resulting reaction mixture was then heated to 80° C. for 45 min. After the completion of the reaction (TLC monitoring), the reaction mixture was cooled to room temperature and poured onto ice-cold water followed by extraction with EtOAc (2×50 mL). The combined organics was washed with brine, dried ($Na_2SO_4$), filtered and concentrated under reduced pressure. The crude was then purified over silica gel (100-200 M, 4% MeOH-DCM) to obtain the desired product (0.02 g, 9%). $^1$H-NMR (400 MHz, DMSO-$d_6$): δ 1.10 (t, J=7.20 Hz, 3H), 1.22 (t, J=7.20 Hz, 3H), 3.20 (m, 2H), 4.17 (q, J=7.20 Hz, 2H), 4.77 (s, 2H), 6.54 (d, J=9.20 Hz, 1H), 6.73 (br s, 1H), 7.41 (m, 1H), 7.79 (s, 1H), 7.93 (d, J=8.0 Hz, 1H), 7.98 (dd, J=2.80 and 9.60 Hz, 1H), 8.21 (s, 1H) and 10.77 (br s, 1H). MS: 401.23. Qualitative HPLC Purity (Acquity BEH C-18, 100×2.1 mm, 261 nm): 89.81% (Rt=4.89 min).

Preparation of 1-(5-(1-(2-ethoxyethyl)-6-oxo-1,6-dihydropyridin-3-yl)benzo[d]thiazol-2-yl)-3-ethylurea (III-B)

Example 13

A solution of 1-ethyl-3-(5-(4,4,5,5-tetramethyl-1,3,2-dioxaborolan-2-yl)benzo[d]thiazol-2-yl)urea (0.30 g, 0.86 mmol), 5-bromo-1-(2-methoxyethyl)pyridin-2(1H)-one II-B (0.16 g, 0.65 mmol) and $K_3PO_4$ (0.21 g, 0.97 mmol) in DMF-$H_2O$ (7.0 mL, 5:2) was degassed by flushing with nitrogen for 15 min. Dichlorobis(triphenylphosphine)-palladium(II) (0.04 g, 0.065 mmol) was then added to the reaction mixture followed by degassing with nitrogen for another 15 min. The resulting reaction mixture was then heated to 85° C. for 15 h. After the completion of the reaction (TLC monitoring), the reaction mixture was cooled to room temperature and poured onto ice-cold water followed by extraction with DCM (2×50 mL). The combined organics was washed with brine, dried ($Na_2SO_4$), filtered and concentrated under reduced pressure. The crude was then purified over silica gel (100-200 M, 2% MeOH-DCM) to obtain the desired product (0.064 g, 19%). $^1$H-NMR (400 MHz, DMSO-$d_6$): δ 1.09 (t, J=7.20 Hz, 3H), 3.20 (m, 2H), 3.25 (s, 3H), 3.62 (t, J=5.20 Hz, 2H), 4.15 (t, J=5.60 Hz, 2H), 6.50 (d, J=9.60 Hz, 1H), 6.72 (br s, 1H), 7.41 (m, 1H), 7.79 (s, 1H), 7.87-7.92 (m, 2H), 8.07 (d, J=2.40 Hz, 1H) and 10.72 (br s, 1H). MS: 371.10 $(M+H)^+$. Qualitative HPLC Purity (Acquity BEH C-18, 100×2.1 mm, 262 nm): 81.75% (Rt=4.61 min).

Scheme-7:

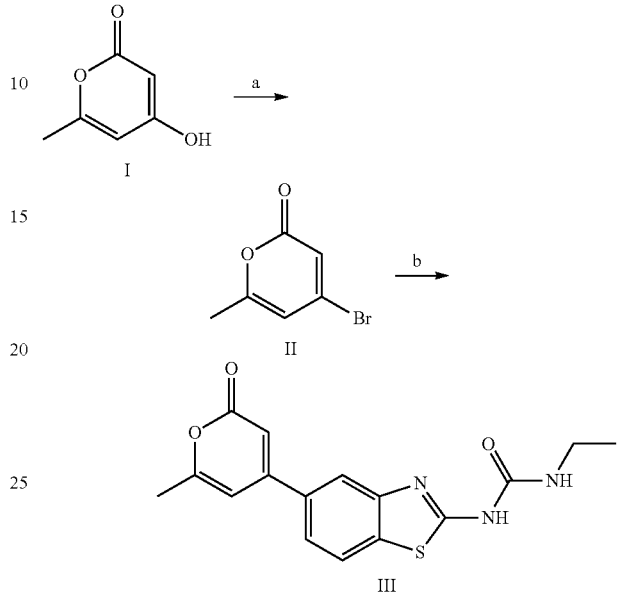

(a) $P_2O_5$, TBAB, toluene, 100° C., 2 h; (b) 1-ethyl-3-(5-(4,4,5,5-tetramethyl-1,3,2-dioxaborolan-2-yl)benzo[d]thiazol-2-yl)urea, $K_3PO_4$, Dichlorobis(triphenylphosphine)-palladium(II), DMF——$H_2O$.

Preparation of 4-bromo-6-methyl-2H-pyran-2-one (II)

To a solution of 4-hydroxy-6-methyl-2-pyrone (0.20 g, 1.60 mmol) in toluene (5.0 ml) was added $P_2O_5$ (0.56 g, 4.0 mmo) and TBAB (0.62 g, 1.90 mmol) under nitrogen atmosphere. The resultant reaction mixture was heated to 100° C. for 2 h. After the completion of reaction (TLC monitoring), the reaction mixture was cooled to room temperature and filtered. The filtrate was washed with 5% $NaHCO_3$ solution and dried over anhydrous $Na_2SO_4$, filtered and concentrated to obtain the desired product (0.18 g, 60%). MS: 189.10 $(M+H)^+$.

Preparation of 1-ethyl-3-(5-(6-methyl-2-oxo-2H-pyran-4-yl)benzo[d]thiazol-2-yl)urea (III)

Example 14

A solution of 4-bromo-6-methyl-2H-pyran-2-one II (0.18 g, 0.95 mmol), 1-ethyl-3-(5-(4,4,5,5-tetramethyl-1,3,2-dioxaborolan-2-yl)benzo[d]thiazol-2-yl)urea (0.50 g, 1.43 mmol) and $K_3PO_4$ (0.30 g, 1.43 mmol) in DMF-$H_2O$ (6.0 mL, 2:1) was degassed by flushing with nitrogen for 15 min. Dichlorobis(triphenylphosphine)-palladium(II) (0.07 g, 0.095 mmol) was then added to the reaction mixture followed by degassing with nitrogen for another 15 min. The resulting reaction mixture was then heated to 80° C. for 4 h. After the completion of the reaction (TLC monitoring), the reaction mixture was cooled to room temperature and poured onto ice-cold water followed by extraction with EtOAc (2×50 mL). The combined organics was washed with brine, dried ($Na_2SO_4$), filtered and concentrated under reduced pressure.

The crude was then purified over silica gel (230-400 M, 1.20% MeOH-DCM) to obtain the desired product (0.15 g, 50%). $^1$H-NMR (400 MHz, DMSO-$d_6$): δ 1.09 (t, J=7.20 Hz, 3H), 2.30 (s, 3H), 3.19 (m, 2H), 6.56 (s, 1H), 6.72 (br s, 1H), 6.84 (s, 1H), 7.64 (d, J=8.40 Hz, 1H), 8.0-8.03 (m, 2H) and 10.81 (br s, 1H). MS: 330.18 (M+H)$^+$. Qualitative HPLC Purity (Acquity BEH C-18, 100×2.1 mm, 238 nm): 97.55% (Rt=5.13 min).

Scheme-8:

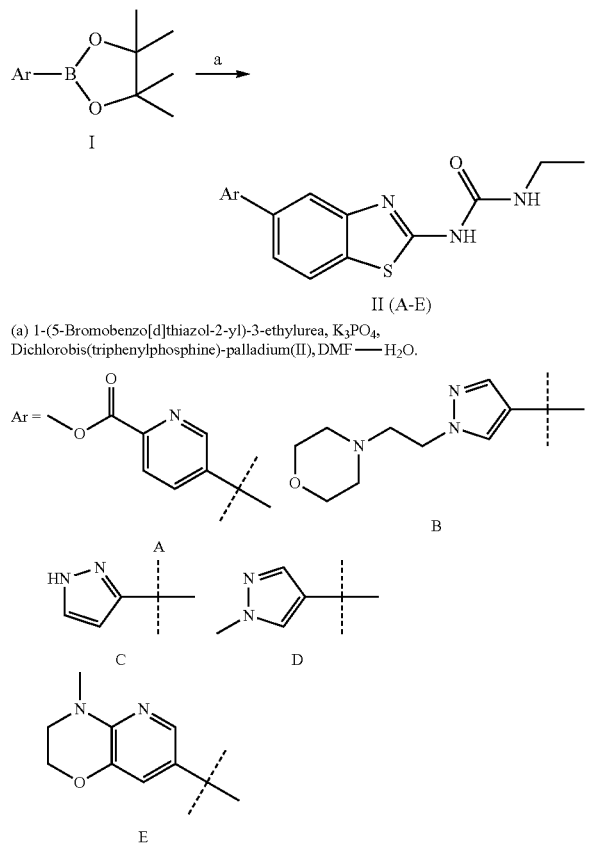

(a) 1-(5-Bromobenzo[d]thiazol-2-yl)-3-ethylurea, $K_3PO_4$, Dichlorobis(triphenylphosphine)-palladium(II), DMF——$H_2O$.

Preparation of methyl 5-(2-(3-ethylureido)benzo[d]thiazol-5-yl)picolinate (II-A)

Example 15

A solution of 2-methoxycarbonyl-5-pyridineboronic acid, pinacol ester (0.20 g, 0.75 mmol), 1-(5-bromobenzo[d]thiazol-2-yl)-3-ethylurea (0.15 g, 0.50 mmol) and $K_3PO_4$ (0.21 g, 1.0 mmol) in DMF-$H_2O$ (7.0 mL, 5:2) was degassed by flushing with nitrogen for 15 min. Dichlorobis(triphenylphosphine)-palladium(II) (0.03 g, 0.05 mmol) was then added to the reaction mixture followed by degassing with nitrogen for another 15 min. The resulting reaction mixture was then heated to 80° C. for 16 h. After the completion of the reaction (TLC monitoring), the reaction mixture was cooled to room temperature and poured onto ice-cold water followed by extraction with EtOAc (2×50 mL). The combined organics was washed with brine, dried ($Na_2SO_4$), filtered and concentrated under reduced pressure. The crude was then purified over silica gel (100-200 M, 100% EtOAc) to obtain the desired product (0.01 g, 6%). $^1$H-NMR (400 MHz, DMSO-$d_6$): δ 1.09 (t, J=7.20 Hz, 3H), 3.19 (m, 2H), 3.91 (s, 3H), 6.75 (br s, 1H), 7.66 (d, J=9.60 Hz, 1H), 8.05 (m, 2H), 8.14 (d, J=8.40 Hz, 1H), 8.36 (m, 1H), 9.11 (s, 1H) and 10.78 (br s, 1H). MS: 357.15 (M+H)$^+$. Qualitative HPLC Purity (Acquity BEH C-18, 100×2.1 mm, 266 nm): 92.29% (Rt=4.99 min).

Preparation of 1-ethyl-3-(5-(1-(2-morpholinoethyl)-1H-pyrazol-4-yl)benzo[d]thiazol-2-yl)urea (II-B)

Example 16

A solution of 1-(2-morpholinoethyl)-1H-pyrazole-4-boronicacid, pinacol ester (0.08 g, 0.25 mmol), 1-(5-bromobenzo[d]thiazol-2-yl)-3-ethylurea (0.05 g, 0.16 mmol) and $K_3PO_4$ (0.053 g, 0.25 mmol) in DMF-$H_2O$ (3.0 mL, 2:1) was degassed by flushing with nitrogen for 15 min. Dichlorobis(triphenylphosphine)-palladium(II) (0.012 g, 0.016 mmol) was then added to the reaction mixture followed by degassing with nitrogen for another 15 min. The resulting reaction mixture was then heated to 80° C. for 2 h. After the completion of the reaction (TLC monitoring), the reaction mixture was cooled to room temperature and poured onto ice-cold water followed by extraction with EtOAc (2×25 mL). The combined organics was washed with brine, dried ($Na_2SO_4$), filtered and concentrated under reduced pressure. The crude was then purified over silica gel (100-200 M, 2% MeOH-DCM) to obtain the desired product (0.015 g, 23%). $^1$H-NMR (400 MHz, DMSO-$d_6$): δ 1.10 (t, J=7.20 Hz, 3H), 2.42 (br s, 4H), 2.74 (t, J=6.80 Hz, 2H), 3.20 (quintet, J=6.80 Hz, 2H), 3.55 (m, 4H), 4.23 (t, J=6.40 Hz, 2H), 6.72 (br s, 1H), 7.43 (d, J=8.0 Hz, 1H), 7.79-7.83 (m, 2H), 7.92 (s, 1H), 8.23 (s, 1H) and 10.66 (br s, 1H). MS: 401.22 (M+H)$^+$. Qualitative HPLC Purity (Acquity BEH C-18, 100×2.1 mm, 254 nm): 98.63% (Rt=4.68 min).

Preparation of 1-(5-(1H-pyrazol-3-yl)benzo[d]thiazol-2-yl)-3-ethylurea (II-C)

Example 17

A solution of 1H-pyrazole-3-boronic acid, pinacol ester (0.072 g, 0.37 mmol), 1-(5-bromobenzo[d]thiazol-2-yl)-3-ethylurea (0.075 g, 0.25 mmol) and $K_3PO_4$ (0.11 g, 0.50 mmol) in DMF-$H_2O$ (6.0 mL, 2:1) was degassed by flushing with nitrogen for 15 min. Dichlorobis(triphenylphosphine)-palladium(II) (0.017 g, 0.025 mmol) was then added to the reaction mixture followed by degassing with nitrogen for another 15 min. The resulting reaction mixture was then heated to 80° C. for 16 h. After the completion of the reaction (TLC monitoring), the reaction mixture was cooled to room temperature and poured onto ice-cold water followed by extraction with EtOAc (2×25 mL). The combined organics was washed with brine, dried ($Na_2SO_4$), filtered and concentrated under reduced pressure. The crude was then purified over silica gel (100-200 M, 80% EtOAc-Hexane) to obtain the desired product (0.001 g, 14%). $^1$H-NMR (400 MHz, DMSO-$d_6$): δ 1.09 (t, J=7.20 Hz, 3H), 3.19 (m, 2H), 6.77 (m, 2H), 7.48 (m, 1H), 7.59 (d, J=8.0 Hz, 1H), 7.78 (s, 1H), 7.87 (d, J=7.20 Hz, 1H), 8.02 (s, 1H) and 10.82 (br s, 1H). MS: 288.10 (M+H)$^+$. Qualitative HPLC Purity (Acquity BEH C-18, 100×2.1 mm, 252 nm): 93.64% (Rt=4.66 min).

Preparation of 1-ethyl-3-(5-(1-methyl-1H-pyrazol-4-yl)benzo[d]thiazol-2-yl)urea (II-D)

Example 18

A solution of 1-methylpyrazole-4-boronic acid, pinacol ester (0.10 g, 0.38 mmol), 1-(5-bromobenzo[d]thiazol-2-yl)-

3-ethylurea (0.075 g, 0.25 mmol) and K$_3$PO$_4$ (0.16 g, 0.75 mmol) in DMF-H$_2$O (6.0 mL, 2:1) was degassed by flushing with nitrogen for 15 min. Dichlorobis(triphenylphosphine)-palladium(II) (0.018 g, 0.03 mmol) was then added to the reaction mixture followed by degassing with nitrogen for another 15 min. The resulting reaction mixture was then heated to 80° C. for 2 h. After the completion of the reaction (TLC monitoring), the reaction mixture was cooled to room temperature and poured onto ice-cold water followed by extraction with EtOAc (2×25 mL). The combined organics was washed with brine, dried (Na$_2$SO$_4$), filtered and concentrated under reduced pressure. The crude was then purified over silica gel (100-200 M, 2.50% MeOH-DCM) to obtain the desired product (0.015 g, 20%). $^1$H-NMR (400 MHz, DMSO-d$_6$): δ 1.09 (t, J=7.20 Hz, 3H), 3.20 (m, 2H), 3.86 (s, 3H), 6.71 (br s, 1H), 7.42 (d, J=8.40 Hz, 1H), 7.80 (m, 2H), 7.91 (s, 1H), 8.18 (s, 1H) and 10.66 (br s, 1H). MS: 302.17. Qualitative HPLC Purity (Acquity BEH C-18, 100×2.1 mm, 253 nm): 96.66% (Rt=4.76 min).

Preparation of 1-ethyl-3-(5-(4-methyl-3,4-dihydro-2H-pyrido[3,2-b][1,4]oxazin-7-yl)benzo[d]thiazol-2-yl)urea (II-E)

Example 19

A solution of 4-methyl-3,4-dihydro-2H-pyrido[3,2-B][1,4]oxazine-7-boronic acid, pinacol ester (0.096 g, 0.34 mmol), 1-(5-bromobenzo[d]thiazol-2-yl)-3-ethylurea (0.07 g, 0.23 mmol) and K$_3$PO$_4$ (0.097 g, 0.46 mmol) in DMF-H$_2$O (7.0 mL, 5:2) was degassed by flushing with nitrogen for 15 min. Dichlorobis(triphenylphosphine)-palladium(II) (0.016 g, 0.023 mmol) was then added to the reaction mixture followed by degassing with nitrogen for another 15 min. The resulting reaction mixture was then heated to 85° C. for 2 h. After the completion of the reaction (TLC monitoring), the reaction mixture was cooled to room temperature and poured onto ice-cold water followed by extraction with EtOAc (2×25 mL). The combined organics was washed with brine, dried (Na$_2$SO$_4$), filtered and concentrated under reduced pressure. The crude was then purified over silica gel (100-200 M, 2.50% MeOH-DCM) to obtain the desired product (0.05 g, 59%). $^1$H-NMR (400 MHz, DMSO-d$_6$): δ 1.09 (t, J=7.20 Hz, 3H), 3.06 (s, 3H), 3.20 (m, 2H), 3.46 (t, J=4.40 Hz, 2H), 4.25 (t, J=4.0 Hz, 2H), 6.74 (br s, 1H), 7.29 (d, J=1.60 Hz, 1H), 7.43 (d, J=8.40 Hz, 1H), 7.77 (br s, 1H), 7.88 (d, J=8.0 Hz, 1H), 8.06 (d. J=1.60 Hz, 1H), and 10.68 (br s, 1H). MS: 370.21. Qualitative HPLC Purity (Acquity BEH C-18, 100×2.1 mm, 236 nm): 95.95% (Rt=5.22 min).

Scheme-9:

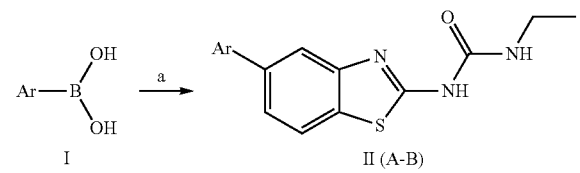

(a) 1-(5-Bromobenzo[d]thiazol-2-yl)-3-ethylurea, K$_3$PO$_4$, Dichlorobis(triphenylphosphine)-palladium(II), DMF—H$_2$O.

Ar =

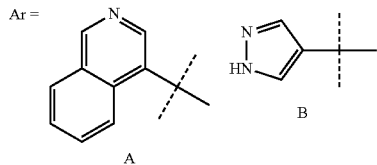

Preparation of 1-ethyl-3-(5-(isoquinolin-4-yl)benzo[d]thiazol-2-yl)urea (II-A)

Example 20

A solution of 4-isoquinolineboronic acid (0.052 g, 0.30 mmol), 1-(5-bromobenzo[d]thiazol-2-yl)-3-ethylurea (0.075 g, 0.25 mmol) and K$_3$PO$_4$ (0.08 g, 0.37 mmol) in DMF-H$_2$O (3.0 mL, 2:1) was degassed by flushing with nitrogen for 15 min. Dichlorobis(triphenylphosphine)-palladium(II) (0.01 g, 0.015 mmol) was then added to the reaction mixture followed by degassing with nitrogen for another 15 min. The resulting reaction mixture was then heated to 95° C. for 2 h. After the completion of the reaction (TLC monitoring), the reaction mixture was cooled to room temperature and poured onto ice-cold water followed by extraction with DCM (2×50 mL). The combined organics was washed with brine, dried (Na$_2$SO$_4$), filtered and concentrated under reduced pressure. The crude was then purified over silica gel (100-200 M, 3% MeOH-DCM) to obtain the desired product (0.04 g, 46%). $^1$H-NMR (400 MHz, DMSO-d$_6$): δ 1.10 (t, J=7.20 Hz, 3H), 3.20 (quintet, J=6.80 Hz, 2H), 6.75 (br s, 1H), 7.37 (d, J=9.20 Hz, 1H), 7.72-7.81 (m, 3H), 7.89 (d, J=8.0 Hz, 1H), 8.07 (d, J=8.0 Hz, 1H), 8.24 (d, J=8.0 Hz, 1H), 8.49 (s, 1H), 9.36 (s, 1H) and 10.80 (br s, 1H). MS: 349.14. Qualitative HPLC Purity (Acquity BEH C-18, 100×2.1 mm, 218 nm): 98.45% (Rt=5.50 min).

Preparation of 1-(5-(1H-pyrazol-4-yl)benzo[d]thiazol-2-yl)-3-ethylurea (II-B)

Example 21

A solution of 1H-pyrazole-4-boronic acid (0.037 g, 0.33 mmol), 1-(5-bromobenzo[d]thiazol-2-yl)-3-ethylurea (0.05 g, 0.17 mmol) and K$_3$PO$_4$ (0.11 g, 0.49 mmol) in DMF-H$_2$O (6.0 mL, 2:1) was degassed by flushing with nitrogen for 15 min. Dichlorobis(triphenylphosphine)-palladium(II) (0.011 g, 0.016 mmol) was then added to the reaction mixture followed by degassing with nitrogen for another 15 min. The resulting reaction mixture was then heated to 80° C. for 16 h. After the completion of the reaction (TLC monitoring), the reaction mixture was cooled to room temperature and poured onto ice-cold water followed by extraction with DCM (2×25 mL). The combined organics was washed with brine, dried (Na$_2$SO$_4$), filtered and concentrated under reduced pressure. The crude was then purified over silica gel (100-200 M, 3% MeOH-DCM) to obtain the desired product (0.01 g, 21%). $^1$H-NMR (400 MHz, DMSO-d$_6$): δ 1.09 (t, J=7.20 Hz, 3H), 3.18 (quintet, J=6.80 Hz, 2H), 6.76 (br s, 1H), 7.48 (dd, J=1.60 and 8.40 Hz, 1H), 7.66 (br s, 1H), 7.82 (m, 2H), 8.11 (br s, 1H), 8.24 (br s, 1H) and 10.67 (br s, 1H). MS: 288.20. Qualitative HPLC Purity (Acquity BEH C-18, 100×2.1 mm, 251 nm): 96.91% (Rt=4.52 min).

Scheme-10:

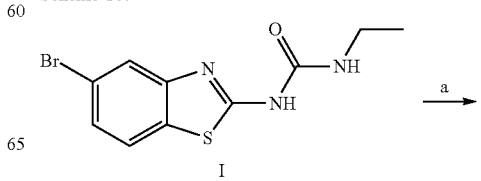

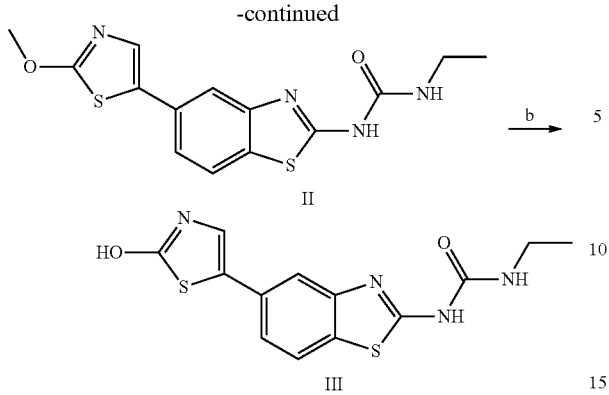

(a) 2-Methoxy-5-(tributylstannyl)thiazole, Pd(PPh₃)₄, DMF; (b) BBr₃—DCM.

Preparation of 1-ethyl-3-(5-(2-methoxythiazol-5-yl)benzo[d]thiazol-2-yl)urea (II)

Example 22

To a solution of 1-(5-bromobenzo[d]thiazol-2-yl)-3-ethylurea (0.05 g, 0.17 mmol) in DMF (5.0 mL) was added 2-methoxy-5-(tributylstannyl)thiazole (0.14 g, 0.33 mmol) and the resulting solution was degassed by nitrogen for 15 min. Tetarkis(triphenylphosphine)palladium(0) (0.02 g, 0.017 mmol) was then added to the solution that was again degassed by nitrogen for 15 min. The reaction mixture was then heated to 90° C. for 5 h. After the completion of reaction (TLC monitoring), the reaction mixture was cooled to room temperature and poured onto ice-cold water followed by extraction with EtOAc (3×50 mL). The combined organics was washed with brine, dried (Na₂SO₄), filtered and concentrated. The crude residue was purified over silica gel (230-400 M, 1.50% MeOH-DCM) to obtain the desired product (0.035 g, 63%). ¹H-NMR (400 MHz, DMSO-d₆): δ 1.08 (t, J=6.80 Hz, 3H), 3.20 (m, 2H), 4.05 (s, 3H), 6.72 (br s, 1H), 7.39 (d, J=8.0 Hz, 1H), 7.68 (s, 1H), 7.74 (s, 1H), 7.90 (d, J=8.0 Hz, 1H) and 10.76 (br s, 1H). MS: 335.09 (M+H)⁺. Qualitative HPLC Purity (Acquity BEH C-18, 100×2.1 mm, 268 nm): 97.44% (Rt=5.81 min).

Preparation of 1-ethyl-3-(5-(2-hydroxythiazol-5-yl)benzo[d]thiazol-2-yl)urea (III)

Example 23

To a solution of 1-ethyl-3-(5-(2-methoxythiazol-5-yl)benzo[d]thiazol-2-yl)urea II (0.025 g, 0.075 mmol) in DCM at −78° C. was added boron tribromide (71.0 μL, 0.75 mmol) and the resulting reaction mixture was allowed to come to room temperature over the period of 1-2 h. After the completion of reaction (TLC monitoring), the reaction mixture was cooled to −30° C. followed by quenching with ice-cold water and extraction with EtOAc (3×50 mL). The combined organics was washed with brine, dried (Na₂SO₄), filtered and concentrated. The crude residue was purified over silica gel (230-400 M, 2.10% MeOH-DCM) to obtain the desired product (0.07 g, 29%). ¹H-NMR (400 MHz, DMSO-d₆): δ 1.08 (t, J=7.20 Hz, 3H), 3.20 (m, 2H), 6.72 (br s, 1H), 7.30 (dd, J=1.60 and 8.0 Hz, 1H), 7.48 (s, 1H), 7.61 (s, 1H), 7.86 (d, J=8.40 Hz, 1H), 10.74 (br s, 1H) and 11.44 (br s, 1H). MS: 321.12 (M+H)⁺. Qualitative HPLC Purity (Acquity BEH C-18, 100×2.1 mm, 237 nm): 97.26% (Rt=4.68 min).

Scheme-11:

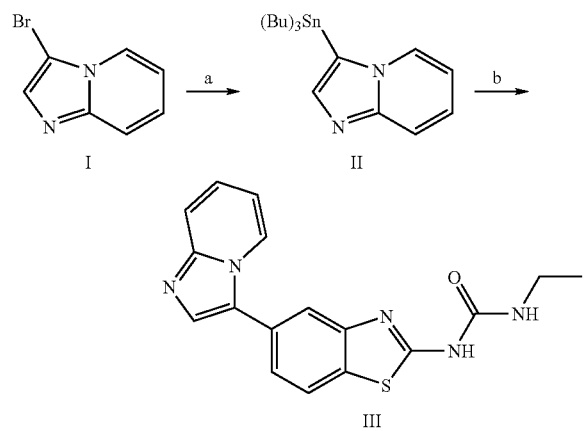

(a) n-BuLi, Tributyltin chloride, THF;
(b) 1-(5-bromobenzo[d]thiazol-2-yl)-3-ethylurea, Pd(PPh₃)₄, DMF.

Preparation of 3-(tributylstannyl)imidazo[1,2-a]pyridine (II)

A solution of 3-bromoimidazo[1,2-A]pyridine (0.10 g, 0.51 mmol) in THF (7.0 mL) under nitrogen atmosphere was cooled to −78° C. followed by dropwise addition of n-BuLi (1.30 M in hexane, 0.46 mL, 0.66 mmol). The resulting solution was stirred at same temperature for 45 min followed by addition of tributyltin chloride (0.14 mL, 0.53 mmol). The reaction mixture was then allowed to come to room temperature (45 min). After the completion of reaction (TLC monitoring), the reaction mixture was again cooled to −78° C. and quenched with dropwise addition of saturated NH₄Cl solution. The reaction mixture was then extracted with EtOAc (2×25 ml). The combined organics was dried (Na₂SO₄), filtered and concentrated. The residue was used as such without further purification. MS: 409.10 (M+H)⁺.

Preparation of 1-ethyl-3-(5-(imidazo[1,2-a]pyridin-3-yl)benzo[d]thiazol-2-yl)urea (III)

Example 24

To a solution of 1-(5-bromobenzo[d]thiazol-2-yl)-3-ethylurea (0.075 g, 0.25 mmol) in DMF (5.0 mL) was added 3-(tributylstannyl)imidazo[1,2-a]pyridine II (0.204 g, 0.50 mmol) and the resulting solution was degassed by nitrogen for 15 min. Tetarkis(triphenylphosphine)palladium(0) (0.03 g, 0.025 mmol) was then added to the solution that was again degassed by nitrogen for 15 min. The reaction mixture was then heated to 80° C. for 3 h. After the completion of reaction (TLC monitoring), the reaction mixture was cooled to room temperature and poured onto ice-cold water followed by extraction with EtOAc (2×50 mL). The combined organics was washed with brine, dried (Na₂SO₄), filtered and concentrated. The crude residue was purified over silica gel (100-200 M, 3% MeOH-DCM) to get the product that was repurified over prep-TLC to obtain the desired product (0.007 g, 8%). ¹H-NMR (400 MHz, DMSO-d₆): δ 1.10 (t, J=7.20 Hz, 3H), 3.20 (m, 2H), 6.76 (br s, 1H), 6.96 (t, J=6.80 Hz, 1H), 7.30 (m, 1H), 7.49 (dd, J=1.60 and 8.0 Hz, 1H), 7.65 (m, 1H), 7.79 (s, 1H), 7.89 (br s, 1H), 8.05 (d, J=8.0 Hz, 1H), 8.60 (d, J=6.80 Hz, 1H) and 10.77 (br s, 1H). MS: 338.18. Qualitative HPLC Purity (Acquity BEH C-18, 100×2.1 mm, 254 nm): 99.01% (Rt=5.0 min).

Scheme-12:

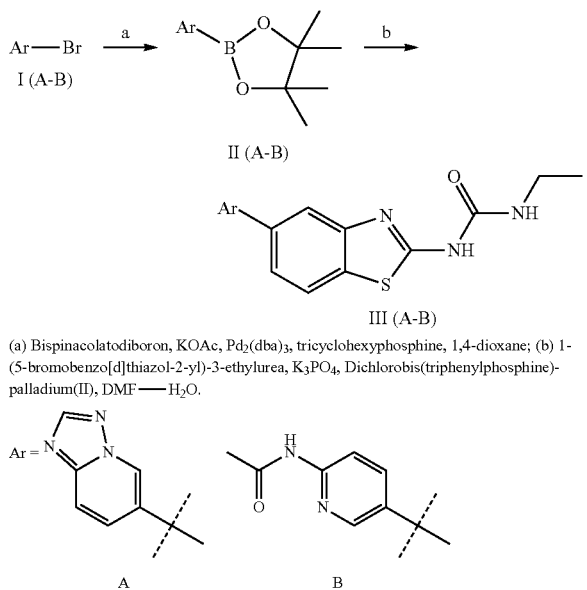

(a) Bispinacolatodiboron, KOAc, Pd₂(dba)₃, tricyclohexyphosphine, 1,4-dioxane; (b) 1-(5-bromobenzo[d]thiazol-2-yl)-3-ethylurea, K₃PO₄, Dichlorobis(triphenylphosphine)-palladium(II), DMF—H₂O.

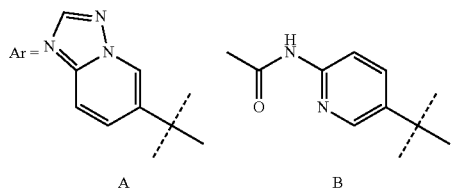

Preparation of 6-(4,4,5,5-tetramethyl-1,3,2-dioxaborolan-2-yl)-[1,2,4]triazolo[1,5-a]pyridine (II-A)

A solution of 6-bromo-[1,2,4]triazolo[1,5-a]pyridine (0.15 g, 0.75 mmol), bispinacolatodiboron (0.29 g, 1.14 mmol) and KOAc (0.11 g, 1.13 mmol) in 1,4-dioxane (5.0 mL) was degassed by flushing with nitrogen for 15 min. Tricyclohexylphosphine (0.025 g, 0.09 mmol) and tris(dibenzyledineacetone)dipalladium(0) (0.038 g, 0.037 mmol) was then added to the reaction mixture, which was again degassed by nitrogen for 15 min. The resulting reaction mixture was heated to 100° C. for 2 h. After the completion of the reaction (TLC monitoring), the reaction mixture was filtered through celite bed and the filtrate was concentrated to get the crude residue that was carried forward to the next step without further purification. MS: 246.10 (M+H)⁺.

Preparation of N-(5-(4,4,5,5-tetramethyl-1,3,2-dioxaborolan-2-yl)pyridin-2-yl)acetamide (II-B)

A solution of 2-acetylamino-5-bromopyridine (0.25 g, 0.95 mmol), bispinacolatodiboron (0.27 g, 1.04 mmol) and KOAc (0.14 g, 1.42 mmol) in 1,4-dioxane (8.0 mL) was degassed by flushing with nitrogen for 15 min. Tricyclohexylphosphine (0.032 g, 0.11 mmol) and tris(dibenzyledineacetone)dipalladium(0) (0.05 g, 0.047 mmol) was then added to the reaction mixture, which was again degassed by nitrogen for 15 min. The resulting reaction mixture was heated to 80° C. for 3 h. After the completion of the reaction (TLC monitoring), the reaction mixture was filtered through celite bed and the filtrate was concentrated to get the crude residue that was carried forward to the next step without further purification. MS: 263.15 (M+H)⁺.

Preparation of 1-(5-([1,2,4]triazolo[1,5-a]pyridin-6-yl)benzo[d]thiazol-2-yl)-3-ethylurea (III-A)

Example 25

A solution of 6-(4,4,5,5-tetramethyl-1,3,2-dioxaborolan-2-yl)-[1,2,4]triazolo[1,5-a]pyridine II-A (0.12 g, 0.49 mmol), 1-(5-bromobenzo[d]thiazol-2-yl)-3-ethylurea (0.10 g, 0.33 mmol) and K₃PO₄ (0.084 g, 0.39 mmol) in DMF-H₂O (7.0 mL, 5:2) was degassed by flushing with nitrogen for 15 min. Dichlorobis(triphenylphosphine)-palladium(II) (0.012 g, 0.016 mmol) was then added to the reaction mixture followed by degassing with nitrogen for another 15 min. The resulting reaction mixture was then heated to 85° C. for 2 h. After the completion of the reaction (TLC monitoring), the reaction mixture was cooled to room temperature and poured onto ice-cold water followed by extraction with DCM (2×50 mL). The combined organics was washed with brine, dried (Na₂SO₄), filtered and concentrated under reduced pressure. The crude was then purified over silica gel (60-120 M, 3% MeOH-DCM) to obtain the desired product (0.05 g, 45%). ¹H-NMR (400 MHz, DMSO-d₆): δ 1.10 (t, J=7.20 Hz, 3H), 3.20 (m, 2H), 6.73 (br s, 1H), 7.66 (d, J=8.0 Hz, 1H), 7.95 (d, J=9.20 Hz, 1H), 8.0-8.05 (m, 2H), 8.11 (d, J=9.60 Hz, 1H), 8.54 (s, 1H), 9.37 (s, 1H), 10.78 (br s, 1H). MS: 337.06 (M+H)⁺. Qualitative HPLC Purity (Acquity BEH C-18, 100×2.1 mm, 252 nm): 95.40% (Rt=4.78 min).

Preparation of N-(5-(2-(3-ethylureido)benzo[d]thiazol-5-yl)pyridin-2-yl)acetamide (III-B)

Example 26

A solution of N-(5-(4,4,5,5-tetramethyl-1,3,2-dioxaborolan-2-yl)pyridin-2-yl)acetamide II-B (0.13 g, 0.49 mmol), 1-(5-bromobenzo[d]thiazol-2-yl)-3-ethylurea (0.10 g, 0.33 mmol) and K₃PO₄ (0.084 g, 0.39 mmol) in DMF-H₂O (7.0 mL, 5:2) was degassed by flushing with nitrogen for 15 min. Dichlorobis(triphenylphosphine)-palladium(II) (0.023 g, 0.033 mmol) was then added to the reaction mixture followed by degassing with nitrogen for another 15 min. The resulting reaction mixture was then heated to 85° C. for 2 h. After the completion of the reaction (TLC monitoring), the reaction mixture was cooled to room temperature and poured onto ice-cold water followed by extraction with EtOAc (2×50 mL). The combined organics was washed with brine, dried (Na₂SO₄), filtered and concentrated under reduced pressure. The crude was then purified over silica gel (60-120 M, 2.50% MeOH-DCM) to obtain the desired product (0.057 g, 48%). ¹H-NMR (400 MHz, DMSO-d₆): δ 1.09 (t, J=7.20 Hz, 3H), 2.11 (s, 3H), 3.21 (m, 2H), 6.73 (br s, 1H), 7.55 (d, J=9.20 Hz, 1H), 7.92-7.97 (m, 2H), 8.15 (m, 2H), 8.68 (s, 1H), 10.58 (br s, 1H) and 10.74 (br s, 1H). MS: 354.09 (M+H)⁺. Qualitative HPLC Purity (Acquity BEH C-18, 100×2.1 mm, 264 nm): 93.67% (Rt=4.83 min).

Scheme-13:

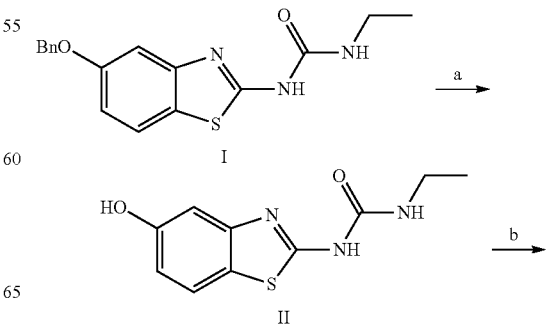

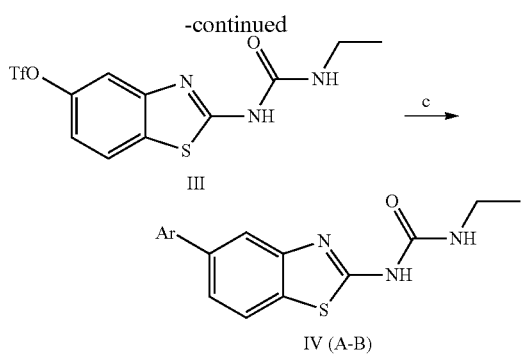

III

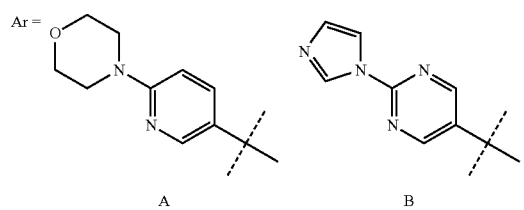

IV (A-B)

(a) Methanesulfonic acid, DCM; (b) N-phenylbis(trifluoromethanesulfonimide), DIPEA, DMF; (c) corresponding boronate, K₃PO₄, Dichlorobis(triphenylphosphine)-palladium(II), DMF—H₂O.

Ar =

A            B

Preparation of 1-ethyl-3-(5-hydroxybenzo[d]thiazol-2-yl)urea (II)

To a solution of 1-(5-(benzyloxy)benzo[d]thiazol-2-yl)-3-ethylurea I (1.20 g, 3.66 mmol) in DCM (100.0 mL) was added methanesulfonic acid (4.32 mL, 66.22 mmol) and the resulting reaction mixture was stirred at room temperature for 2 h. After the completion of reaction (TLC monitoring), the solvent was evaporated. The residue was cooled and then basified with saturated NaHCO₃ solution followed by extraction with EtOAc (3×100 mL). The combined organics was washed with brine, dried (Na₂SO₄), filtered and concentrated to obtain the desired product (0.90 g) that was carried forward to the next step without further purification. MS: 238.10 (M+H)⁺.

Preparation of 2-(3-ethylureido)benzo[d]thiazol-5-yl trifluoromethanesulfonate (III)

To a solution of 1-ethyl-3-(5-hydroxybenzo[d]thiazol-2-yl)urea II (2.30 g, 9.70 mmol) in DMF (100.0 mL) was added DIPEA (1.62 mL, 12.50 mmol) followed by addition of N-phenylbis(trifluoromethanesulfonimide) (3.81 g, 10.60 mmol). The resulting reaction mixture was stirred at room temperature for 2 h. After the completion of reaction (TLC monitoring), the solvent was evaporated, added water and extracted with hot EtOAc (2×100 mL). The combined organics was washed with brine, dried (Na₂SO₄), filtered and concentrated to obtain the desired product (1.30 g, 36%). MS: 370.10 (M+H)⁺.

Preparation of 1-ethyl-3-(5-(6-morpholinopyridin-3-yl)benzo[d]thiazol-2-yl)urea (IV-A)

Example 27

A solution of 2-(3-ethylureido)benzo[d]thiazol-5-yl trifluoromethanesulfonate III (0.075 g, 0.20 mmol), 4-(5-(4,4,5,5-tetramethyl-1,3,2-dioxaborolan-2-yl)pyridin-2-yl)morpholine (0.12 g, 0.40 mmol) and K₃PO₄ (0.13 g, 0.60 mmol) in DMF-H₂O (7.0 mL, 5:2) was degassed by flushing with nitrogen for 15 min. Dichlorobis(triphenylphosphine)-palladium(II) (0.014 g, 0.020 mmol) was then added to the reaction mixture followed by degassing with nitrogen for another 15 min. The resulting reaction mixture was then heated to 85° C. for 4 h. After the completion of the reaction (TLC monitoring), the reaction mixture was cooled to room temperature and poured onto ice-cold water followed by extraction with EtOAc (2×100 mL). The combined organics was washed with brine, dried (Na₂SO₄), filtered and concentrated under reduced pressure. The crude was then purified over silica gel (100-200 M, 3.5% MeOH-DCM) to obtain the desired product (0.040 g, 52%). ¹H-NMR (400 MHz, DMSO-d₆): δ 1.09 (t, J=7.20 Hz, 3H), 3.19 (m, 2H), 3.49 (t, J=5.20 Hz, 4H), 3.71 (t, J=4.80 Hz, 4H), 6.74 (br s, 1H), 6.94 (d, J=8.80 Hz, 1H), 7.47 (m, 1H), 7.83 (s, 1H), 7.89-7.95 (m, 2H), 8.52 (s, 1H) and 10.69 (br s, 1H). MS: 384.22 (M+H)⁺. Qualitative HPLC Purity (Acquity BEH C-18, 100×2.1 mm, 233 nm): 96.36% (Rt=5.43 min).

Preparation of 1-(5-(2-(1H-imidazol-1-yl)pyrimidin-5-yl)benzo[d]thiazol-2-yl)-3-ethylurea (IV-B)

Example 28

A solution of 2-(3-ethylureido)benzo[d]thiazol-5-yl trifluoromethanesulfonate III (0.075 g, 0.20 mmol), 2-(1H-imidazol-1-yl)-5-(4,4,5,5-tetramethyl-1,3,2-dioxaborolan-2-yl)pyrimidine (0.11 g, 0.40 mmol) and K₃PO₄ (0.13 g, 0.60 mmol) in DMF-H₂O (7.0 mL, 5:2) was degassed by flushing with nitrogen for 15 min. Dichlorobis(triphenylphosphine)-palladium(II) (0.014 g, 0.020 mmol) was then added to the reaction mixture followed by degassing with nitrogen for another 15 min. The resulting reaction mixture was then heated to 85° C. for 4 h. After the completion of the reaction (TLC monitoring), the reaction mixture was cooled to room temperature and poured onto ice-cold water followed by extraction with EtOAc (2×100 mL). The combined organics was washed with brine, dried (Na₂SO₄), filtered and concentrated under reduced pressure. The crude was then purified over silica gel (100-200 M, 3.0% MeOH-DCM) to obtain the desired product (0.025 g, 33%). ¹H-NMR (400 MHz, DMSO-d₆): δ 1.10 (t, J=7.20 Hz, 3H), 3.19 (m, 2H), 6.74 (br s, 1H), 7.18 (s, 1H), 7.68 (dd, J=1.60 and 8.40 Hz, 1H), 8.0 (s, 1H), 8.06 (d, J=8.40 Hz, 1H), 8.10 (s, 1H), 8.64 (s, 1H), 9.27 (s, 2H) and 10.78 (br s, 1H). MS: 366.12 (M+H)⁺. Qualitative HPLC Purity (Acquity BEH C-18, 100×2.1 mm, 268 nm): 96.87% (Rt=3.89 min).

Scheme-14:

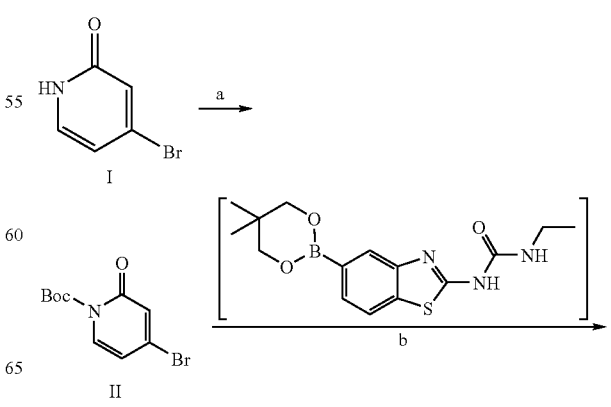

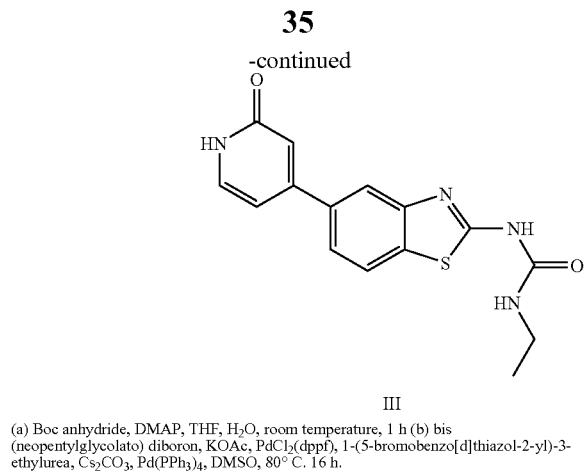

III (a) Boc anhydride, DMAP, THF, H₂O, room temperature, 1 h (b) bis (neopentylglycolato) diboron, KOAc, PdCl₂(dppf), 1-(5-bromobenzo[d]thiazol-2-yl)-3-ethylurea, Cs₂CO₃, Pd(PPh₃)₄, DMSO, 80° C. 16 h.

Preparation of tert-butyl 4-bromo-2-oxopyridine-1(2H)-carboxylate (II)

To an ice cold solution of 5-bromopyridin-2(1H)-one (0.20 g, 1.15 mmol) in THF (5 mL) was added 4-dimethylaminopyridine (DMAP) (0.014 g, 0.12 mmol) followed by drop wise addition of Boc anhydride (0.27 g, 0.12 mmol). The reaction mixture was allowed to come at room temperature and stirred for 1 h. After completion of reaction (TLC monitoring), water was added to the reaction mixture followed by extraction with EtOAc (2×25 mL). The combined organics was dried over Na2SO4 and evaporated upto dryness. The crude white solid was used for next step without further purification (0.27 g, 86%). MS: 274.0 (M+H⁺).

Preparation of 1-ethyl-3-(5-(2-oxo-1,2-dihydropyridin-4-yl)benzo[d]thiazol-2-yl)urea (III)

Example 29

To a solution of 1-(5-bromobenzo[d]thiazol-2-yl)-3-ethylurea (0.20 g, 0.67 mmol) in DMSO (5 mL) was added KOAc (0.20 g, 0.2.01 mmol) and bis (neopentyl glycolato) diboron (0.30 g, 1.34 mmol) at room temperature. The resulting mixture was degassed for 15-20 min by purging nitrogen followed by the addition of PdCl₂.dppf (0.06 g, 0.07 mmol). The reaction mixture was again degassed for 15-20 min and then heated to 80° C. for 3 h. After completion of reaction (TLC monitoring), the reaction mixture was cooled to room temperature followed by in situ addition of tert-butyl 4-bromo-2-oxopyridine-1(2H)-carboxylate (0.27 g, 1.0 mmol) and Cs₂CO₃ (0.20 g in 0.2 mL H₂O). The resulting reaction mixture was degassed for 10-15 min followed by the addition of Pd(PPh₃)₄ (0.05 g, 0.07 mmol). The reaction mixture was finally degassed for 15-20 min and then heated to 80° C. for 16 h. After completion of reaction (TLC monitoring), water (50 mL) was added to the reaction mixture followed by extraction with EtOAc (2×50 mL). The combined organics was dried over Na₂SO₄ and concentrated. The crude residue was purified over silica-gel (100-200 M, 4% MeOH-DCM) to obtain the desired de-Boc product (0.017 g, 8%). ¹H-NMR (400 MHz, DMSO-d₆, D₂O Exchange): δ 1.06 (t, J=7.20 Hz, 3H), 3.15 (m, 2H), 6.56 (d, J=9.20 Hz, 1H), 7.39 (d, J=7.60 Hz, 1H), 7.75 (m, 2H), 7.87 (d, J=8.40 Hz, 1H) and 7.96 (d, J=10.80 Hz, 1H). MS: 313.08 (M−H)⁺. Qualitative HPLC Purity (Acquity BEH C-18, 2.1×100 mm, 261 nm): 94.42% (Rt=4.24 min).

Scheme-15:

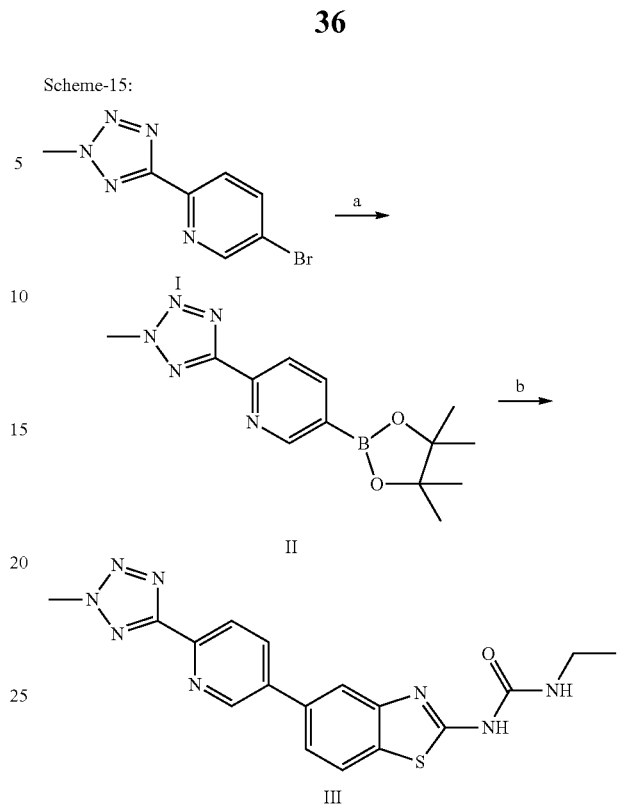

(a) Bispinacolatodiboron, KOAc, Pd₂(dba)₃, tricyclohexyphosphine, 1,4-dioxane;
(b) 2-(3-ethylureido)benzo[d]thiazol-5-yl trifluoromethanesulfonate, K₃PO₄, Dichlorobis(triphenylphosphine)-palladium(II), DMF—H₂O.

Preparation of 2-(2-methyl-2H-tetrazol-5-yl)-5-(4,4,5,5-tetramethyl-1,3,2-dioxaborolan-2-yl)pyridine (II)

A solution of 5-bromo-2-(2-methyl-2H-tetrazol-5-yl)pyridine (0.15 g, 0.63 mmol), bispinacolatodiboron (0.176 g, 0.69 mmol) and KOAc (0.076 g, 0.93 mmol) in 1,4-dioxane (5.0 mL) was degassed by flushing with nitrogen for 15 min. Tricyclohexylphosphine (0.02 g, 0.07 mmol) and tris(dibenzyledineacetone)dipalladium(0) (0.03 g, 0.03 mmol) was then added to the reaction mixture that was again degassed by nitrogen for 15 min. The resulting reaction mixture was heated to 100° C. for 3 h. After the completion of the reaction (TLC monitoring), the reaction mixture was filtered through celite bed and the filtrate was concentrated to get the crude residue that was carried forward to the next step without further purification. MS: 288.10 (M+H)⁺.

Preparation of 1-ethyl-3-(5-(6-(2-methyl-2H-tetrazol-5-yl)pyridin-3-yl)benzo[d]thiazol-2-yl)urea (III)

Example 30

A solution of 2-(3-ethylureido)benzo[d]thiazol-5-yl trifluoromethanesulfonate (0.10 g, 0.27 mmol), 2-(2-methyl-2H-tetrazol-5-yl)-5-(4,4,5,5-tetramethyl-1,3,2-dioxaborolan-2-yl)pyridine (0.093 g, 0.32 mmol) and K₃PO₄ (0.085 g, 0.40 mmol) in DMF-H₂O (5.0 mL, 4:1) was degassed by flushing with nitrogen for 15 min. Dichlorobis(triphenylphosphine)-palladium(II) (0.018 g, 0.020 mmol) was then added to the reaction mixture followed by degassing with nitrogen for another 15 min. The resulting reaction mixture was then heated to 80° C. for 16 h. After the completion of the reaction (TLC monitoring), the reaction mixture was cooled to room temperature and poured onto ice-cold water followed by extraction with EtOAc (2×50 mL). The combined organics was washed with brine, dried (Na₂SO₄), filtered and concentrated under reduced pressure. The crude was then purified over silica gel (100-200 M, 2.8% MeOH-DCM) to obtain the desired product (0.005 g, 4%). ¹H-NMR (400 MHz, DMSO-$d_6$): δ 1.10 (t, J=7.20 Hz, 3H), 3.20 (m, 2H), 4.48 (s, 3H), 6.75 (br s, 1H), 7.68 (d, J=9.20 Hz, 1H), 8.06 (m, 2H), 8.20 (m, 1H), 8.36 (m, 1H), 9.14 (s, 1H) and 10.80 (br s, 1H). MS: 381.11 (M+H)⁺. Qualitative HPLC Purity (Acquity BEH C-18, 100×2.1 mm, 266 nm): 95.53% (Rt=5.04 min).

Scheme-16:

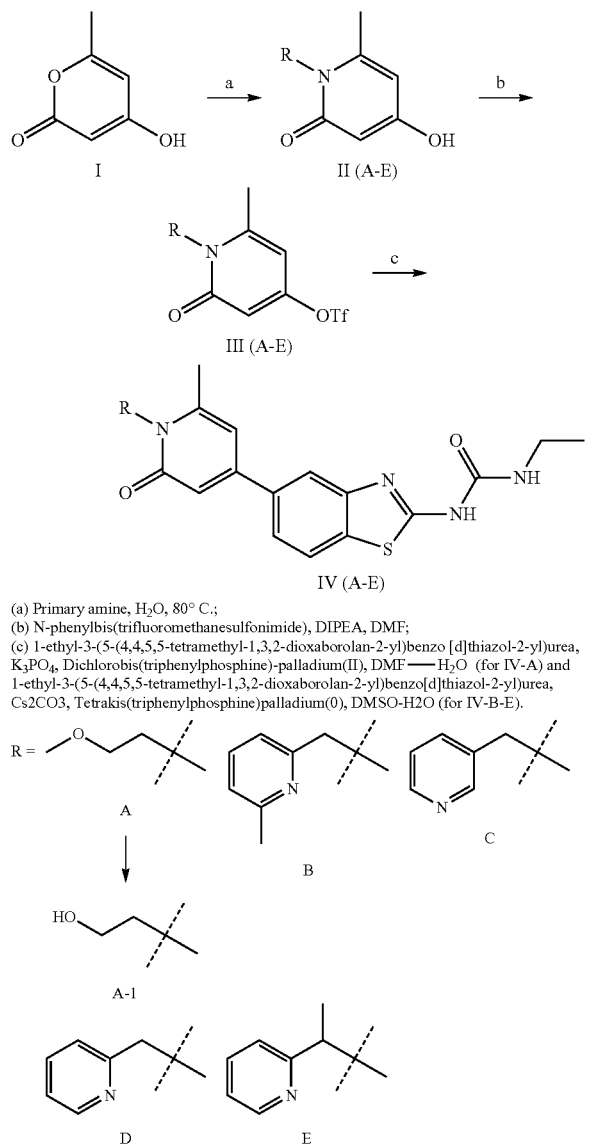

(a) Primary amine, H₂O, 80° C.;
(b) N-phenylbis(trifluoromethanesulfonimide), DIPEA, DMF;
(c) 1-ethyl-3-(5-(4,4,5,5-tetramethyl-1,3,2-dioxaborolan-2-yl)benzo [d]thiazol-2-yl)urea, K₃PO₄, Dichlorobis(triphenylphosphine)-palladium(II), DMF—H₂O (for IV-A) and 1-ethyl-3-(5-(4,4,5,5-tetramethyl-1,3,2-dioxaborolan-2-yl)benzo[d]thiazol-2-yl)urea, Cs2CO3, Tetrakis(triphenylphosphine)palladium(0), DMSO-H2O (for IV-B-E).

General Procedure for the Preparation of Substituted Cyclic Amides (II)

A mixture of 6-methyl-4-hydroxy pyranone (1.0 eq) and primary amine (1.20 eq) in water (5 times dilution by weight) was heated to 80° C. for 16 h. After the completion of reaction (TLC monitoring), the precipitated solid was filtered, washed with ether and dried under vacuum to obtain the desired product (around 75% yield).

General Procedure for the Preparation of Triflates (III)

To a solution of cyclic amide II (1.0 eq) in DMF was added DIPEA (1.15 eq) and the resulting mixture was stirred at room temperature for 15 min followed by addition of N-phenylbis(trifluoromethanesulfonimide) (1.20 eq). The resulting reaction mixture was continued to stir at room temperature for 2 h. After the completion of reaction (TLC monitoring), the reaction mixture was poured onto the ice-cold water and extracted with EtOAc (3×100 mL). The combined organics was washed with brine, dried over Na₂SO₄, filtered and concentrated under reduced pressure to obtain the desired product that was carried forward to the next step without further purification.

Preparation of 1-ethyl-3-(5-(1-(2-methoxyethyl)-6-methyl-2-oxo-1,2-dihydropyridin-4-yl)benzo[d]thiazol-2-yl)urea (IV-A)

Example 31

A solution of 1-(2-methoxyethyl)-6-methyl-2-oxo-1,2-dihydropyridin-4-yl trifluoromethanesulfonate (0.20 g, 0.65 mmol), 1-ethyl-3-(5-(4,4,5,5-tetramethyl-1,3,2-dioxaborolan-2-yl)benzo[d]thiazol-2-yl)urea (0.15 g, 0.43) and K₃PO₄ (0.14 g, 0.65 mmol) in DMF-H₂O (5.0 mL, 3:2) was degassed by flushing with nitrogen for 15 min. Dichlorobis(triphenylphosphine)-palladium(II) (0.03 g, 0.04 mmol) was then added to the reaction mixture followed by degassing with nitrogen for another 15 min. The resulting reaction mixture was then heated to 85° C. for 4 h. After the completion of the reaction (TLC monitoring), the reaction mixture was cooled to room temperature and poured onto ice-cold water followed by extraction with EtOAc (2×50 mL). The combined organics was washed with brine, dried (Na₂SO₄), filtered and concentrated under reduced pressure. The crude was then purified over silica gel (100-200 M, 2.50% MeOH-DCM) to obtain the desired product (0.05 g, 32.0%). ¹H-NMR (400 MHz, DMSO-$d_6$): δ 1.11 (t, J=7.20 Hz, 3H), 2.50 (s, 3H), 3.19 (m, 2H), 3.24 (s, 3H), 3.58 (t, J=5.60 Hz, 2H), 4.14 (t, J=5.20 Hz, 2H), 6.59 (s, 2H), 6.73 (br s, 1H), 7.54 (m, 1H), 7.91 (s, 1H), 7.97 (d, J=8.0 Hz, 1H) and 10.80 (br s, 1H). MS: 387.15 (M+H)⁺. Qualitative HPLC Purity (Acquity BEH C-18, 100× 2.1 mm, 263 nm): 98.18% (Rt=4.93 min).

Preparation of 1-ethyl-3-(5-(1-(2-hydroxyethyl)-6-methyl-2-oxo-1,2-dihydropyridin-4-yl)benzo[d]thiazol-2-yl)urea (IV-A-1)

Example 32

To a solution of 1-ethyl-3-(5-(1-(2-methoxyethyl)-6-methyl-2-oxo-1,2-dihydropyridin-4-yl)benzo[d]thiazol-2-yl)urea IV-A (0.035 g, 0.09 mmol) in DCM (3.50 mL) at −78° C. was added BBr₃ (0.034 g, 0.14 mmol) and the resulting reaction mixture was then stirred at 0° C. for 1 h. After the completion of reaction (TLC monitoring), the reaction mixture again cooled to −78° C. and quenched with saturated solution of NaHCO₃ (1.0 mL). The reaction mixture was then diluted with water and the extracted with EtOAc (3×20 mL). The combined organics was washed with brine, dried (Na₂SO₄), filtered and concentrated to obtain the desired product (0.015 g, 43%). ¹H-NMR (400 MHz, DMSO-$d_6$): δ 0.59 (t, J=6.80 Hz, 3H), 2.70 (m, 2H), 2.80 (s, 3H), 3.14 (m, 2H), 3.52 (t, J=5.60 Hz, 2H), 4.47 (t, J=5.20 Hz, 1H), 6.08 (s, 2H), 6.26 (m, 1H), 7.04 (d, J=8.40 Hz, 1H), 7.40 (s, 1H), 7.47 (d, J=7.60 Hz, 1H), and 10.29 (br s, 1H). MS: 371.10 (M+H)⁺.

Preparation of 1-ethyl-3-(5-(6-methyl-1-((6-methylpyridin-2-yl)methyl)-2-oxo-1,2-dihydropyridin-4-yl)benzo[d]thiazol-2-yl)urea (IV-B)

Example 33

A solution of 6-methyl-1-((6-methylpyridin-2-yl)methyl)-2-oxo-1,2-dihydropyridin-4-yl trifluoromethanesulfonate (0.10 g, 0.86 mmol), 1-ethyl-3-(5-(4,4,5,5-tetramethyl-1,3,2-dioxaborolan-2-yl)benzo[d]thiazol-2-yl)urea (0.30 g, 0.86 mmol) and Cs$_2$CO$_3$ (0.21 g, 0.64 mmol) in DMSO-H$_2$O (5.0 mL, 4:1) was degassed by flushing with nitrogen for 15 min. Tetarkis(triphenylphosphine)palladium(0) (0.05 g, 0.04 mmol) was then added to the reaction mixture followed by degassing with nitrogen for another 15 min. The resulting reaction mixture was then heated to 85° C. for 4 h. After the completion of the reaction (TLC monitoring), the reaction mixture was cooled to room temperature and poured onto ice-cold water followed by extraction with EtOAc (2×50 mL). The combined organics was washed with brine, dried (Na$_2$SO$_4$), filtered and concentrated under reduced pressure. The crude was then purified over silica gel (100-200 M, 4.2% MeOH-DCM) to obtain the desired product (0.004 g, 1.0%). $^1$H-NMR (400 MHz, DMSO-d$_6$): δ 1.11 (t, J=7.20 Hz, 3H), 2.43 (s, 3H), 2.44 (s, 3H), 3.19 (m, 2H), 5.29 (s, 2H), 6.68 (d, J=5.60 Hz, 2H), 6.74 (br s, 1H), 6.91 (d, J=7.60 Hz, 1H), 7.16 (d, J=7.60 Hz, 1H), 7.59 (d, J=8.0 Hz, 1H), 7.64 (t, J=7.60 Hz, 1H), 7.96 (m, 2H) and 10.82 (br s, 1H). MS: 434.25 (M+H)$^+$. Qualitative HPLC Purity (Acquity BEH C-18, 100×2.1 mm, 265 nm): 94.22% (Rt=5.20 min).

Preparation of 1-ethyl-3-(5-(6-methyl-2-oxo-1-(pyridin-3-ylmethyl)-1,2-dihydropyridin-4-yl)benzo[d]thiazol-2-yl)urea (IV-C)

Example 34

A solution of 6-methyl-2-oxo-1-(pyridin-3-ylmethyl)-1,2-dihydropyridin-4-yl trifluoromethanesulfonate (0.36 g, 1.00 mmol), 1-ethyl-3-(5-(4,4,5,5-tetramethyl-1,3,2-dioxaborolan-2-yl)benzo[d]thiazol-2-yl)urea (0.35 g, 1.0 mmol) and Cs$_2$CO$_3$ (0.25 g, 0.75 mmol) in DMSO-H$_2$O (5.0 mL, 4:1) was degassed by flushing with nitrogen for 15 min. Tetarkis(triphenylphosphine)palladium(0) (0.06 g, 0.05 mmol) was then added to the reaction mixture followed by degassing with nitrogen for another 15 min. The resulting reaction mixture was then heated to 85° C. for 4 h. After the completion of the reaction (TLC monitoring), the reaction mixture was cooled to room temperature and poured onto ice-cold water followed by extraction with EtOAc (2×50 mL). The combined organics was washed with brine, dried (Na$_2$SO$_4$), filtered and concentrated under reduced pressure. The crude was then purified over silica gel (100-200 M, 3.0% MeOH-DCM) to obtain the desired product (0.016 g, 4.0%). $^1$H-NMR (400 MHz, DMSO-d$_6$): δ 1.09 (t, J=7.20 Hz, 3H), 2.38 (s, 3H), 3.19 (m, 2H), 5.34 (s, 2H), 6.72 (m, 3H), 7.38 (m, 1H), 7.58 (m, 2H), 7.96 (m, 2H), 8.49 (m, 2H) and 10.81 (br s, 1H). MS: 420.25. Qualitative HPLC Purity (Acquity BEH C-18, 100×2.1 mm, 264 nm): 99.49% (Rt=4.78 min).

Preparation of 1-ethyl-3-(5-(6-methyl-2-oxo-1-(pyridin-2-ylmethyl)-1,2-dihydropyridin-4-yl)benzo[d]thiazol-2-yl)urea (IV-D)

Example 35

A solution of 6-methyl-2-oxo-1-(pyridin-2-ylmethyl)-1,2-dihydropyridin-4-yl trifluoromethanesulfonate (0.30 g, 0.86 mmol), 1-ethyl-3-(5-(4,4,5,5-tetramethyl-1,3,2-dioxaborolan-2-yl)benzo[d]thiazol-2-yl)urea (0.30 g, 0.86 mmol) and Cs$_2$CO$_3$ (0.21 g, 0.64 mmol) in DMSO-H$_2$O (5.0 mL, 4:1) was degassed by flushing with nitrogen for 15 min. Tetarkis(triphenylphosphine)palladium(0) (0.05 g, 0.04 mmol) was then added to the reaction mixture followed by degassing with nitrogen for another 15 min. The resulting reaction mixture was then heated to 85° C. for 4 h. After the completion of the reaction (TLC monitoring), the reaction mixture was cooled to room temperature and poured onto ice-cold water followed by extraction with EtOAc (2×50 mL). The combined organics was washed with brine, dried (Na$_2$SO$_4$), filtered and concentrated under reduced pressure. The crude was then purified over silica gel (100-200 M, 1.9% MeOH-DCM) to obtain the desired product (0.011 g, 3.0%). $^1$H-NMR (400 MHz, DMSO-d$_6$): δ 1.09 (t, J=7.20 Hz, 3H), 2.40 (s, 3H), 3.19 (m, 2H), 5.35 (s, 2H), 6.67 (d, J=8.80 Hz, 2H), 6.73 (br s, 1H), 7.29 (m, 2H), 7.58 (d, J=8.0 Hz, 1H), 7.78 (t, J=7.60 Hz, 1H), 7.96 (m, 2H), 8.50 (d, J=4.80 Hz, 1H) and 10.80 (br s, 1H). MS: 420.22. Qualitative HPLC Purity (Acquity BEH C-18, 100×2.1 mm, 264 nm): 91.62% (Rt=4.97 min).

Preparation of 1-ethyl-3-(5-(6-methyl-2-oxo-1-(1-(pyridin-2-yl)ethyl)-1,2-dihydropyridin-4-yl)benzo[d]thiazol-2-yl)urea (IV-E)

Example 36

A solution of 6-methyl-2-oxo-1-(1-(pyridin-2-yl)ethyl)-1,2-dihydropyridin-4-yl trifluoromethanesulfonate (0.25 g, 0.66 mmol), 1-ethyl-3-(5-(4,4,5,5-tetramethyl-1,3,2-dioxaborolan-2-yl)benzo[d]thiazol-2-yl)urea (0.30 g, 0.86 mmol) and Cs$_2$CO$_3$ (0.16 g, 0.50 mmol) in DMSO-H$_2$O (5.0 mL, 4:1) was degassed by flushing with nitrogen for 15 min. Tetarkis(triphenylphosphine)palladium(0) (0.04 g, 0.03 mmol) was then added to the reaction mixture followed by degassing with nitrogen for another 15 min. The resulting reaction mixture was then heated to 85° C. for 4 h. After the completion of the reaction (TLC monitoring), the reaction mixture was cooled to room temperature and poured onto ice-cold water followed by extraction with EtOAc (2×50 mL). The combined organics was washed with brine, dried (Na$_2$SO$_4$), filtered and concentrated under reduced pressure. The crude was then purified over silica gel (100-200 M, 2.0% MeOH-DCM) to obtain the desired product (0.004 g, 2.0%). $^1$H-NMR (400 MHz, DMSO-d$_6$): δ 1.09 (t, J=7.20 Hz, 3H), 1.88 (d, J=6.80 Hz, 3H), 3.20 (m, 2H), 3.22 (s, 3H), 6.49 (m, 2H), 6.62 (s, 1H), 6.73 (br s, 1H), 7.24 (m, 1H), 7.34 (d, J=7.60 Hz, 1H), 7.55 (d, J=8.40 Hz, 1H), 7.76 (t, J=7.60 Hz, 1H), 7.91 (s, 1H), 7.97 (d, J=8.40 Hz, 1H), 8.46 (br s, 1H) and 10.81 (br s, 1H). MS: 432.15. Qualitative HPLC Purity (Acquity BEH C-18, 100×2.1 mm, 263 nm): 89.28% (Rt=5.15 min).

Scheme-17:

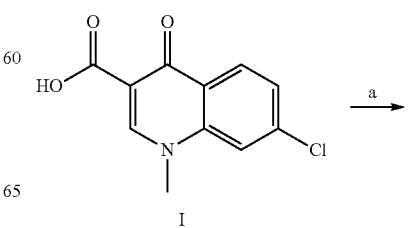

Qualitative HPLC Purity (Acquity BEH C-18, 100×2.1 mm, 263 nm): 87.90% (Rt=4.60 min).

41

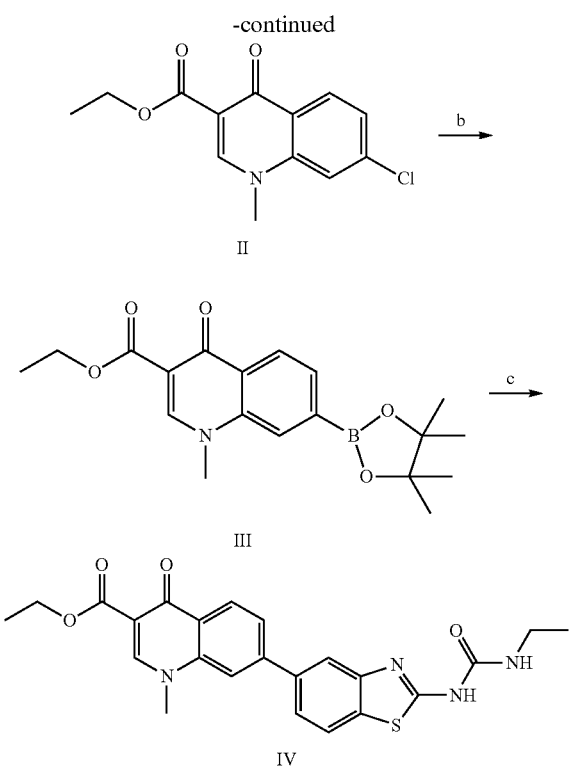

(a) EtOH, SOCl₂, 78° C., 6 h; (b) Bispinacolatodiboron, KOAc, Pd₂(dba)₃, tricyclohexyphosphine, 1,4-dioxane; (c) 1-(5-bromobenzo[d]thiazol-2-yl)-3-ethylurea, K₃PO₄, Dichlorobis(triphenylphosphine)-palladium(II), DMF — H₂O.

Preparation of ethyl 7-chloro-1-methyl-4-oxo-1,4-dihydroquinoline-3-carboxylate (II)

A solution of 7-chloro-1-methyl-4-oxo-1,4-dihydroquinoline-3-carboxylic acid (0.50 g, 2.10 mmol) and SOCl₂ (2.0 mL) in EtOH (15.0 mL) was heated to 78° C. for 6 h. After the completion of reaction (TLC monitoring), EtOH was distilled off, added water and extracted with EtOAc (3×70 mL). The combined organics was washed with saturated NaHCO₃ solution, dried (Na₂SO₄), filtered and concentrated to obtain the desired product in quantitative yields.

Preparation of ethyl 1-methyl-4-oxo-7-(4,4,5,5-tetramethyl-1,3,2-dioxaborolan-2-yl)-1,4-dihydroquinoline-3-carboxylate (III)

A solution of 7-chloro-1-methyl-4-oxo-1,4-dihydroquinoline-3-carboxylate II (0.70 g crude, 2.63 mmol), bispinacolatodiboron (0.74 g, 2.89 mmol) and KOAc (0.39 g, 3.95 mmol) in 1,4-dioxane (12.0 mL) was degassed by flushing with nitrogen for 15 min. Tricyclohexylphosphine (0.089 g, 0.32 mmol) and tris(dibenzyledineacetone)dipalladium(0) (0.12 g, 0.13 mmol) was then added to the reaction mixture, which was again degassed by nitrogen for 15 min. The resulting reaction mixture was heated to 90° C. for 16 h. After the completion of reaction (TLC monitoring), the reaction mixture was filtered through celite bed and the filtrate was concentrated to get the crude residue that was carried forward to the next step without further purification. MS: 358.10 (M+H)⁺.

42

Preparation of ethyl 7-(2-(3-ethylureido)benzo[d]thiazol-5-yl)-1-methyl-4-oxo-1,4-dihydroquinoline-3-carboxylate (IV)

Example 37

A solution of ethyl 1-methyl-4-oxo-7-(4,4,5,5-tetramethyl-1,3,2-dioxaborolan-2-yl)-1,4-dihydroquinoline-3-carboxylate III (0.60 g, 1.67 mmol), 1-(5-bromobenzo[d]thiazol-2-yl)-3-ethylurea (0.25 g, 0.84 mmol) and K₃PO₄ (0.36 g, 1.67 mmol) in DMF-H₂O (7.5 mL, 2:1) was degassed by flushing with nitrogen for 15 min. [1,1'-Bis(diphenylphosphino)-ferrocene]dichloropalladium(II) (0.07 g, 0.084 mmol) was then added to the reaction mixture followed by degassing with nitrogen for another 15 min. The resulting reaction mixture was then heated to 80° C. for 5 h. After the completion of the reaction (TLC monitoring), the reaction mixture was cooled to room temperature and poured onto ice-cold water followed by extraction with EtOAc (4×50 mL). The combined organics was washed with brine, dried (Na₂SO₄), filtered and concentrated under reduced pressure. The crude was then purified over silica gel (230-400 M, 7% MeOH-DCM) to obtain the desired product (0.002 g, negligible yield). ¹H-NMR (400 MHz, DMSO-d₆): δ 1.11 (t, J=7.20 Hz, 3H), 1.21 (t, J=7.20 Hz, 3H), 3.19 (m, 2H), 3.94 (s, 3H), 4.14 (m, 2H), 6.85 (br s, 1H), 6.99 (d, J=8.0 Hz, 1H), 7.22 (d, J=5.60 Hz, 1H), 7.36 (s, 1H), 7.77 (m, 3H), 8.65 (s, 1H) and 10.01 (br s, 1H). LCMS: 451.21 (M+H)⁺, 96.95%.

Scheme-18:

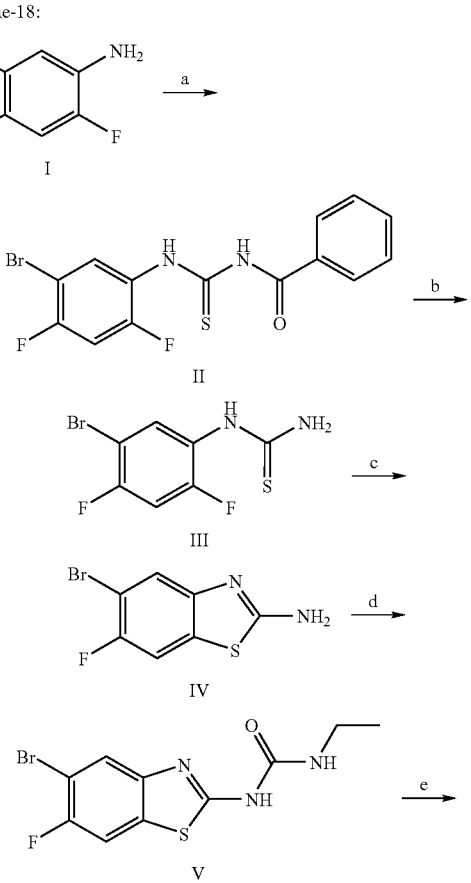

-continued

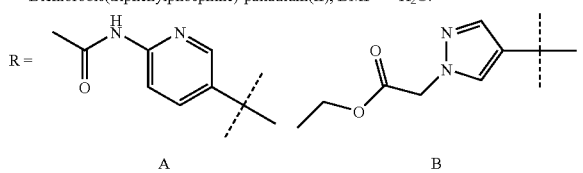

VI (A-B)

(a) Benzoyl isothiocyanate, actone;
(b) NaOH—THF;
(c) NaH, NMP;
(d) Ethyl isocyanate, 1,4-dioxane;
(e) corresponding boronate, $K_3PO_4$, Dichlorobis(triphenylphosphine)-palladium(II), DMF—$H_2O$.

R =

A    B

Preparation of 1-benzoyl-3-(5-bromo-2,4-difluoro-phenyl)-thiourea (II)

To a solution of 5-bromo-2,4-difluoro aniline (1.0 g, 4.81 mmol) in acetone (25.0 mL) was added drop wise benzoyl isothiocyanate (0.71 mL, 5.29 mmol). The resulting reaction mixture was allowed to stir at room temperature for 30 min. After the completion of the reaction (TLC monitoring), the solvent was evaporated and the residue was washed with hexane and ether to get the title compound (1.70 g, quantitative yield) as a white solid. $^1$H-NMR (400 MHz, $CDCl_3$): δ 7.02-7.06 (m, 1H), 7.56 (t, J=8.0 Hz, 2H), 7.68 (t, J=7.60 Hz, 1H), 7.91 (d, J=7.60 Hz, 2H), 8.67 (t, J=7.60 Hz, 1H), 9.15 (br s, 1H) and 12.65 (br s, 1H).

Preparation of (5-bromo-2,4-difluoro-phenyl)-thiourea: III

To a solution of 1-benzoyl-3-(5-bromo-2,4-difluoro-phenyl)-thiourea II (1.70 g, 4.60 mmol) in THF (35.0 mL) was added a solution of NaOH (0.97 g, 24.25 mmol) in water (13.0 mL). The resulting reaction mixture was stirred at 70° C. for 15 h. After the completion of the reaction (TLC monitoring), THF was evaporated, added water and extracted with EtOAc (3×50 mL). The combined organics was washed with brine and concentrated to obtain the desired compound (1.0 g, 83%). MS: 267.03 $(M+H)^+$.

Preparation of 5-bromo-6-fluoro-benzothiazol-2-ylamine: IV

To a solution of (5-bromo-2,4-difluoro-phenyl)-thiourea III (0.75 g, 2.80 mmol) in NMP (5.0 mL) was added NaH (0.17 g, 4.21 mmol, 60% suspension in mineral oil) portion wise. The reaction mixture was then heated at 130° C. for 2 h. The reaction mixture was then poured onto crushed ice and extracted with EtOAc (3×50 mL). The combined organics was evaporated to get the crude residue that was purified over silica gel (100-200 M, 12% EtOAc-Hexane) to obtain the desired compound (0.36 g, 52%). $^1$H-NMR (400 MHz, DMSO-$d_6$): δ 7.57 (d, J=6.40 Hz, 1H), 7.66 (br s, 2H) and 7.79 (d, 8.80 Hz, 1H).

Preparation of 1-(5-bromo-6-fluoro-benzothiazol-2-yl)-3-ethyl-urea: V

To a solution of 5-bromo-6-fluoro-benzothiazol-2-ylamine IV (0.36 g, 1.45 mmol) in 1,4-dioxane (25.0 mL) was added ethyl isocyanate (0.69 mL, 8.74 mmol) and the resulting reaction mixture was heated at 80° C. for 15 h. After the completion of the reaction (TLC monitoring) the solvent was evaporated. The residue thus obtained was stirred with water at 60° C. for 5 h. The solution was then filtered and washed with ether to get the title compound (0.30 g, 69%). $^1$H-NMR (400 MHz, DMSO-$d_6$): δ 1.08 (t, J=6.80 Hz, 3H), 3.17 (m, 2H), 6.69 (br s, 1H), 7.92 (d, J=6.40 Hz, 1H), 8.0 (d, J=8.40 Hz, 1H) and 10.86 (br s, 1H).

Preparation of N-(5-(2-(3-ethylureido)-6-fluorobenzo[d]thiazol-5-yl)pyridin-2-yl)acetamide (VI-A)

Example 38

A solution of 1-(5-bromo-6-fluoro-benzothiazol-2-yl)-3-ethyl-urea V (0.10 g, 0.31 mmol), N-(5-(4,4,5,5-tetramethyl-1,3,2-dioxaborolan-2-yl)pyridin-2-yl)acetamide (0.17 g, 0.62 mmol) and $K_3PO_4$ (0.067 g, 0.31 mmol) in DMF-$H_2O$ (2.5 mL, 2:0.5) was degassed by flushing with nitrogen for 15 min. Dichlorobis(triphenylphosphine)-palladium(II) (0.022 g, 0.031 mmol) was then added to the reaction mixture followed by degassing with nitrogen for another 15 min. The resulting reaction mixture was then heated to 110° C. for 2 h. After the completion of the reaction (TLC monitoring), the reaction mixture was cooled to room temperature and poured onto ice-cold water followed by extraction with EtOAc (3×25 mL). The combined organics was washed with brine, dried ($Na_2SO_4$), filtered and concentrated under reduced pressure. The crude was then purified over silica gel (100-200 M, 1.5% MeOH-DCM) and then through prep-HPLC to obtain the desired product (0.046 g, 39%). $^1$H-NMR (400 MHz, DMSO-$d_6$): δ 1.08 (t, J=7.20 Hz, 3H), 2.12 (s, 3H), 3.20 (quintet, J=6.40 Hz, 2H), 6.77 (br s, 1H), 7.75 (d, J=6.80 Hz, 1H), 7.93 (d, J=10.40 Hz, 1H), 8.01 (d, J=8.40 Hz, 1H), 8.18 (d, J=8.80 Hz, 1H), 8.52 (s, 1H), 10.63 (br s, 1H) and 10.85 (br s, 1H). MS: 374.20 $(M+H)^+$. Qualitative HPLC Purity (Acquity BEH C-18, 100×2.1 mm, 261 nm): 98.72% (Rt=5.03 min).

Preparation of ethyl 2-(4-(2-(3-ethylureido)-6-fluorobenzo[d]thiazol-5-yl)-1H-pyrazol-1-yl)acetate (VI-B)

Example 39

A solution of 1-(5-bromo-6-fluoro-benzothiazol-2-yl)-3-ethyl-urea V (0.10 g, 0.31 mmol), 1-(ethoxycarbonylmethyl)-1H-pyrazole-4-boronic acid, pinacol ester (0.18 g, 0.63 mmol) and $K_3PO_4$ (0.067 g, 0.31 mmol) in DMF-$H_2O$ (2.5 mL, 2:0.5) was degassed by flushing with nitrogen for 15 min. Dichlorobis(triphenylphosphine)-palladium(II) (0.022 g, 0.031 mmol) was then added to the reaction mixture followed by degassing with nitrogen for another 15 min. The resulting reaction mixture was then heated to 110° C. for 2 h. After the completion of the reaction (TLC monitoring), the reaction mixture was cooled to room temperature and poured onto ice-cold water followed by extraction with EtOAc (2×50 mL). The combined organics was washed with brine, dried ($Na_2SO_4$), filtered and concentrated under reduced pressure. The crude was then purified over silica gel (100-200 M, 1.0% MeOH-DCM) to obtain the desired product (0.024 g, 20%). $^1$H-NMR (400 MHz, DMSO-$d_6$): δ 1.08 (t, J=7.20 Hz, 3H), 1.22 (t, J=7.20 Hz, 3H), 3.20 (m, 2H), 4.18 (q, J=7.20 Hz, 2H), 5.12 (s, 2H), 6.69 (br s, 1H), 7.86 (d, J=10.80 Hz, 1H), 7.94 (d, J=6.40 Hz, 1H), 8.04 (s, 1H), 8.21 (d, J=2.40 Hz, 1H)

and 10.71 (br s, 1H). MS: 392.21 (M+H)$^+$. Qualitative HPLC Purity (Acquity BEH C-18, 100×2.1 mm, 249 nm): 89.68% (Rt=5.33 min).

Scheme-19:

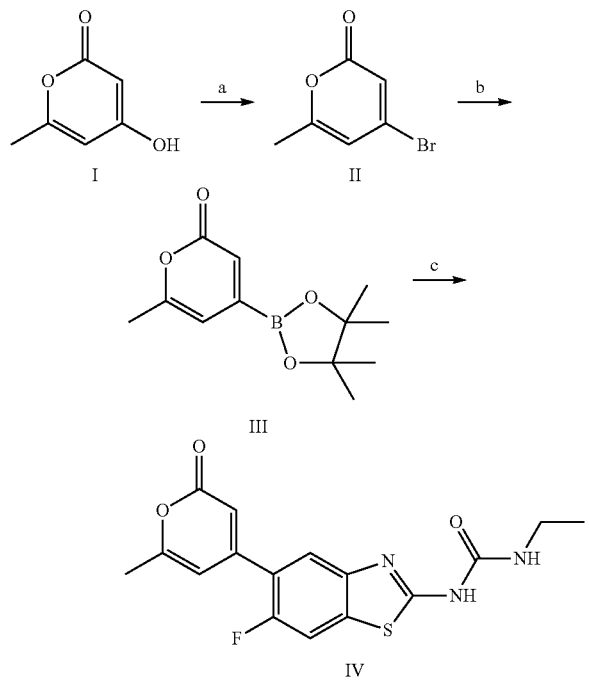

(a) P$_2$O$_5$, TBAB, toluene; (b) Bispinacolatodiboron, KOAc, Pd$_2$(dba)$_3$, tricyclohexyphosphine, 1,4-dioxane; (c) 1-(5-bromo-6-fluoro-benzothiazol-2-yl)-3-ethyl-urea, K$_3$PO$_4$, Dichlorobis(triphenylphosphine)-palladium(II), DMF——H$_2$O.

Preparation of 4-bromo-6-methyl-2H-pyran-2-one (II)

A solution of 4-hydroxy-6-methyl-2-pyrone (0.50 g, 3.96 mmol), P$_2$O$_5$ (1.41 g, 9.91 mmol) and TBAB (1.53 g, 4.76 mmol) in toluene (25 mL) was heated to 100° C. for 1.50 h. After the completion of reaction (TLC monitoring), the reaction mixture was cooled to room temperature, added water and extracted the organic layer. The aqueous layer was re-extracted with toluene (2×20 mL). The combined organics was washed saturated NaHCO$_3$ solution followed by brine wash, dried (Na$_2$SO$_4$), filtered and concentrated to obtain the desired product (0.57 g, 76%). MS: 189.10 (M+H)$^+$.

Preparation of 6-methyl-4-(4,4,5,5-tetramethyl-1,3,2-dioxaborolan-2-yl)-2H-pyran-2-one (III)

A solution of 4-bromo-6-methyl-2H-pyran-2-one II (0.15 g, 0.79 mmol), bispinacolatodiboron (0.22 g, 0.87 mmol) and KOAc (0.12 g, 1.19 mmol) in 1,4-dioxane (10.0 mL) was degassed by flushing with nitrogen for 15 min. Tricyclohexylphosphine (0.027 g, 0.10 mmol) and tris(dibenzyledineacetone)dipalladium(0) (0.036 g, 0.04 mmol) was then added to the reaction mixture, which was again degassed by nitrogen for 15 min. The resulting reaction mixture was heated to 80° C. for 2 h. After the completion of the reaction (TLC monitoring), the reaction mixture was filtered through celite bed and the filtrate was concentrated to get the crude residue that was carried forward to the next step without further purification. MS: 237.10 (M+H)$^+$.

Preparation of 1-ethyl-3-(6-fluoro-5-(6-methyl-2-oxo-2H-pyran-4-yl)benzo[d]thiazol-2-yl)urea (IV)

Example 40

A solution of 1-(5-bromo-6-fluoro-benzothiazol-2-yl)-3-ethyl-urea (0.08 g, 0.25 mmol), 6-methyl-4-(4,4,5,5-tetramethyl-1,3,2-dioxaborolan-2-yl)-2H-pyran-2-one (0.118 g, 0.50 mmol) and K$_3$PO$_4$ (0.064 g, 0.30 mmol) in DMF-H$_2$O (2.5 mL, 2:0.5) was degassed by flushing with nitrogen for 15 min. Dichlorobis(triphenylphosphine)-palladium(II) (0.018 g, 0.03 mmol) was then added to the reaction mixture followed by degassing with nitrogen for another 15 min. The resulting reaction mixture was then heated to 110° C. for 2 h. After the completion of the reaction (TLC monitoring), the reaction mixture was cooled to room temperature and poured onto ice-cold water followed by extraction with EtOAc (3×20 mL). The combined organics was washed with brine, dried (Na$_2$SO$_4$), filtered and concentrated under reduced pressure. The crude was then purified over silica gel (100-200 M, 1.0% MeOH-DCM) and then through prep-HPLC to obtain the desired product (0.026 g, 30%). $^1$H-NMR (400 MHz, DMSO-d$_6$): δ 1.08 (t, J=7.20 Hz, 3H), 2.29 (s, 3H), 3.19 (m, 2H), 6.40 (s, 1H), 6.59 (s, 1H), 6.91 (br s, 1H), 7.80 (d, J=6.40 Hz, 1H), 7.97 (d, J=10.80 Hz, 1H) and 10.33 (br s, 1H). MS: 348.07 (M+H)$^+$. Qualitative HPLC Purity (Acquity BEH C-18, 100×2.1 mm, 237 nm): 98.50% (Rt=5.43 min).

Scheme-20:

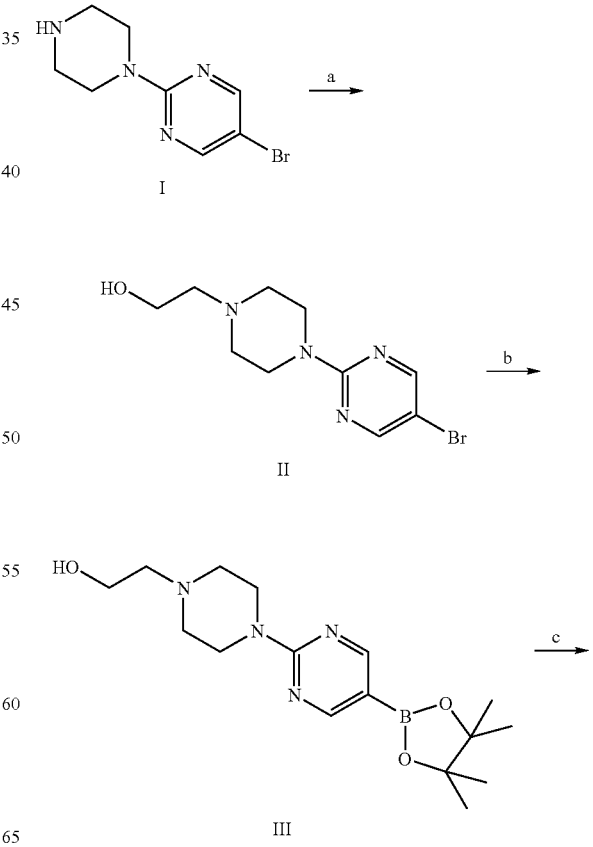

-continued

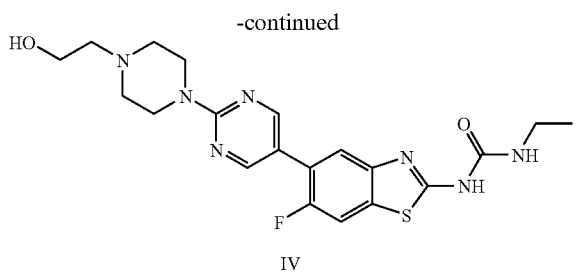

(a) 2-Bromoethanol, K₂CO₃, acetone;
(b) Bispinacolatodiboron, KOAc, Pd₂(dba)₃, tricyclohexyphosphhine, 1,4-dioxane;
(c) 1-(5-bromo-6-fluoro-benzothiazol-2-yl)-3-ethyl-urea, K₃PO₄, Dichlorobis(triphenylphosphine)-palladium(II), DMF—H₂O.

Preparation of 2-(4-(5-bromopyrimidin-2-yl)piperazin-1-yl)ethanol (II)

To a solution of 5-bromo-2-(piperazin-1-yl)pyrimidine (0.20 g, 0.83 mmol) in acetone (10.0 mL) was added K₂CO₃ (0.58 g, 4.17 mmol) followed by the addition of 2-bromoethanol (0.01 g, 1.66 mmol). The resulting reaction mixture was heated to reflux for 3 h. After the completion of reaction (TLC monitoring), the reaction mixture was cooled, added water and extracted with EtOAc (2×100 mL). The combined organics was washed with brine, dried (Na₂SO₄), filtered and concentrated. The crude residue was purified over silica gel (100-200 M, 2% MeOH-DCM) to obtain the desired product (0.11 g, 47%). MS: 287.10 (M+H)⁺.

Preparation of 2-(4-(5-(4,4,5,5-tetramethyl-1,3,2-dioxaborolan-2-yl)pyrimidin-2-yl)piperazin-1-yl)ethanol (III)

A solution of 2-(4-(5-bromopyrimidin-2-yl)piperazin-1-yl)ethanol II (0.10 g, 0.35 mmol), bispinacolatodiboron (0.098 g, 0.39 mmol) and KOAc (0.052 g, 0.53 mmol) in 1,4-dioxane (10.0 mL) was degassed by flushing with nitrogen for 15 min. Tricyclohexylphosphine (0.012 g, 0.043 mmol) and tris(dibenzyledineacetone)dipalladium(0) (0.016 g, 0.017 mmol) was then added to the reaction mixture, which was again degassed by nitrogen for 15 min. The resulting reaction mixture was heated to 95-100° C. for 3 h. After the completion of the reaction (TLC monitoring), the reaction mixture was filtered through celite bed and the filtrate was concentrated to get the crude residue that was carried forward to the next step without further purification. MS: 335.21 (M+H)⁺.

Preparation of 1-ethyl-3-(6-fluoro-5-(2-(4-(2-hydroxyethyl)piperazin-1-yl)pyrimidin-5-yl)benzo[d]thiazol-2-yl)urea (IV)

Example 41

A solution of 1-(5-bromo-6-fluoro-benzothiazol-2-yl)-3-ethyl-urea (0.08 g, 0.25 mmol), 2-(4-(5-(4,4,5,5-tetramethyl-1,3,2-dioxaborolan-2-yl)pyrimidin-2-yl)piperazin-1-yl)ethanol (0.10 g, 0.30 mmol) and K₃PO₄ (0.08 g, 0.38 mmol) in DMF-H₂O (3.0 mL, 2:1) was degassed by flushing with nitrogen for 15 min. Dichlorobis(triphenylphosphine)-palladium(II) (0.009 g, 0.013 mmol) was then added to the reaction mixture followed by degassing with nitrogen for another 15 min. The resulting reaction mixture was then heated to 95-100° C. for 16 h. After the completion of the reaction (TLC monitoring), the reaction mixture was cooled to room temperature and poured onto ice-cold water followed by extraction with DCM (2×100 mL). The combined organics was washed with brine, dried (Na₂SO₄), filtered and concentrated under reduced pressure. The crude was then purified over neutral alumina (4.0% MeOH-DCM) to obtain the desired product (0.070 g, 63%). ¹H-NMR (400 MHz, DMSO-d₆): δ 1.08 (t, J=7.20 Hz, 3H), 2.45 (m, 2H), 3.20 (m, 2H), 3.34 (m, 4H), 3.55 (q, J=5.60 Hz, 2H), 3.78 (br s, 4H), 4.45 (t, J=5.60 Hz, 1H), 6.71 (br s, 1H), 7.75 (d, J=6.80 Hz, 1H), 7.92 (d, J=10.40 Hz, 1H), 8.64 (s, 2H) and 10.75 (br s, 1H). MS: 446.14 (M+H)⁺. Qualitative HPLC Purity (Acquity BEH C-18, 100×2.1 m, 228 nm): 95.88% (Rt=4.82 min).

Scheme-21:

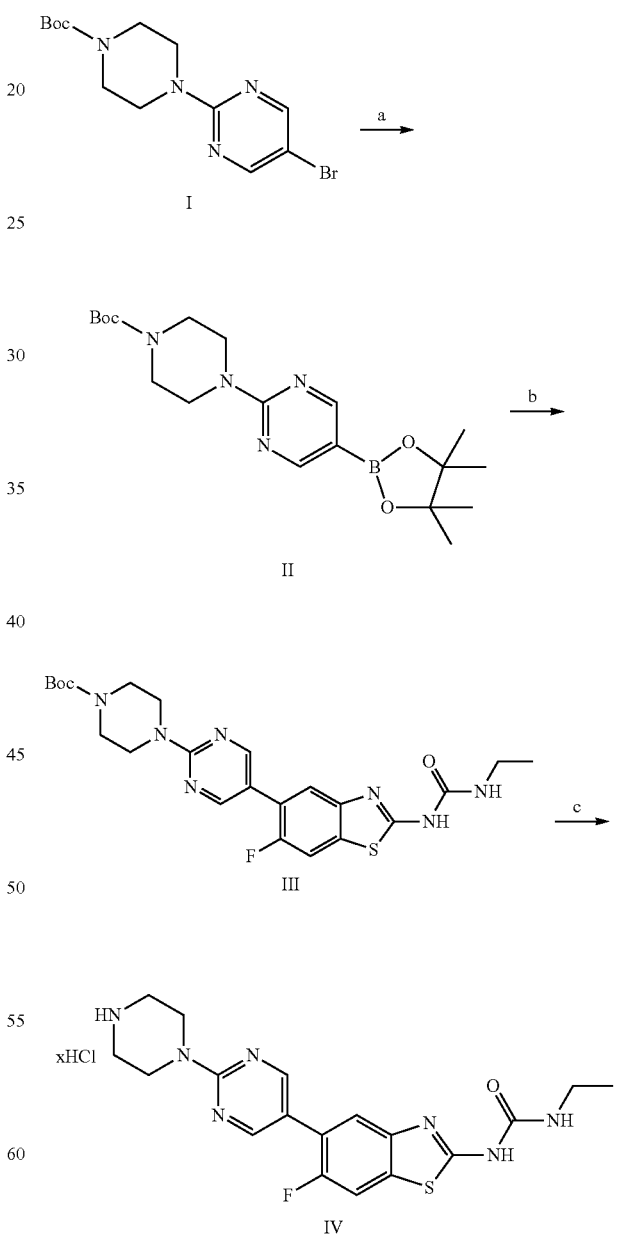

(a) Bispinacolatodiboron, KOAc, Pd₂(dba)₃, tricyclohexyphosphine, 1,4-dioxane;
(b) 1-(5-bromo-6-fluoro-benzothiazol-2-yl)-3-ethyl-urea, K₃PO₄, Dichlorobis(triphenylphosphine)-palladium(II), DMF—H₂O;  (c) HCl-1,4-dioxane.

Preparation of tert-butyl 4-(5-(4,4,5,5-tetramethyl-1,3,2-dioxaborolan-2-yl)pyrimidin-2-yl)piperazine-1-carboxylate (II)

A solution of 5-bromo-2-(4-Boc-piperazin-1-yl)pyrimidine (0.10 g, 0.29 mmol), bispinacolatodiboron (0.081 g, 0.32 mmol) and KOAc (0.035 g, 0.43 mmol) in 1,4-dioxane (5.0 mL) was degassed by flushing with nitrogen for 15 min. Tricyclohexylphosphine (0.010 g, 0.035 mmol) and tris(dibenzyledineacetone)dipalladium(0) (0.013 g, 0.014 mmol) was then added to the reaction mixture, which was again degassed by nitrogen for 15 min. The resulting reaction mixture was heated to 100° C. for 5 h. After the completion of the reaction (TLC monitoring), the reaction mixture was filtered through celite bed and the filtrate was concentrated to get the crude residue that was carried forward to the next step without further purification. MS: 391.21 (M+H)$^+$.

Preparation of tert-butyl 4-(5-(2-(3-ethylureido)-6-fluorobenzo[d]thiazol-5-yl)pyrimidin-2-yl)piperazine-1-carboxylate (III)

A solution of 1-(5-bromo-6-fluoro-benzothiazol-2-yl)-3-ethyl-urea (0.05 g, 0.15 mmol), tert-butyl 4-(5-(4,4,5,5-tetramethyl-1,3,2-dioxaborolan-2-yl)pyrimidin-2-yl)piperazine-1-carboxylate (0.12 g, 0.31 mmol) and K$_3$PO$_4$ (0.13 g, 0.61 mmol) in DMF-H$_2$O (5.0 mL, 3:2) was degassed by flushing with nitrogen for 15 min. Dichlorobis(triphenylphosphine)-palladium(II) (0.021 g, 0.03 mmol) was then added to the reaction mixture followed by degassing with nitrogen for another 15 min. The resulting reaction mixture was then heated to 95-100° C. for 2 h. After the completion of the reaction (TLC monitoring), the reaction mixture was cooled to room temperature and poured onto ice-cold water followed by extraction with EtOAc (2×50 mL). The combined organics was washed with brine, dried (Na$_2$SO$_4$), filtered and concentrated under reduced pressure. The crude was then purified over silica gel (100-200 M, 1.60% MeOH-DCM) to obtain the desired product (0.015 g, 20%). $^1$H-NMR (400 MHz, DMSO-d$_6$): δ 1.08 (t, J=7.20 Hz, 3H), 1.43 (s, 9H), 3.20 (m, 2H), 3.42 (br s, 4H), 3.79 (br s, 4H), 6.71 (br s, 1H), 7.76 (d, J=6.80 Hz, 1H), 7.92 (d, J=10.40 Hz, 1H), 8.62 (s, 2H) and 10.74 (br s, 1H). MS: 502.27 (M+H)$^+$. Qualitative HPLC Purity (Acquity BEH C-18, 100×2.1 mm, 272 nm): 99.21% (Rt=6.51 min).

Preparation of 1-ethyl-3-(6-fluoro-5-(2-(piperazin-1-yl)pyrimidin-5-yl)benzo[d]thiazol-2-yl)urea hydrochloride salt (IV)

Example 42

A solution of tert-butyl 4-(5-(2-(3-ethylureido)-6-fluorobenzo[d]thiazol-5-yl)pyrimidin-2-yl)piperazine-1-carboxylate (0.010 g, 0.02 mmol) in 4.0 M HCl-1,4-dioxane (5.0 mL) was stirred for 30 min. After the completion of reaction (TLC monitoring), the solvent was evaporated and the residue was triturated with ether to obtain the desired product (0.005 g, 62%). $^1$H-NMR (400 MHz, DMSO-d$_6$): δ 1.08 (t, J=7.20 Hz, 3H), 3.18 (m, 2H), 3.20 (br s, 4H), 4.0 (br s, 4H), 6.89 (br s, 1H), 7.77 (d, J=6.80 Hz, 1H), 7.93 (d, J=10.40 Hz, 1H), 8.68 (s, 2H), 9.05 (br s, 1H) and 10.83 (br s, 1H). MS: 402.22 (M+H)$^+$. Qualitative HPLC Purity (Acquity BEH C-18, 100×2.1 mm, 267 nm): 98.22% (Rt=4.47 min).

Scheme-22:

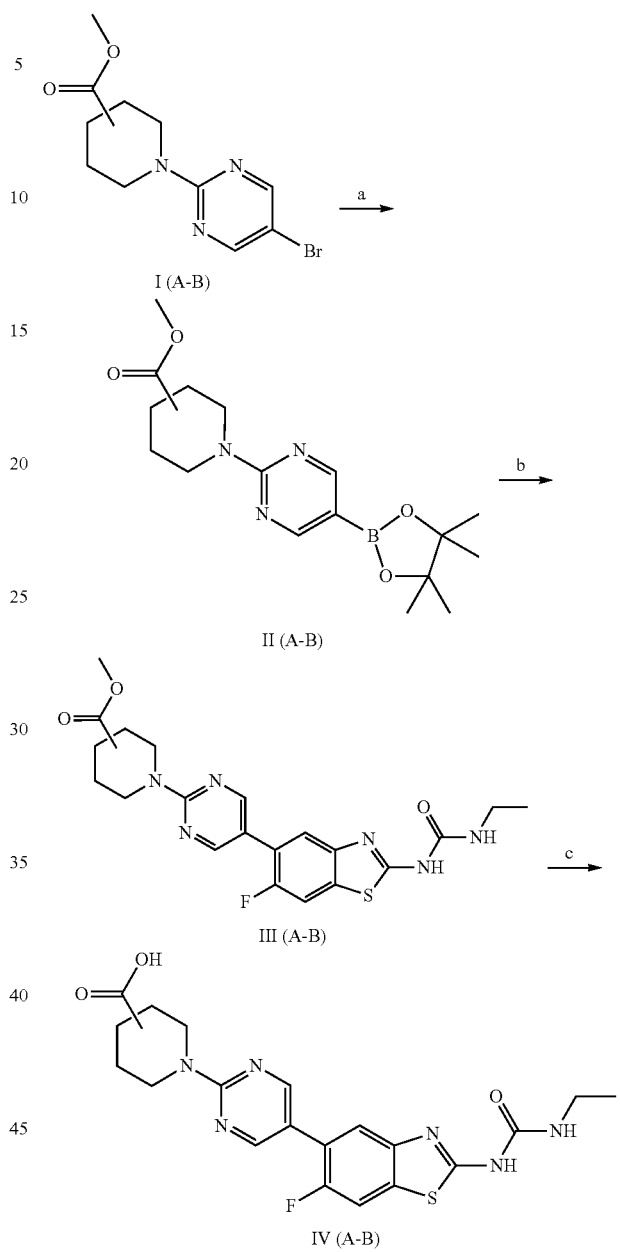

(a) Bispinacolatodiboron, KOAc, Pd$_2$(dba)$_3$, tricyclohexyphosphine, 1,4-dioxane;
(b) 1-(5-bromo-6-fluoro-benzothiazol-2-yl)-3-ethyl-urea, K$_3$PO$_4$, Dichlorobis(triphenylphosphine)-palladium(II), DMF—H$_2$O; (c) LiOH, THF-H$_2$O.

III-A = C-4 methyl ester
III-B = C-3 methyl ester
IV-A = C-4 carboxylic acid
IV-B = C-3 carboxylic acid

Preparation of methyl 1-(5-(4,4,5,5-tetramethyl-1,3,2-dioxaborolan-2-yl)pyrimidin-2-yl)piperidine-4-carboxylate (II-A)

A solution of methyl-1-(5-bromopyrimidin-2-yl)piperidine-4-carboxylate (0.32 g, 1.05 mmol), bispinacolatodiboron (0.32 g, 1.25 mmol) and KOAc (0.16 g, 1.60 mmol) in 1,4-dioxane (5.0 mL) was degassed by flushing with nitrogen for 15 min. Tricyclohexylphosphine (0.036 g, 0.13 mmol) and tris(dibenzyledineacetone)dipalladium(0) (0.05 g, 0.053 mmol) was then added to the reaction mixture, which was again degassed by nitrogen for 15 min. The resulting reaction mixture was heated to 100° C. for 4 h. After the completion of the reaction (TLC monitoring), the reaction mixture was filtered through celite bed and the filtrate was concentrated to get the crude residue that was carried forward to the next step without further purification. MS: 348.21 (M+H)$^+$.

Preparation of methyl 1-(5-(4,4,5,5-tetramethyl-1,3, 2-dioxaborolan-2-yl)pyrimidin-2-yl)piperidine-3-carboxylate (II-B)

A solution of methyl-1-(5-bromopyrimidin-2-yl)piperidine-3-carboxylate (0.10 g, 0.33 mmol), bispinacolatodiboron (0.102 g, 0.39 mmol) and KOAc (0.05 g, 0.49 mmol) in 1,4-dioxane (5.0 mL) was degassed by flushing with nitrogen for 15 min. Tricyclohexylphosphine (0.012 g, 0.04 mmol) and tris(dibenzyledineacetone)dipalladium(0) (0.016 g, 0.020 mmol) was then added to the reaction mixture, which was again degassed by nitrogen for 15 min. The resulting reaction mixture was heated to 100° C. for 5 h. After the completion of the reaction (TLC monitoring), the reaction mixture was filtered through celite bed and the filtrate was concentrated to get the crude residue that was carried forward to the next step without further purification. MS: 348.21 (M+H)$^+$.

Preparation of methyl 1-(5-(2-(3-ethylureido)-6-fluorobenzo[d]thiazol-5-yl)pyrimidin-2-yl)piperidine-4-carboxylate (III-A)

Example 43

A solution of 1-(5-bromo-6-fluoro-benzothiazol-2-yl)-3-ethyl-urea (0.20 g, 0.63 mmol), methyl 1-(5-(4,4,5,5-tetramethyl-1,3,2-dioxaborolan-2-yl)pyrimidin-2-yl)piperidine-4-carboxylate (0.33 g, 0.94 mmol) and $K_3PO_4$ (0.27 g, 1.26 mmol) in DMF-$H_2O$ (7.0 mL, 5:2) was degassed by flushing with nitrogen for 15 min.

Dichlorobis(triphenylphosphine)-palladium(II) (0.044 g, 0.06 mmol) was then added to the reaction mixture followed by degassing with nitrogen for another 15 min. The resulting reaction mixture was then heated to 100° C. for 2 h. After the completion of the reaction (TLC monitoring), the reaction mixture was cooled to room temperature and poured onto ice-cold water followed by extraction with EtOAc (2×50 mL). The combined organics was washed with brine, dried ($Na_2SO_4$), filtered and concentrated under reduced pressure. The crude was then purified over silica gel (100-200 M, 5% MeOH-DCM) to obtain the desired product (0.12 g, 42%). $^1$H-NMR (400 MHz, DMSO-$d_6$): δ 1.19 (t, J=7.20 Hz, 3H), 1.56 (m, 2H), 1.94 (m, 2H), 2.73 (s, 1H), 3.33 (m, 4H), 3.62 (s, 3H), 4.59 (s, 2H), 6.70 (br s, 1H), 7.75 (d, J=6.80 Hz, 1H), 7.91 (d, J=10.40 Hz, 1H), 8.59 (s, 2H) and 10.74 (br s, 1H). MS: 459.14 (M+H$^+$). Qualitative HPLC Purity (Acquity BEH C-18, 2.1×100 mm, 229 nm): 97.90% (Rt=6.14 min).

Preparation of 1-(5-(2-(3-ethylureido)-6-fluorobenzo[d]thiazol-5-yl)pyrimidin-2-yl)piperidine-4-carboxylic acid (IV-A)

Example 44

To a solution of methyl 1-(5-(2-(3-ethylureido)-6-fluorobenzo[d]thiazol-5-yl)pyrimidin-2-yl)piperidine-4-carboxylate (0.05 g, 0.11 mmol) in THF (3.0 mL) was added a solution of LiOH.$H_2O$ (0.014 g, 0.33 mmol) in $H_2O$ (1.0 mL). The resulting reaction mixture was heated to 60° C. for 16 h. After the completion of reaction (TLC monitoring), THF was distilled off, added water and extracted with EtOAc (2×25 mL) that was later on discarded. The aqueous layer was acidified with 1N HCl till pH 5-6 and then extracted with EtOAc (2×25 mL). The combined organics was washed with brine, dried ($Na_2SO_4$), filtered and concentrated to obtain the desired product (0.03 g, 62%). $^1$H-NMR (400 MHz, DMSO-$d_6$): δ 1.10 (t, J=7.20 Hz, 3H), 1.55 (m, 2H), 1.92 (m, 2H), 2.57 (m, 1H), 3.20 (m, 4H), 4.58 (m, 2H), 6.84 (br s, 1H), 7.75 (d, J=7.20 Hz, 1H), 7.91 (d, J=10.40 Hz, 1H), 8.59 (s, 2H), 10.84 (br s, 1H) and 12.30 (br s, 1H). MS: 443.07 (M−H)$^+$. Qualitative HPLC Purity (Acquity BEH C-18, 2.1×100 mm, 229 nm): 96.24% (Rt=4.34 min).

Preparation of methyl 1-(5-(2-(3-ethylureido)-6-fluorobenzo[d]thiazol-5-yl)pyrimidin-2-yl)piperidine-3-carboxylate (III-B)

Example 45

A solution of 1-(5-bromo-6-fluoro-benzothiazol-2-yl)-3-ethyl-urea (0.08 g, 0.25 mmol), methyl 1-(5-(4,4,5,5-tetramethyl-1,3,2-dioxaborolan-2-yl)pyrimidin-2-yl)piperidine-3-carboxylate (0.13 g, 0.37 mmol) and $K_3PO_4$ (0.106 g, 0.50 mmol) in DMF-$H_2O$ (7.0 mL, 5:2) was degassed by flushing with nitrogen for 15 min. Dichlorobis(triphenylphosphine)-palladium(II) (0.018 g, 0.025 mmol) was then added to the reaction mixture followed by degassing with nitrogen for another 15 min. The resulting reaction mixture was then heated to 85° C. for 7 h. After the completion of the reaction (TLC monitoring), the reaction mixture was cooled to room temperature and poured onto ice-cold water followed by extraction with EtOAc (2×50 mL). The combined organics was washed with brine, dried ($Na_2SO_4$), filtered and concentrated under reduced pressure. The crude was then purified over silica gel (100-200 M, 3% MeOH-DCM) to obtain the desired product (0.041 g, 36%). $^1$H-NMR (400 MHz, DMSO-$d_6$): δ 1.11 (t, J=7.20 Hz, 3H), 1.50 (m, 1H), 1.74 (m, 2H), 2.03 (m, 1H), 2.57 (m, 1H), 3.08-3.32 (m, 4H), 3.63 (s, 3H), 4.48 (d, J=12.40 Hz, 1H), 4.74 (dd, J=3.60 and 13.20 Hz, 1H), 6.70 (br s, 1H), 7.75 (d, J=6.80 Hz, 1H), 7.92 (d, J=10.40 Hz, 1H), 8.59 (s, 2H) and 10.74 (br s, 1H). MS: 459.14 (M+H$^+$). Qualitative HPLC Purity (Acquity BEH C-18, 2.1×100 mm, 229 nm): 98.31% (Rt=6.26 min).

Preparation of 1-(5-(2-(3-ethylureido)-6-fluorobenzo[d]thiazol-5-yl)pyrimidin-2-yl)piperidine-3-carboxylic acid (IV-B)

Example 46

To a solution of methyl 1-(5-(2-(3-ethylureido)-6-fluorobenzo[d]thiazol-5-yl)pyrimidin-2-yl)piperidine-3-carboxylate (0.05 g, 0.11 mmol) in THF (3.0 mL) was added a solution of LiOH.$H_2O$ (0.014 g, 0.33 mmol) in $H_2O$ (1.0 mL). The resulting reaction mixture was heated to 60° C. for 16 h. After the completion of reaction (TLC monitoring), THF was distilled off, added water and extracted with EtOAc (2×25 mL) that was later on discarded. The aqueous layer was acidified with 1N HCl till pH 5-6 and then extracted with EtOAc (2×25 mL). The combined organics was washed with brine, dried ($Na_2SO_4$), filtered and concentrated to obtain the desired product (0.03 g, 62%). $^1$H-NMR (400 MHz, DMSO-$d_6$): δ 1.11 (t, J=7.20 Hz, 3H), 1.49 (m, 1H), 1.74 (m, 2H), 2.02 (m, 1H), 2.41 (m, 1H), 3.04-3.21 (m, 4H), 4.51 (d, J=13.60 Hz, 1H), 4.71 (dd, J=3.20 and 12.80 Hz, 1H), 6.77 (br s, 1H), 7.75 (d, J=6.80 Hz, 1H), 7.91 (d, J=10.40 Hz, 1H), 8.60 (s, 2H), 10.74 (br s, 1H) and 12.50 (br s, 1H). MS: 445.12 (M+H$^+$). Qualitative HPLC Purity (Acquity BEH C-18, 2.1× 100 mm, 229 nm): 98.50% (Rt=4.42 min).

Scheme-23:

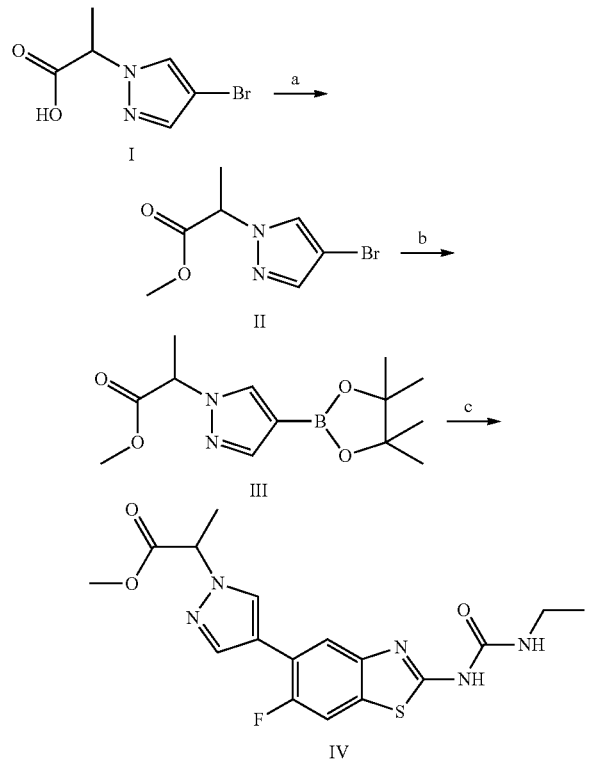

(a) MeOH—H$_2$SO$_4$; (b) Bispinacolatodiboron, KOAc, Pd$_2$(dba)$_3$, tricyclohexyphosphine, 1,4-dioxane; (b) 1-(5-bromo-6-fluoro-benzothiazol-2-yl)-3-ethyl-urea, K$_3$PO$_4$, Dichlorobis(triphenylphosphine)-palladium(II), DMF—H$_2$O.

Preparation of methyl 2-(4-bromo-1H-pyrazol-1-yl)propanoate (II)

To a solution of 2-(4-bromo-1H-pyrazol-1-yl)propanoic acid (0.20 g, 0.91 mmol) in MeOH (4.0 mL) was added conc H$_2$SO$_4$ (0.20 mL) and the resulting reaction mixture was heated to 68° C. for 2 h. After the completion of reaction (TLC monitoring), the solvent was evaporated and the residue was basified with saturated NaHCO$_3$ solution followed by extraction with EtOAc (3×25.0 mL). The combined organics was dried (Na$_2$SO$_4$), filtered and concentrated to obtain the desired product (0.175 g, 82%).

Preparation of methyl 2-(4-(4,4,5,5-tetramethyl-1,3,2-dioxaborolan-2-yl)-1H-pyrazol-1-yl)propanoate (III)

A solution of methyl 2-(4-bromo-1H-pyrazol-1-yl)propanoate (0.17 g, 0.73 mmol), bispinacolatodiboron (0.203 g, 0.80 mmol) and KOAc (0.107 g, 1.09 mmol) in 1,4-dioxane (7.0 mL) was degassed by flushing with nitrogen for 15 min. Tricyclohexylphosphine (0.024 g, 0.087 mmol) and tris(dibenzyledineacetone)dipalladium(0) (0.038 g, 0.036 mmol) was then added to the reaction mixture, which was again degassed by nitrogen for 15 min. The resulting reaction mixture was heated to 100° C. for 2 h. After the completion of the reaction (TLC monitoring), the reaction mixture was filtered through celite bed and the filtrate was concentrated to get the crude residue that was carried forward to the next step without further purification. MS: 281.10 (M+H)$^+$.

Preparation of methyl 2-(4-(2-(3-ethylureido)-6-fluorobenzo[d]thiazol-5-yl)-1H-pyrazol-1-yl)propanoate (IV)

Example 47

A solution of 1-(5-bromo-6-fluoro-benzothiazol-2-yl)-3-ethyl-urea (0.094 g, 0.29 mmol), methyl 2-(4-(4,4,5,5-tetramethyl-1,3,2-dioxaborolan-2-yl)-1H-pyrazol-1-yl)propanoate (0.164 g, 0.58 mmol) and K$_3$PO$_4$ (0.125 g, 0.59 mmol) in DMF-H$_2$O (7.0 mL, 5:2) was degassed by flushing with nitrogen for 15 min. Dichlorobis(triphenylphosphine)-palladium(II) (0.020 g, 0.03 mmol) was then added to the reaction mixture followed by degassing with nitrogen for another 15 min. The resulting reaction mixture was then heated to 90° C. for 4 h. After the completion of the reaction (TLC monitoring), the reaction mixture was cooled to room temperature and poured onto ice-cold water followed by extraction with EtOAc (2×50 mL). The combined organics was washed with brine, dried (Na$_2$SO$_4$), filtered and concentrated under reduced pressure. The crude was then purified over silica gel (100-200 M, 1.50% MeOH-DCM) to obtain the desired product (0.025 g, 22%). $^1$H-NMR (400 MHz, DMSO-d$_6$): δ 1.10 (t, J=7.20 Hz, 3H), 1.71 (d, J=7.20 Hz, 3H), 3.20 (m, 2H), 3.66 (s, 3H), 5.38 (q, J=7.20 Hz, 1H), 6.71 (br s, 1H), 7.85 (d, J=10.80 Hz, 1H), 7.95 (d, J=6.40 Hz, 1H), 8.02 (s, 1H), 8.30 (s, 1H) and 10.73 (br s, 1H). MS: 390.11 (M−H)$^+$. Qualitative HPLC Purity (Acquity BEH C-18, 2.1× 100 mm, 249 nm): 98.36% (Rt=5.32 min).

Scheme-24:

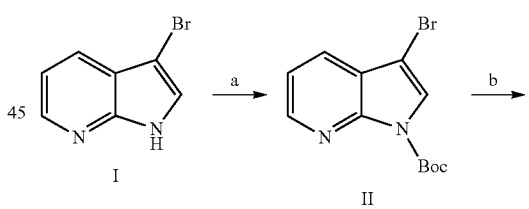

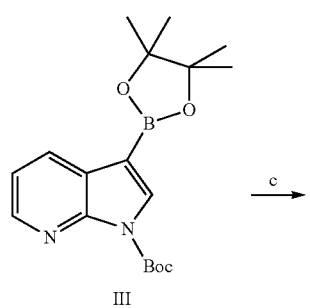

-continued

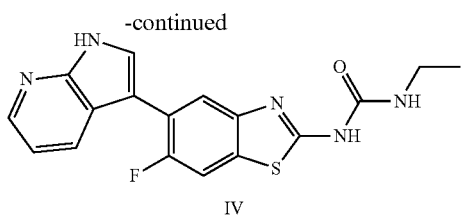

IV (a) Boc anhydride, DMAP, THF; (b) Bispinacolatodiboron, KOAc, Pd₂(dba)₃, tricyclohexyphosphine, 1,4-dioxane; (c) 1-(5-bromo-6-fluoro-benzothiazol-2-yl)-3-ethyl-urea, K₃PO₄, Dichlorobis(triphenylphosphine)-palladium(II), DMF—H₂O.

Preparation of tert-butyl 3-bromo-1H-pyrrolo[2,3-b]pyridine-1-carboxylate (II)

To a solution of 3-bromo-1-H-pyrrolo[2,3-b]pyridine (0.10 g, 0.50 mmol) in THF (4.0 mL) under nitrogen atmosphere was added DMAP (0.006 g, 0.06 mmol). The resulting reaction mixture was cooled to −20° C. followed by addition of Boc anhydride (122 μL, 0.56 mmol). The reaction mixture was then allowed to warm upto room temperature and stirred for 2 h. After the completion of reaction (TLC monitoring), water (20 mL) was added to the reaction mixture and then extracted with EtOAc (3×50 mL). The combined organics was dried (Na₂SO₄), filtered and concentrated. The residue was purified over silica gel (60-120 M, 5% EtOAc-Hexane) to obtain the desired product as oily mass (0.12 g, 79%).

Preparation of tert-butyl 3-(4,4,5,5-tetramethyl-1,3,2-dioxaborolan-2-yl)-1H-pyrrolo[2,3-b]pyridine-1-carboxylate (III)

A solution of tert-butyl 3-bromo-1H-pyrrolo[2,3-b]pyridine-1-carboxylate (0.115 g, 0.38 mmol), bispinacolatodiboron (0.108 g, 0.42 mmol) and KOAc (0.056 g, 0.58 mmol) in 1,4-dioxane (4.0 mL) was degassed by flushing with nitrogen for 15 min. Tricyclohexylphosphine (0.013 g, 0.046 mmol) and tris(dibenzyledineacetone)dipalladium(0) (0.021 g, 0.019 mmol) was then added to the reaction mixture, which was again degassed by nitrogen for 15 min. The resulting reaction mixture was heated to 100° C. for 6 h. After the completion of the reaction (TLC monitoring), the reaction mixture was filtered through celite bed and the filtrate was concentrated to get the crude residue that was carried forward to the next step without further purification. MS: 345.10 (M+H)⁺.

Preparation of 1-ethyl-3-(6-fluoro-5-(1H-pyrrolo[2,3-b]pyridin-3-yl)benzo[d]thiazol-2-yl)urea (IV)

Example 48

A solution of 1-(5-bromo-6-fluoro-benzothiazol-2-yl)-3-ethyl-urea (0.049 g, 0.15 mmol), tert-butyl 3-(4,4,5,5-tetramethyl-1,3,2-dioxaborolan-2-yl)-1H-pyrrolo[2,3-b]pyridine-1-carboxylate (0.106 g, 0.31 mmol) and K₃PO₄ (0.065 g, 0.31 mmol) in DMF-H₂O (7.0 mL, 5:2) was degassed by flushing with nitrogen for 15 min. Dichlorobis(triphenylphosphine)-palladium(II) (0.011 g, 0.015 mmol) was then added to the reaction mixture followed by degassing with nitrogen for another 15 min. The resulting reaction mixture was then heated to 95° C. for 4 h. After the completion of the reaction (TLC monitoring), the reaction mixture was cooled to room temperature and poured onto ice-cold water followed by extraction with EtOAc (2×50 mL). The combined organics was washed with brine, dried (Na₂SO₄), filtered and concentrated under reduced pressure. The crude was then purified over silica gel (100-200 M, 2.50% MeOH-DCM) to obtain the desired de-Boc product (0.016 g, 29%). ¹H NMR (DMSO-d6, 400 MHz): δ 1.11 (t, J=7.20 Hz, 3H), 3.20 (m, 2H), 6.79 (br s, 1H), 7.17 (m, 1H), 7.83 (m, 2H), 7.93 (m, 1H), 8.08 (d, J=8.00 Hz, 1H), 8.29 (d, J=1.20 Hz, 1H), 10.80 (br s, 1H) and 12.03 (br s, 1H). MS: 356.13 (M+H⁺). Qualitative HPLC Purity (Acquity BEH C-18, 2.1×100 mm, 223 nm): 90.90% (Rt=5.17 min).

Scheme-25:

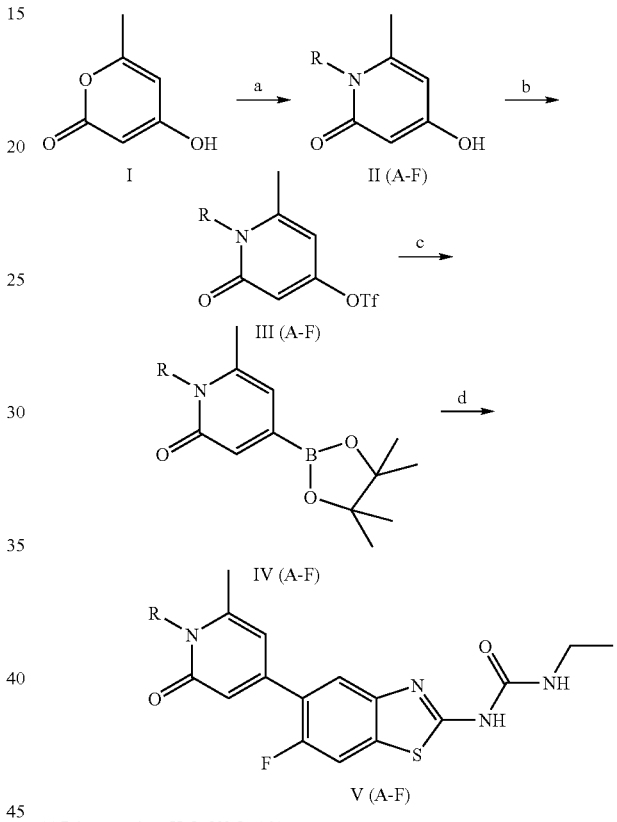

(a) Primary amines, H₂O, 80° C., 16 h;
(b) N-phenylbis(trifluoromethanesulfonimide), DIPEA, DMF, room temperature, 2 h;
(c) Bispinacolatodiboron, KOAc, Pd₂(dba)₃, tricyclohexyphosphine, 1,4-dioxane;
(d) 1-(5-bromo-6-fluoro-benzothiazol-2-yl)-3-ethyl-urea, K₃PO₄, Dichlorobis(triphenylphosphine)-palladium(II), DMF—H₂O.

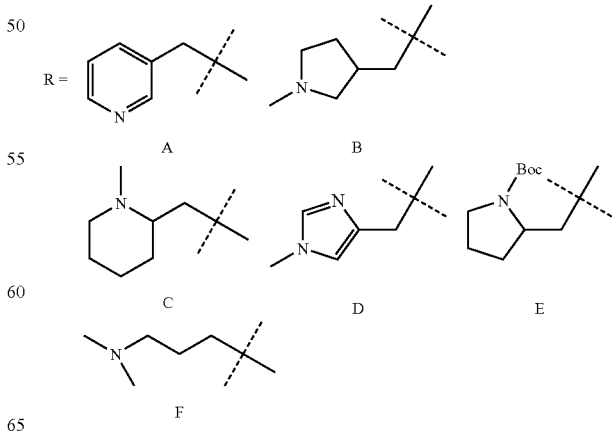

General Procedure for the Preparation of Substituted Cyclic Amides (II)

A mixture of 6-methyl-4-hydroxy pyranone (1.0 eq) and primary amine (1.20 eq) in water (5 times dilution by weight) was heated to 80° C. for 16 h. After the completion of reaction (TLC monitoring) the precipitated solid was filtered, washed with ether and dried under vacuum to obtain the desired product (around 75% yield).

General Procedure for the Preparation of Triflates (III)

To a solution of cyclic amide II (1.0 eq) in DMF was added DIPEA (1.15 eq) and the resulting mixture was stirred at room temperature for 15 min followed by addition of N-phenylbis(trifluoromethanesulfonimide) (1.20 eq). The resulting reaction mixture was continued to stir at room temperature for 2 h. After the completion of reaction (TLC monitoring), the reaction mixture was poured onto the ice-cold water and extracted with EtOAc (3×100 mL). The combined organics was washed with brine, dried over $Na_2SO_4$, filtered and concentrated under reduced pressure to obtain the desired product that was carried forward to the next step without further purification.

General Procedure for the Preparation of Boronates (IV)

To a solution of triflate III (1.0 eq) in 1,4-dioxane (10 times dilution by weight) was added bis(pinacolato)diboron (2.0 eq) followed by KOAc (3.0 eq). The resulting solution was degassed by nitrogen for 15 min followed by addition of tricyclohexylphosphine (0.15 eq) and tris(dibenzylideneacetone)dipalladium(0) (0.10 eq). The resulting reaction mixture was again degassed by nitrogen for 15 min and then heated to 80° C. for 2 h. After the completion of reaction (TLC monitoring), the reaction mixture was diluted by EtOAc and filtered through celite bed. The filtrate was concentrated and used as such for the next step without further purification.

Preparation of 1-ethyl-3-(6-fluoro-5-(6-methyl-2-oxo-1-(pyridin-3-ylmethyl)-1,2-dihydropyridin-4-yl)benzo[d]thiazol-2-yl)urea (V-A)

Example 49

A solution of 1-(5-bromo-6-fluoro-benzothiazol-2-yl)-3-ethyl-urea (0.30 g, 0.94 mmol), 6-methyl-1-(pyridin-3-ylmethyl)-4-(4,4,5,5-tetramethyl-1,3,2-dioxaborolan-2-yl)pyridin-2(1H)-one IV-A (0.47 g, 1.43 mmol) and $K_3PO_4$ (0.40 g, 1.88 mmol) in DMF-$H_2O$ (14.0 mL, 5:2) was degassed by flushing with nitrogen for 15 min. Dichlorobis(triphenylphosphine)-palladium(II) (0.065 g, 0.090 mmol) was then added to the reaction mixture followed by degassing with nitrogen for another 15 min. The resulting reaction mixture was then heated to 80° C. for 3 h. After the completion of the reaction (TLC monitoring), the reaction mixture was cooled to room temperature and poured onto ice-cold water followed by extraction with EtOAc (2×100 mL). The combined organics was washed with brine, dried ($Na_2SO_4$), filtered and concentrated under reduced pressure. The crude was then purified over silica gel (100-200 M, 7.0% MeOH-DCM) to obtain the desired product (0.25 g, 61%). $^1$H-NMR (400 MHz, DMSO-$d_6$): δ 1.08 (t, J=7.20 Hz, 3H), 2.37 (s, 3H), 3.20 (m, 2H), 5.34 (s, 2H), 6.48 (s, 1H), 6.58 (s, 1H), 6.70 (br s, 1H), 7.38 (m, 1H), 7.59 (d, J=8.0 Hz, 1H), 7.77 (d, J=6.40 Hz, 1H), 7.95 (d, J=10.80 Hz, 1H), 8.50 (s, 2H) and 10.87 (br s, 1H). MS: 438.07 (M+H)$^+$. Qualitative HPLC Purity (Acquity BEH C-18, 100×2.1 mm, 240 nm): 99.13% (Rt=4.94 min).

Preparation of 1-ethyl-3-(6-fluoro-5-(6-methyl-1-((1-methylpyrrolidin-3-yl)methyl)-2-oxo-1,2-dihydropyridin-4-yl)benzo[d]thiazol-2-yl)urea (V-B)

Example 50

A solution of 1-(5-bromo-6-fluoro-benzothiazol-2-yl)-3-ethyl-urea (0.066 g, 0.20 mmol), 6-methyl-1-((1-methylpyrrolidin-3-yl)methyl)-4-(4,4,5,5-tetramethyl-1,3,2-dioxaborolan-2-yl)pyridin-2(1H)-one IV-B (0.14 g, 0.41 mmol) and $K_3PO_4$ (0.088 g, 0.41 mmol) in DMF-$H_2O$ (8.0 mL, 5:3) was degassed by flushing with nitrogen for 15 min. Dichlorobis(triphenylphosphine)-palladium(II) (0.015 g, 0.02 mmol) was then added to the reaction mixture followed by degassing with nitrogen for another 15 min. The resulting reaction mixture was then heated to 80-90° C. for 4-5 h. After the completion of the reaction (TLC monitoring), the reaction mixture was cooled to room temperature and poured onto ice-cold water followed by extraction with EtOAc (4×50 mL). The combined organics was washed with brine, dried ($Na_2SO_4$), filtered and concentrated under reduced pressure. The crude was then purified over silica gel (230-400 M, 8.0-10.0% MeOH-DCM) to obtain the desired product (0.005 g, 5%). $^1$H-NMR (400 MHz, DMSO-$d_6$): δ 1.08 (t, J=7.20 Hz, 3H), 1.50 (m, 2H), 1.87 (m, 1H), 2.23 (s, 3H), 2.31 (m, 2H), 2.49 (s, 3H), 2.62 (m, 1H), 3.19 (m, 4H), 3.97 (m, 1H), 6.40 (s, 1H), 6.45 (s, 1H), 6.91 (br s, 1H), 7.72 (d, J=6.80 Hz, 1H), 7.93 (d, J=10.80 Hz, 1H), and 11.0 (br s, 1H). MS: 441.15 (M+H)$^+$. Qualitative HPLC Purity (Acquity BEH C-18, 100×2.1 mm, 240 nm): 85.59% (Rt=4.45 min).

Preparation of 1-ethyl-3-(6-fluoro-5-(6-methyl-1-((1-methylpiperidin-2-yl)methyl)-2-oxo-1,2-dihydropyridin-4-yl)benzo[d]thiazol-2-yl)urea (V-C)

Example 51

A solution of 1-(5-bromo-6-fluoro-benzothiazol-2-yl)-3-ethyl-urea (0.075 g, 0.24 mmol), 6-methyl-1-((1-methylpiperidin-2-yl)methyl)-4-(4,4,5,5-tetramethyl-1,3,2-dioxaborolan-2-yl)pyridin-2(1H)-one IV-C (0.164 g, 0.47 mmol) and $K_3PO_4$ (0.10 g, 0.47 mmol) in DMF-$H_2O$ (8.0 mL, 5:1) was degassed by flushing with nitrogen for 15 min. Dichlorobis (triphenylphosphine)-palladium(II) (0.016 g, 0.023 mmol) was then added to the reaction mixture followed by degassing with nitrogen for another 15 min. The resulting reaction mixture was then heated to 90° C. for 2 h. After the completion of the reaction (TLC monitoring), the reaction mixture was cooled to room temperature and poured onto ice-cold water followed by extraction with EtOAc (4×50 mL). The combined organics was washed with brine, dried ($Na_2SO_4$), filtered and concentrated under reduced pressure. The crude was then purified over silica gel (230-400 M, 7.0-8.0% MeOH-DCM) to obtain the desired product (0.044 g, 41%). $^1$H-NMR (400 MHz, DMSO-$d_6$): δ 1.08 (t, J=7.20 Hz, 3H), 1.21 (m, 2H), 1.33 (m, 2H), 1.52 (m, 2H), 1.64 (m, 1H), 2.47 (s, 3H), 2.94 (m, 1H), 3.20 (m, 3H), 3.30 (s, 3H), 4.24 (m, 2H), 6.44 (s, 1H), 6.47 (s, 1H), 6.76 (br s, 1H), 7.73 (d, J=6.40 Hz, 1H), 7.94 (d, J=10.80 Hz, 1H) and 10.89 (br s, 1H). MS: 458.13 (M+H)$^+$. Qualitative HPLC Purity (Acquity BEH C-18, 100×2.1 mm, 240 nm): 97.87% (Rt=4.77 min).

Preparation of 1-ethyl-3-(6-fluoro-5-(6-methyl-1-((1-methyl-1H-imidazol-4-yl)methyl)-2-oxo-1,2-dihydropyridin-4-yl)benzo[d]thiazol-2-yl)urea (V-D)

Example 52

A solution of 1-(5-bromo-6-fluoro-benzothiazol-2-yl)-3-ethyl-urea (0.077 g, 0.24 mmol), 6-methyl-1-((1-methyl-1H- imidazol-4-yl)methyl)-4-(4,4,5,5-tetramethyl-1,3,2-dioxaborolan-2-yl)pyridin-2(1H)-one IV-D (0.16 g, 0.48 mmol) and K$_3$PO$_4$ (0.103 g, 0.48 mmol) in DMF-H$_2$O (4.0 mL, 3:1) was degassed by flushing with nitrogen for 15 min. Dichlorobis(triphenylphosphine)-palladium(II) (0.017 g, 0.024 mmol) was then added to the reaction mixture followed by degassing with nitrogen for another 15 min. The resulting reaction mixture was then heated to 90° C. for 2 h. After the completion of the reaction (TLC monitoring), the reaction mixture was cooled to room temperature and poured onto ice-cold water followed by extraction with EtOAc (2×20 mL). The combined organics was washed with brine, dried (Na$_2$SO$_4$), filtered and concentrated under reduced pressure. The crude was then purified over silica gel (230-400 M, 4.0% MeOH-DCM) to obtain the desired product (0.019 g, 56%). $^1$H-NMR (400 MHz, DMSO-d$_6$): δ 1.08 (t, J=7.20 Hz, 3H), 2.63 (s, 3H), 3.18 (m, 2H), 3.59 (s, 3H), 5.06 (s, 2H), 6.36 (s, 1H), 6.43 (s, 1H), 6.69 (br s, 1H), 7.01 (br s, 1H), 7.48 (br s, 1H), 7.70 (d, J=6.80 Hz, 1H), 7.92 (d, J=10.40 Hz, 1H) and 10.80 (br s, 1H). MS: 441.26 (M+H)$^+$. Qualitative HPLC Purity (Acquity BEH C-18, 100×2.1 mm, 240 nm): 98.35% (Rt=4.76 min).

Preparation of tert-butyl 2-((4-(2-(3-ethylureido)-6-fluorobenzo[d]thiazol-5-yl)-6-methyl-2-oxopyridin-1(2H)-yl)methyl)pyrrolidine-1-carboxylate (V-E)

Example 53

A solution of 1-(5-bromo-6-fluoro-benzothiazol-2-yl)-3-ethyl-urea (0.07 g, 0.22 mmol), tert-butyl 2-((6-methyl-2-oxo-4-(4,4,5,5-tetramethyl-1,3,2-dioxaborolan-2-yl)pyridin-1(2H)-yl)methyl)pyrrolidine-1-carboxylate IV-E (0.184 g, 0.44 mmol) and K$_3$PO$_4$ (0.094 g, 0.44 mmol) in DMF-H$_2$O (5.0 mL, 3:2) was degassed by flushing with nitrogen for 15 min. Dichlorobis(triphenylphosphine)-palladium(II) (0.014 g, 0.02 mmol) was then added to the reaction mixture followed by degassing with nitrogen for another 15 min. The resulting reaction mixture was then heated to 80° C. for 2 h. After the completion of the reaction (TLC monitoring), the reaction mixture was cooled to room temperature and poured onto ice-cold water followed by extraction with EtOAc (2×25 mL). The combined organics was washed with brine, dried (Na$_2$SO$_4$), filtered and concentrated under reduced pressure. The crude was then purified over silica gel (100-200 M, 5.0% MeOH-DCM) to obtain the desired product (0.02 g, 17%). $^1$H-NMR (400 MHz, DMSO-d$_6$): δ 1.08 (t, J=7.20 Hz, 3H), 1.23 (s, 9H), 1.74-1.85 (m, 4H), 2.02 (m, 1H), 2.41 (s, 3H), 3.20 (m, 2H), 3.89 (m, 1H), 4.03 (m, 1H), 4.21 (br s, 1H), 4.33 (br s, 1H), 6.39-6.45 (m, 2H), 6.70 (br s, 1H), 7.67 (d, J=6.80 Hz, 1H), 7.93 (d, J=10.40 Hz, 1H) and 10.82 (br s, 1H). MS: 530.21 (M+H)$^+$. Qualitative HPLC Purity (Acquity BEH C-18, 100×2.1 mm, 259 nm): 97.62% (Rt=5.73 min).

Preparation of 1-(5-(1-(3-(dimethylamino)propyl)-6-methyl-2-oxo-1,2-dihydropyridin-4-yl)-6-fluorobenzo[d]thiazol-2-yl)-3-ethylurea (V-F)

Example 54

A solution of 1-(5-bromo-6-fluoro-benzothiazol-2-yl)-3-ethyl-urea (0.08 g, 0.25 mmol), 1-(3-(dimethylamino)propyl)-6-methyl-4-(4,4,5,5-tetramethyl-1,3,2-dioxaborolan-2-yl)pyridin-2(1H)-one IV-F (0.16 g, 0.50 mmol) and K$_3$PO$_4$ (0.106 g, 0.50 mmol) in DMF-H$_2$O (7.0 mL, 4:3) was degassed by flushing with nitrogen for 15 min. Dichlorobis(triphenylphosphine)-palladium(II) (0.018 g, 0.02 mmol) was then added to the reaction mixture followed by degassing with nitrogen for another 15 min. The resulting reaction mixture was then heated to 90° C. for 1 h. After the completion of the reaction (TLC monitoring), the reaction mixture was cooled to room temperature and poured onto ice-cold water followed by extraction with EtOAc (2×25 mL). The combined organics was washed with brine, dried (Na$_2$SO$_4$), filtered and concentrated under reduced pressure. The crude was then purified over silica gel (100-200 M, 9.0% MeOH-DCM saturated with 1% aq NH$_3$) to obtain the desired product (0.02 g, 19%). $^1$H-NMR (400 MHz, DMSO-d$_6$): δ 1.08 (t, J=7.20 Hz, 3H), 1.81 (m, 2H), 2.29 (s, 6H), 2.46 (m, 5H), 3.20 (m, 2H), 3.99 (m, 2H), 6.41 (s, 1H), 6.45 (s, 1H), 6.78 (br s, 1H), 7.71 (d, J=6.80 Hz, 1H), 7.93 (d, J=10.40 Hz, 1H) and 10.85 (br s, 1H). MS: 432.16 (M+H)$^+$. Qualitative HPLC Purity (Acquity BEH C-18, 100×2.1 mm, 238 nm): 96.96% (Rt=4.37 min).

Scheme-26:

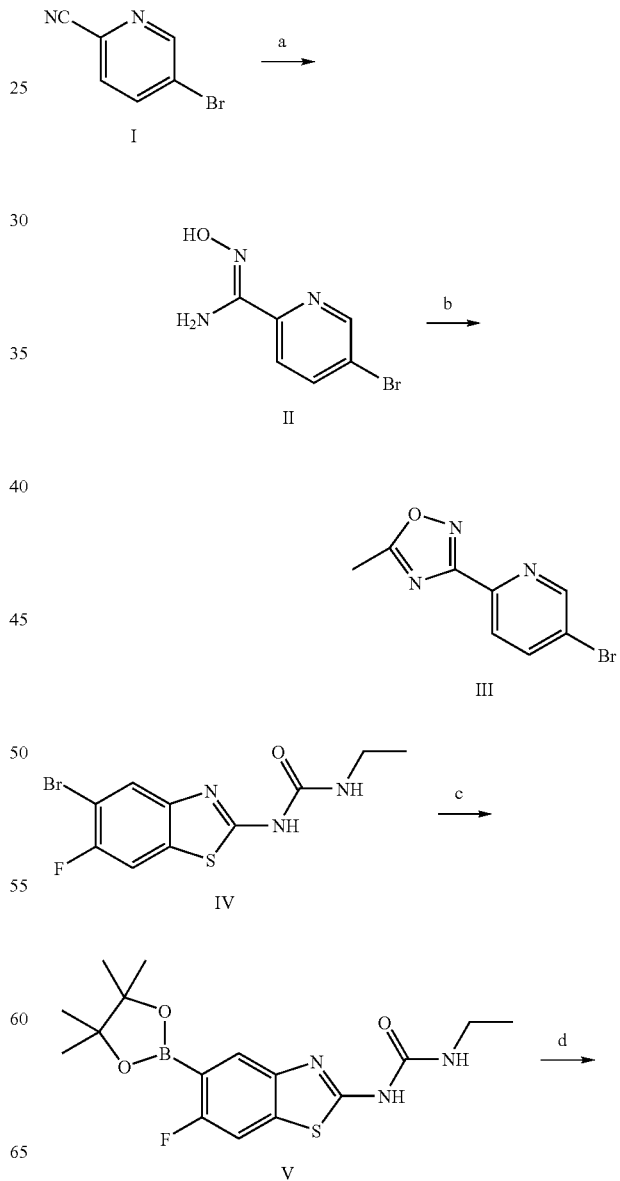

-continued

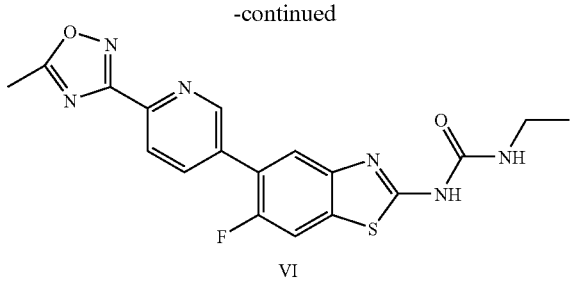

VI (a) NH$_2$OH·HCl, NaOH, EtOH, 60-65° C., 16 h; (b) acetic acid, acetic anhydride, 100° C., 2 h; (c) Bispinacolatodiboron, KOAc, Pd$_2$(dba)$_3$, tricyclohexyphosphine, 1,4-dioxane; (d) 3-(5-bromopyridin-2-yl)-5-methyl-1,2,4- oxadiazole III, K$_3$PO$_4$, Dichlorobis(triphenylphosphine)-palladium(II), DMF—H$_2$O.

Preparation of 5-bromo-N'-hydroxypicolinimidamide (II)

To a solution of 5-bromo-2-cyanopyridine (1.0 g, 5.50 mmol) in EtOH (100.0 mL) was added a solution of NaOH (0.22 g, 5.50 mmol dissolved in 2.0 ml H$_2$O) followed by addition of NH$_2$OH.HCl (0.38 g, 5.50 mmol). The resulting solution was heated to 60-65° C. for 16 h. After the completion of reaction (TLC monitoring), the solvent was evaporated and the residue was acidified with 3% HCl solution (20.0 mL) and heated to 100° C. till a clear solution was obtained. The reaction mixture was then cooled to room temperature and extracted with DCM (2×50 mL) that was later on discarded. The aqueous layer was basified with aqueous NH$_3$ till pH 8 and extracted with EtOAc (3×50 mL). The combined organics was dried (Na$_2$SO$_4$), filtered and concentrated to obtain the desired product (0.75 g, 64%). MS: 216.01 (M+H)$^+$.

Preparation of 3-(5-bromopyridin-2-yl)-5-methyl-1,2,4-oxadiazole (III)

To a solution of 5-bromo-N'-hydroxypicolinimidamide II (0.75 g, 3.50 mmol) in acetic acid (50.0 mL) was added acetic anhydride (0.75 mL, 7.0 mmol) and the resulting reaction mixture was heated to 100° C. for 2 h. After the completion of reaction (TLC monitoring), acetic acid was distilled off, added water (25.0 mL) and extracted with EtOAc (2×50 mL). The combined organics was washed with brine, dried (Na$_2$SO$_4$), filtered and concentrated to obtain the desired product (0.27 g, 45%). MS: 240.01 (M+H)$^+$.

Preparation of 1-ethyl-3-(6-fluoro-5-(4,4,5,5-tetramethyl-1,3,2-dioxaborolan-2-yl)benzo[d]thiazol-2-yl) urea (V)

A solution of 1-(5-bromo-6-fluoro-benzothiazol-2-yl)-3-ethyl-urea (0.135 g, 0.42 mmol), bispinacolatodiboron (0.19 g, 0.47 mmol) and KOAc (0.065 g, 0.64 mmol) in 1,4-dioxane (10.0 mL) was degassed by flushing with nitrogen for 15 min. Tricyclohexylphosphine (0.015 g, 0.05 mmol) and tris(dibenzylideneacetone)dipalladium(0) (0.02 g, 0.02 mmol) was then added to the reaction mixture, which was again degassed by nitrogen for 15 min. The resulting reaction mixture was heated to 100° C. for 3 h. After the completion of the reaction (TLC monitoring), the reaction mixture was filtered through celite bed and the filtrate was concentrated to get the crude residue that was carried forward to the next step without further purification. MS: 365.10 (M+H)$^+$.

Preparation of 1-ethyl-3-(6-fluoro-5-(6-(5-methyl-1,2,4-oxadiazol-3-yl)pyridin-3-yl)benzo[d]thiazol-2-yl)urea (VI)

Example 55

A solution of 3-(5-bromopyridin-2-yl)-5-methyl-1,2,4-oxadiazole III (0.070 g, 0.30 mmol), 1-ethyl-3-(6-fluoro-5-(4,4,5,5-tetramethyl-1,3,2-dioxaborolan-2-yl)benzo[d]thiazol-2-yl)urea V (0.11 g, 0.30 mmol) and K$_3$PO$_4$ (0.077 g, 0.36 mmol) in DMF-H$_2$O (7.0 mL, 5:2) was degassed by flushing with nitrogen for 15 min. Dichlorobis(triphenylphosphine)-palladium(II) (0.04 g, 0.05 mmol) was then added to the reaction mixture followed by degassing with nitrogen for another 15 min. The resulting reaction mixture was then heated to 95-100° C. for 16 h. After the completion of the reaction (TLC monitoring), the reaction mixture was cooled to room temperature and poured onto ice-cold water followed by extraction with EtOAc (2×100 mL). The combined organics was washed with brine, dried (Na$_2$SO$_4$), filtered and concentrated under reduced pressure. The crude was then purified over silica gel (100-200 M, 2.50-3.0% MeOH-DCM) to obtain the desired product (0.011 g, 9%). $^1$H-NMR (400 MHz, DMSO-d$_6$): δ 1.09 (t, J=7.20 Hz, 3H), 2.71 (s, 3H), 3.19 (quintet, J=7.20 Hz, 2H), 6.72 (br s, 1H), 7.90 (d, J=6.80 Hz, 1H), 8.02 (d, J=10.40 Hz, 1H), 8.16 (m, 1H), 8.24 (m, 1H), 8.98 (s, 1H) and 10.84 (br s, 1H). MS: 399.09 (M+H)$^+$. Qualitative HPLC Purity (Acquity BEH C-18, 100×2.1 mm, 262 nm): 85.87% (Rt=5.44 min).

Scheme-27:

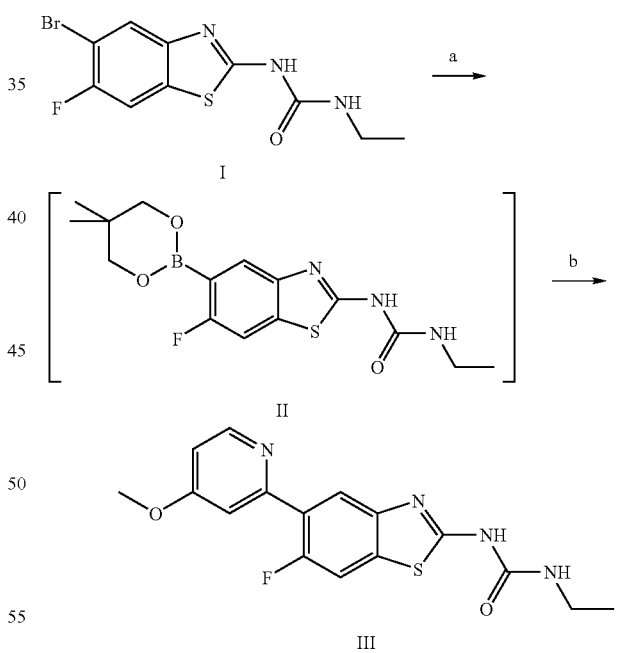

(a) Bis(neopentylglycolato) diboron, KOAc, PdCl$_2$(dppf), DMSO, 80° C., 3 h (b) 2-chloro-4-methoxy-pyridine, Cs$_2$CO$_3$, Pd(PPh$_3$)$_4$, DMSO, 80° C., 16 h.

Preparation of 1-ethyl-3-[6-fluoro-5-(4-methoxy-pyridin-2-yl)-benzothiazol-2-yl]-urea (III)

Example 56

To a solution of 1-(5-bromo-6-fluoro-benzothiazol-2-yl)-3-ethyl-urea (I) (0.15 g, 0.47 mmol) in DMSO (5 mL) was added KOAc (0.14 g, 1.41 mmol) and bis(neopentyl glycolato)diboron (0.21 g, 0.94 mmol) at room temperature. The resulting mixture was degassed for 15-20 min. by purging nitrogen followed by the addition of PdCl$_2$.dppf (0.013 g, 0.02 mmol). The reaction mixture was again degassed for 15-20 min and then heated up to 80° C. for 3 h. After completion of reaction (TLC monitoring), the reaction mixture was cooled to room temperature followed by in-situ addition of 2-chloro-4-methoxy-pyridine (0.035 g, 0.24 mmol) and Cs$_2$CO$_3$ (0.08 g, 3.70 M in H$_2$O). The resulting reaction mixture was degassed for 10-15 min. followed by the addition of Pd(PPh$_3$)$_4$ (0.20 g, 0.02 mmol). The resulting reaction mixture was finally degassed for 15-20 min and heated to 80° C. for 16 h. After completion of reaction (TLC monitoring), water was added to the reaction mixture and extracted with ethyl acetate (3×50 mL). The combined organics was dried over Na$_2$SO$_4$ and evaporated. The crude residue was purified over silica-gel (230-400 M, 2-3% MeOH-DCM to obtain the desired product as beige-solid (0.07 g, 4.3%). $^1$H-NMR (400 MHz, DMSO-d$_6$): δ 1.08 (t, J=7.20 Hz, 3H), 3.19 (m, 2H), 3.89 (s, 3H), 6.69 (br s, 1H), 7.02 (d, J=3.60 Hz, 1H), 7.33 (s, 1H), 7.93 (d, J=10.80 Hz, 1H), 8.06 (d, J=6.00 Hz, 1H), 8.54 (d, J=5.60 Hz, 1H) and 10.86 (br s, 1H). MS: 347.12 (M+H$^+$). Qualitative HPLC Purity (Acquity BEH C-18, 2.1×100 mm, 247 nm): 98.52% (Rt=5.07 min).

Scheme-28:

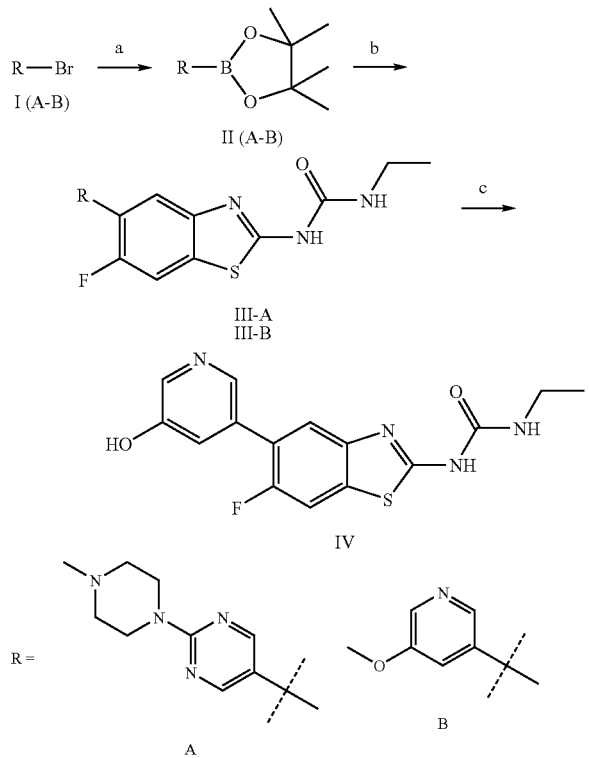

(a) Corresponding bromide, Bispinacolatodiboron, KOAc, tricyclohexylphosphine, Pd$_2$(dba)$_3$, 1,4-dioxane; (b) 1-(5-bromo-6-fluoro-benzothiazol-2-yl)-3-ethyl-urea, K$_3$PO$_4$, Dichlorobis(triphenylphosphine)-palladium(II), DMF—H$_2$O; (c) BBr$_3$-DCM, -78° C.

Preparation of 2-(4-methylpiperazin-1-yl)-5-(4,4,5,5-tetramethyl-1,3,2-dioxaborolan-2-yl)pyrimidine (II-A)

A solution of 5-bromo-2-(4-methylpiperazin-1-yl)pyrimidine (0.25 g, 0.98 mmol), bispinacolatodiboron (0.27 g, 1.07 mmol) and KOAc (0.12 g, 1.46 mmol) in 1,4-dioxane (5.0 mL) was degassed by flushing with nitrogen for 15 min. Tricyclohexylphosphine (0.027 g, 0.096 mmol) and tris(dibenzyledineacetone)dipalladium(0) (0.044 g, 0.048 mmol) was then added to the reaction mixture, which was again degassed by nitrogen for 15 min. The resulting reaction mixture was heated to 80° C. for 2 h. After the completion of the reaction (TLC monitoring), the reaction mixture was filtered through celite bed and the filtrate was concentrated to get the crude residue that was carried forward to the next step without further purification. MS: 305.20 (M+H)$^+$.

Preparation of 3-methoxy-5-(4,4,5,5-tetramethyl-1,3,2-dioxaborolan-2-yl)pyridine (II-B)

A solution of 3-bromo-5-methoxypyridine (0.10 g, 0.53 mmol), bispinacolatodiboron (0.15 g, 0.59 mmol) and KOAc (0.078 g, 0.80 mmol) in 1,4-dioxane (8.0 mL) was degassed by flushing with nitrogen for 15 min. Tricyclohexylphosphine (0.018 g, 0.06 mmol) and tris(dibenzyledineacetone)dipalladium(0) (0.024 g, 0.03 mmol) was then added to the reaction mixture, which was again degassed by nitrogen for 15 min. The resulting reaction mixture was heated to 80° C. for 16 h. After the completion of the reaction (TLC monitoring), the reaction mixture was filtered through celite bed and the filtrate was concentrated to get the crude residue that was carried forward to the next step without further purification. MS: 236.10 (M+H)$^+$.

Preparation of 1-ethyl-3-(6-fluoro-5-(2-(4-methylpiperazin-1-yl)pyrimidin-5-yl)benzo[d]thiazol-2-yl)urea (III-A)

Example 57

A solution of 1-(5-bromo-6-fluoro-benzothiazol-2-yl)-3-ethyl-urea (0.13 g, 0.41 mmol), 2-(4-methylpiperazin-1-yl)-5-(4,4,5,5-tetramethyl-1,3,2-dioxaborolan-2-yl)pyrimidine II-A (0.25 g, 0.82 mmol) and K$_3$PO$_4$ (0.173 g, 0.82 mmol) in DMF-H$_2$O (5.0 mL, 4:1) was degassed by flushing with nitrogen for 15 min. Dichlorobis(triphenylphosphine)-palladium (II) (0.057 g, 0.05 mmol) was then added to the reaction mixture followed by degassing with nitrogen for another 15 min. The resulting reaction mixture was then heated to 100° C. for 2 h. After the completion of the reaction (TLC monitoring), the reaction mixture was cooled to room temperature and poured onto ice-cold water followed by extraction with EtOAc (2×50 mL). The combined organics was washed with brine, dried (Na$_2$SO$_4$), filtered and concentrated under reduced pressure. The crude was then purified over silica gel (100-200 M, 4.20% MeOH-DCM) to obtain the desired product (0.03 g, 18%). $^1$H-NMR (400 MHz, DMSO-d$_6$): δ 1.08 (t, J=7.20 Hz, 3H), 2.26 (s, 3H), 2.43 (br s, 4H), 3.20 (quintet, J=7.20 Hz, 2H), 3.80 (br s, 4H), 6.72 (br s, 1H), 7.75 (d, J=6.80 Hz, 1H), 7.91 (d, J=10.40 Hz, 1H), 8.60 (s, 2H) and 10.75 (br s, 1H). MS: 416.28 (M+H)$^+$. Qualitative HPLC Purity (Acquity BEH C-18, 100×2.1 mm, 229 nm): 96.97% (Rt=5.04 min).

Preparation of 1-ethyl-3-(6-fluoro-5-(5-methoxypyridin-3-yl)benzo[d]thiazol-2-yl)urea (III-B)

Example 58

A solution of 1-(5-bromo-6-fluoro-benzothiazol-2-yl)-3-ethyl-urea (0.10 g, 0.31 mmol), 3-methoxy-5-(4,4,5,5-tetramethyl-1,3,2-dioxaborolan-2-yl)pyridine II-B (0.148 g, 0.62 mmol) and K₃PO₄ (0.067 g, 0.31 mmol) in DMF-H₂O (2.50 mL, 2:0.5) was degassed by flushing with nitrogen for 15 min. Dichlorobis(triphenylphosphine)-palladium(II) (0.022 g, 0.03 mmol) was then added to the reaction mixture followed by degassing with nitrogen for another 15 min. The resulting reaction mixture was then heated to 100° C. for 2 h. After the completion of the reaction (TLC monitoring), the reaction mixture was cooled to room temperature and poured onto ice-cold water followed by extraction with EtOAc (2×50 mL). The combined organics was washed with brine, dried (Na₂SO₄), filtered and concentrated under reduced pressure. The crude was then purified over silica gel (60-120 M, 2.0% MeOH-DCM) to obtain the desired product (0.091 g, 84%). ¹H-NMR (400 MHz, DMSO-d₆): δ 1.09 (t, J=7.20 Hz, 3H), 3.20 (quintet, J=7.20 Hz, 2H), 3.89 (s, 3H), 6.70 (br s, 1H), 7.58 (br s, 1H), 7.81 (d, J=7.20 Hz, 1H), 7.97 (d, J=10.0 Hz, 1H), 8.33 (m, 1H), 8.38 (br s, 1H) and 10.79 (br s, 1H). MS: 347.13 (M+H)⁺. Qualitative HPLC Purity (Acquity BEH C-18, 100×2.1 mm, 244 nm): 95.04% (Rt=5.29 min).

Preparation of 1-ethyl-3-(6-fluoro-5-(5-hydroxypyridin-3-yl)benzo[d]thiazol-2-yl)urea (IV)

Example 59

A solution of 1-ethyl-3-(6-fluoro-5-(5-methoxypyridin-3-yl)benzo[d]thiazol-2-yl)urea III-B (0.025 g, 0.07 mmol) in DCM (5.0 mL) was cooled to −78° C. followed by addition of BBr₃ (0.036 g, 0.14 mmol). The resulting reaction mixture was stirred at room temperature for 1 h. After the completion of reaction (TLC monitoring), the solution was again cooled to −78° C., quenched with drop wise addition of water (5.0 mL), basified with saturated NaHCO₃ solution and extracted with EtOAc (3×25 mL). The combined organics was washed with brine, dried (Na₂SO₄), filtered and concentrated. The residue was purified over silica gel (100-200 M, 2% MeOH-DCM) to obtain the desired product (0.018 g, 75%). ¹H-NMR (400 MHz, DMSO-d₆): δ 1.09 (t, J=7.20 Hz, 3H), 3.20 (m, 2H), 6.71 (br s, 1H), 7.34 (br s, 1H), 7.73 (d, J=7.20 Hz, 1H), 7.95 (d, J=10.40 Hz, 1H), 8.16 (d, =2.40 Hz, 1H), 8.24 (s, 1H), 10.10 (br s, 1H) and 10.80 (br s, 1H). MS: 333.16 (M+H)⁺. Qualitative HPLC Purity (Acquity BEH C-18, 100×2.1 mm, 244 nm): 96.71% (Rt=4.83 min).

Scheme-29:

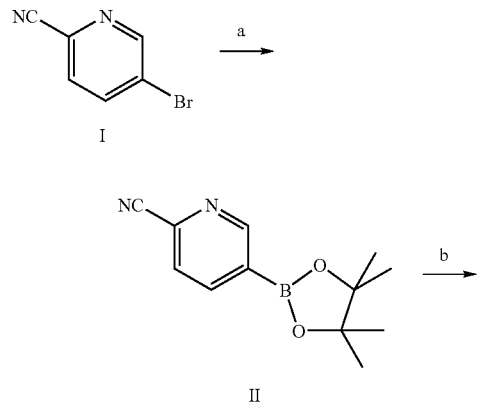

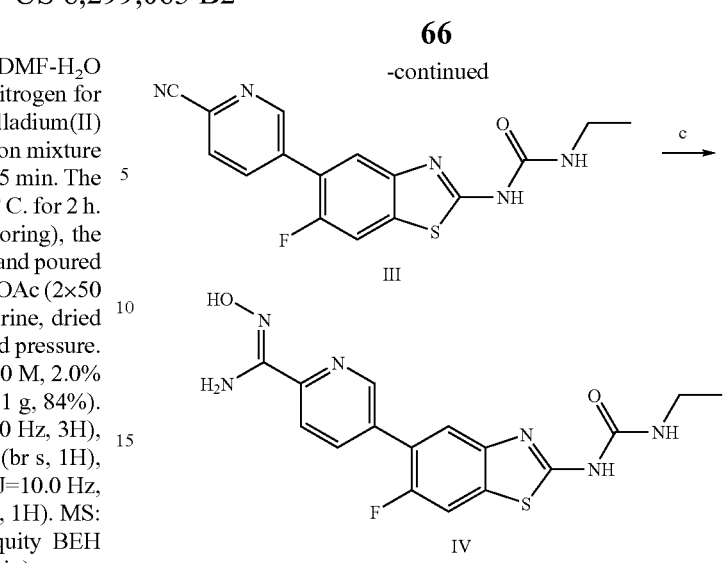

(a) Bispinacolatodiboron, KOAc, tricyclohexylphosphine, Pd₂(dba)₃, 1,4-dioxane; (b) 1-(5-bromo-6-fluoro-benzothiazol-2-yl)-3-ethyl-urea, K₃PO₄, Dichlorobis(triphenylphosphine)-palladium(II), DMF—H₂O; (c) NH₂OH•HCl, NaHCO₃, EtOH.

Preparation of 5-(4,4,5,5-tetramethyl-1,3,2-dioxaborolan-2-yl)picolinonitrile (II)

A solution of 5-bromo-2-cyanopyridine (0.50 g, 2.73 mmol), bispinacolatodiboron (0.76 g, 3.0 mmol) and KOAc (0.34 g, 4.10 mmol) in 1,4-dioxane (10.0 mL) was degassed by flushing with nitrogen for 15 min. Tricyclohexylphosphine (0.091 g, 0.33 mmol) and tris(dibenzyledineacetone)dipalladium(0) (0.14 g, 0.14 mmol) was then added to the reaction mixture, which was again degassed by nitrogen for 15 min. The resulting reaction mixture was heated to 100° C. for 2 h. After the completion of the reaction (TLC monitoring), the reaction mixture was filtered through celite bed and the filtrate was concentrated to get the crude residue that was carried forward to the next step without further purification. MS: 231.10 (M+H)⁺.

Preparation of 1-(5-(6-cyanopyridin-3-yl)-6-fluorobenzo[d]thiazol-2-yl)-3-ethylurea (III)

A solution of 1-(5-bromo-6-fluoro-benzothiazol-2-yl)-3-ethyl-urea (0.10 g, 0.31 mmol), 5-(4,4,5,5-tetramethyl-1,3,2-dioxaborolan-2-yl)picolinonitrile (0.144 g, 0.63 mmol) and K₃PO₄ (0.133 g, 0.63 mmol) in DMF-H₂O (5.0 mL, 4:1) was degassed by flushing with nitrogen for 15 min. Dichlorobis(triphenylphosphine)-palladium(II) (0.022 g, 0.03 mmol) was then added to the reaction mixture followed by degassing with nitrogen for another 15 min. The resulting reaction mixture was then heated to 100° C. for 2 h. After the completion of the reaction (TLC monitoring), the reaction mixture was cooled to room temperature and poured onto ice-cold water followed by extraction with EtOAc (2×50 mL). The combined organics was washed with brine, dried (Na₂SO₄), filtered and concentrated under reduced pressure. The crude was then purified over silica gel (100-200 M, 2.50% MeOH-DCM) to obtain the desired product (0.075 g, 71%). ¹H-NMR (400 MHz, DMSO-d₆): δ 1.09 (t, J=7.20 Hz, 3H), 3.20 (m, 2H), 6.71 (br s, 1H), 7.90 (d, J=6.80 Hz, 1H), 8.03 (d, J=10.80 Hz, 1H), 8.15 (m, 1H), 8.31 (m, 1H), 9.0 (s, 1H) and 10.90 (br s, 1H). MS: 340.06 (M−H)⁺.

Preparation of 5-(2-(3-ethylureido)-6-fluorobenzo[d]thiazol-5-yl)-N'-hydroxypicolinimidamide (IV)

Example 60

To a solution of 1-(5-(6-cyanopyridin-3-yl)-6-fluorobenzo[d]thiazol-2-yl)-3-ethylurea (0.075 g, 0.22 mmol) in EtOH (5.0 mL) was added NaHCO$_3$ (0.055, 0.66 mmol) followed by NH$_2$OH.HCl (0.045 g, 0.66 mmol). The resulting reaction mixture was heated to 78° C. for 2 h. After the completion of reaction (TLC monitoring), EtOH was evaporated, added water and extracted with EtOAc (2×25 mL). the combined organics was washed with brine, dried (Na$_2$SO$_4$), filtered and concentrated. The residue was purified over silica gel (100-200 M, 2.50% MeOH-DCM) to obtain the desired product (0.038 g, 46%). $^1$H-NMR (400 MHz, DMSO-d$_6$): δ 1.09 (t, J=7.20 Hz, 3H), 3.20 (m, 2H), 5.89 (br s, 2H), 6.76 (br s, 1H), 7.82 (d, J=6.80 Hz, 1H), 7.96 (m, 2H), 8.05 (m, 1H), 8.78 (s, 1H), 10.0 (s, 1H) and 10.82 (br s, 1H). MS: 375.15 (M+H)$^+$. Qualitative HPLC Purity (Acquity BEH C-18, 100×2.1 mm, 258 nm): 90.12% (Rt=4.97 min).

Scheme-30:

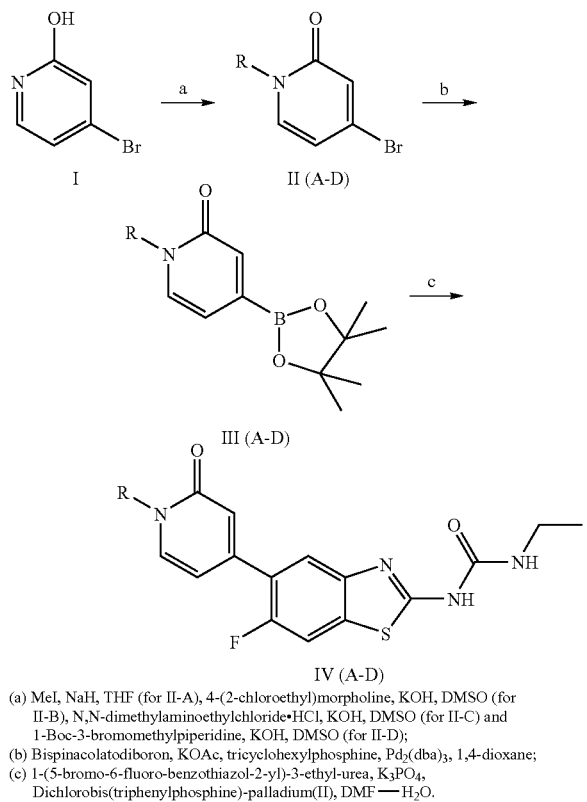

(a) MeI, NaH, THF (for II-A), 4-(2-chloroethyl)morpholine, KOH, DMSO (for II-B), N,N-dimethylaminoethylchloride•HCl, KOH, DMSO (for II-C) and 1-Boc-3-bromomethylpiperidine, KOH, DMSO (for II-D);
(b) Bispinacolatodiboron, KOAc, tricyclohexylphosphine, Pd$_2$(dba)$_3$, 1,4-dioxane;
(c) 1-(5-bromo-6-fluoro-benzothiazol-2-yl)-3-ethyl-urea, K$_3$PO$_4$, Dichlorobis(triphenylphosphine)-palladium(II), DMF—H$_2$O.

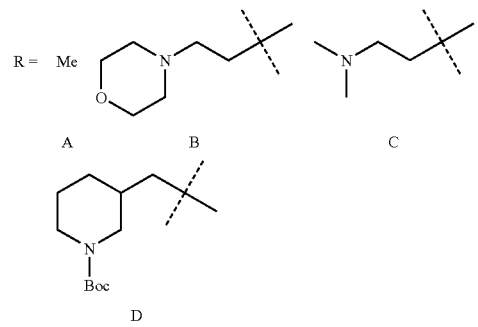

Preparation of 4-bromo-1-methylpyridin-2(1H)-one (II-A)

To an ice-cold solution of 2-hydroxy-4-bromopyridine (1.0 g, 5.75 mmol) in THF (20.0 mL) was added NaH (60% in mineral oil, 0.23 g, 5.75 mmol) portionwise. The reaction mixture was stirred at room temperature for 15 min followed by addition of methyl iodide (1.10 mL, 17.24 mmol). The resulting reaction mixture was stirred at room temperature for 16 h. After the completion of the reaction (TLC monitoring), the reaction mixture was cooled to 0° C., added water and extracted with EtOAc (3×50 mL). The combined organics was washed with brine, dried (Na$_2$SO$_4$), filtered and concentrated under reduced pressure to obtain the desired product (0.99 g, 92%). $^1$H NMR (400 MHz, DMSO-d6): δ 3.38 (s, 3H), 6.44 (dd, J=2.0 and 7.20 Hz, 1H), 6.69 (d, J=2.0 Hz, 1H) and 7.69 (d, J=7.20 Hz, 1H).

Preparation of 4-bromo-1-(2-morpholinoethyl)pyridin-2(1H)-one (II-B)

To a solution of 2-hydroxy-4-bromopyridine (0.10 g, 0.57 mmol) in DMSO (1.0 mL) was added KOH (0.13 g, 2.29 mmol) and the resulting reaction mixture was stirred for 10 min at room temperature followed by addition of 4-(2-chloroethyl)morpholine (0.13 g, 0.69 mmol). The reaction mixture was then stirred at 45° C. for 30 min. After the completion of reaction (TLC monitoring), water was added to the reaction and extracted with EtOAc (3×25 mL). The combined organics was washed with brine, dried (Na$_2$SO$_4$), filtered and concentrated. The residue was purified over silica gel (100-200 M, 5% MeOH-DCM) to obtain the desired product (0.085 g, 52%). MS: 287.10 (M+H)$^+$.

Preparation of 4-bromo-1-(2-(dimethylamino)ethyl)pyridin-2(1H)-one (II-C)

To a solution of 2-hydroxy-4-bromopyridine (0.10 g, 0.57 mmol) in DMSO (1.0 mL) was added KOH (0.13 g, 2.29 mmol) and the resulting reaction mixture was stirred for 10 min at room temperature followed by addition of N,N-dimethylaminoethylchloride.HCl (0.098 g, 0.68 mmol). The reaction mixture was then stirred at 40° C. for 1 h. After the completion of reaction (TLC monitoring), water was added to the reaction and extracted with EtOAc (3×25 mL). The combined organics was washed with brine, dried (Na$_2$SO$_4$), filtered and concentrated. The residue was triturated with ether to obtain the desired product (0.10 g, 72%). MS: 245.10 (M+H)$^+$.

Preparation of tert-butyl 3-((4-bromo-2-oxopyridin-1(2H)-yl)methyl)piperidine-1-carboxylate (II-D)

To a solution of 2-hydroxy-4-bromopyridine (0.10 g, 0.57 mmol) in DMSO (1.50 mL) was added KOH (0.095 g, 1.70 mmol) and the resulting reaction mixture was stirred for 10 min at room temperature followed by addition of 1-Boc-3-bromomethylpiperidine (0.16 g, 0.57 mmol). The reaction mixture was then stirred at 45° C. for 16 h. After the completion of reaction (TLC monitoring), water was added to the reaction and extracted with EtOAc (3×25 mL). The combined organics was washed with brine, dried (Na$_2$SO$_4$), filtered and concentrated. The residue was purified over silica gel (100-200 M, 1% MeOH-DCM) to obtain the desired product (0.15 g, 95%). MS: 371.10 (M+H)$^+$.

Preparation of 1-methyl-4-(4,4,5,5-tetramethyl-1,3,2-dioxaborolan-2-yl)pyridin-2(1H)-one (III-A)

A solution of 4-bromo-1-methylpyridin-2(1H)-one II-A (0.50 g, 2.66 mmol), bispinacolatodiboron (0.74 g, 2.93 mmol) and KOAc (0.39 g, 3.99 mmol) in 1,4-dioxane (10.0 mL) was degassed by flushing with nitrogen for 15 min. Tricyclohexylphosphine (0.090 g, 0.32 mmol) and tris(dibenzyledineacetone)dipalladium(0) (0.14 g, 0.13 mmol) was then added to the reaction mixture, which was again degassed by nitrogen for 15 min. The resulting reaction mixture was heated to 80-85° C. for 3 h. After the completion of the reaction (TLC monitoring), the reaction mixture was filtered through celite bed and the filtrate was concentrated to get the crude residue that was carried forward to the next step without further purification. MS: 236.23 (M+H)$^+$.

Preparation of 1-(2-morpholinoethyl)-4-(4,4,5,5-tetramethyl-1,3,2-dioxaborolan-2-yl)pyridin-2(1H)-one (III-B)

A solution of 4-bromo-1-(2-morpholinoethyl)pyridin-2(1H)-one II-B (0.085 g, 0.30 mmol), bispinacolatodiboron (0.089 g, 0.35 mmol) and KOAc (0.036 g, 0.44 mmol) in 1,4-dioxane (5.0 mL) was degassed by flushing with nitrogen for 15 min. Tricyclohexylphosphine (0.012 g, 0.04 mmol) and tris(dibenzyledineacetone)dipalladium(0) (0.015 g, 0.014 mmol) was then added to the reaction mixture, which was again degassed by nitrogen for 15 min. The resulting reaction mixture was heated to 80° C. for 1 h. After the completion of the reaction (TLC monitoring), the reaction mixture was filtered through celite bed and the filtrate was concentrated to get the crude residue that was carried forward to the next step without further purification. MS: 335.23 (M+H)$^+$.

Preparation of 1-(2-(dimethylamino)ethyl)-4-(4,4,5,5-tetramethyl-1,3,2-dioxaborolan-2-yl)pyridin-2(1H)-one (III-C)

A solution of 4-bromo-1-(2-(dimethylamino)ethyl)pyridin-2(1H)-one II-C (0.10 g, 0.41 mmol), bispinacolatodiboron (0.12 g, 0.49 mmol) and KOAc (0.05 g, 0.61 mmol) in 1,4-dioxane (5.0 mL) was degassed by flushing with nitrogen for 15 min. Tricyclohexylphosphine (0.017 g, 0.06 mmol) and tris(dibenzyledineacetone)dipalladium(0) (0.021 g, 0.020 mmol) was then added to the reaction mixture, which was again degassed by nitrogen for 15 min. The resulting reaction mixture was heated to 80° C. for 1 h. After the completion of the reaction (TLC monitoring), the reaction mixture was filtered through celite bed and the filtrate was concentrated to get the crude residue that was carried forward to the next step without further purification. MS: 293.20 (M+H)$^+$.

Preparation of tert-butyl 3-((2-oxo-4-(4,4,5,5-tetramethyl-1,3,2-dioxaborolan-2-yl)pyridin-1(2H)-yl)methyl)piperidine-1-carboxylate (III-D)

A solution of tert-butyl 3-((4-bromo-2-oxopyridin-1(2H)-yl)methyl)piperidine-1-carboxylate II-D (0.15 g, 0.40 mmol), bispinacolatodiboron (0.122 g, 0.48 mmol) and KOAc (0.049 g, 0.61 mmol) in 1,4-dioxane (5.0 mL) was degassed by flushing with nitrogen for 15 min. Tricyclohexylphosphine (0.017 g, 0.06 mmol) and tris(dibenzyledineacetone)dipalladium(0) (0.021 g, 0.020 mmol) was then added to the reaction mixture, which was again degassed by nitrogen for 15 min. The resulting reaction mixture was heated to 100° C. for 1 h. After the completion of the reaction (TLC monitoring), the reaction mixture was filtered through celite bed and the filtrate was concentrated to get the crude residue that was carried forward to the next step without further purification. MS: 419.20 (M+H)$^+$.

Preparation of 1-ethyl-3-(6-fluoro-5-(1-methyl-2-oxo-1,2-dihydropyridin-4-yl)benzo[d]thiazol-2-yl)urea (IV-A)

Example 61

A solution of 1-(5-bromo-6-fluoro-benzothiazol-2-yl)-3-ethyl-urea (0.20 g, 0.63 mmol), 1-methyl-4-(4,4,5,5-tetramethyl-1,3,2-dioxaborolan-2-yl) pyridin-2(1H)-one III-A (0.18 g, 0.75 mmol) and K$_3$PO$_4$ (0.20 g, 0.96 mmol) in DMF-H$_2$O (11.0 mL, 7:4) was degassed by flushing with nitrogen for 15 min. Dichlorobis(triphenylphosphine)-palladium(II) (0.044 g, 0.06 mmol) was then added to the reaction mixture followed by degassing with nitrogen for another 15 min. The resulting reaction mixture was then heated to 80° C. for 1 h. After the completion of the reaction (TLC monitoring), the reaction mixture was cooled to room temperature and poured onto ice-cold water followed by extraction with EtOAc (3×100 mL). The combined organics was washed with brine, dried (Na$_2$SO$_4$), filtered and concentrated under reduced pressure. The crude was then purified over silica gel (100-200 M, 2.50% MeOH-DCM) to obtain the desired product (0.065 g, 30%). $^1$H NMR (400 MHz, DMSO-d6): δ 1.08 (t, J=7.20 Hz, 3H), 3.20 (quintet, J=7.20 Hz, 2H), 3.44 (s, 3H), 6.44 (d, J=7.20 Hz, 1H), 6.57 (s, 1H), 6.70 (br s, 1H), 7.73 (d, J=6.40 Hz, 1H), 7.77 (d, J=6.80 Hz, 1H), 7.94 (d, J=10.40 Hz, 1H) and 10.82 (br s, 1H). MS: 345.09 (M−H)$^+$. Qualitative HPLC Purity (Acquity BEH C-18, 100×2.1 mm, 238 nm): 92.19% (Rt=4.64 min).

Preparation of 1-ethyl-3-(6-fluoro-5-(1-(2-morpholinoethyl)-2-oxo-1,2-dihydropyridin-4-yl)benzo[d]thiazol-2-yl)urea (IV-B)

Example 62

A solution of 1-(5-bromo-6-fluoro-benzothiazol-2-yl)-3-ethyl-urea (0.05 g, 0.16 mmol), 1-(2-morpholinoethyl)-4-(4,4,5,5-tetramethyl-1,3,2-dioxaborolan-2-yl)pyridin-2(1H-one III-B (0.08 g, 0.22 mmol) and K$_3$PO$_4$ (0.05 g, 0.24 mmol) in DMF-H$_2$O (7.0 mL, 5:2) was degassed by flushing with nitrogen for 15 min. Dichlorobis(triphenylphosphine)-palladium(II) (0.012 g, 0.017 mmol) was then added to the reaction mixture followed by degassing with nitrogen for another 15 min. The resulting reaction mixture was then heated to 95° C. for 3 h. After the completion of the reaction (TLC monitoring), the reaction mixture was cooled to room temperature and poured onto ice-cold water followed by extraction with EtOAc (3×50 mL). The combined organics was washed with brine, dried (Na$_2$SO$_4$), filtered and concentrated under reduced pressure. The crude was then purified over silica gel (100-200 M, 5.0% MeOH-DCM) to obtain the desired product (0.020 g, 28%). $^1$H NMR (400 MHz, DMSO-d6): δ 1.09 (t, J=7.20 Hz, 3H), 2.50 (m, 4H), 2.58 (t, J=6.0 Hz, 2H), 3.20 (m, 2H), 3.55 (t, J=4.40 Hz, 4H), 4.03 (t, J=6.40 Hz, 2H), 6.47 (d, J=6.80 Hz, 1H), 6.59 (s, 1H), 6.70 (br s, 1H), 7.73 (m, 2H), 7.94 (d, J=10.40 Hz, 1H) and 10.83 (br s, 1H). MS: 446.15

(M+H)⁺. Qualitative HPLC Purity (Acquity BEH C-18, 2.1× 100 mm, 238 nm): 95.30% (Rt=4.81 min).

Preparation of 1-(5-(1-(2-(dimethylamino)ethyl)-2-oxo-1,2-dihydropyridin-4-yl)-6-fluorobenzo[d]thiazol-2-yl)-3-ethylurea (IV-C)

Example 63

A solution of 1-(5-bromo-6-fluoro-benzothiazol-2-yl)-3-ethyl-urea (0.12 g, 0.41 mmol), 1-(2-(dimethylamino)ethyl)-4-(4,4,5,5-tetramethyl-1,3,2-dioxaborolan-2-yl)pyridin-2(1H)-one III-C (0.065 g, 0.21 mmol) and $K_3PO_4$ (0.13 g, 0.62 mmol) in DMF-$H_2O$ (5.0 mL, 3:2) was degassed by flushing with nitrogen for 15 min. Dichlorobis(triphenylphosphine)-palladium(II) (0.028 g, 0.041 mmol) was then added to the reaction mixture followed by degassing with nitrogen for another 15 min. The resulting reaction mixture was then heated to 100° C. for 2 h. After the completion of the reaction (TLC monitoring), the reaction mixture was cooled to room temperature and poured onto ice-cold water followed by extraction with EtOAc (3×50 mL). The combined organics was washed with brine, dried ($Na_2SO_4$), filtered and concentrated under reduced pressure. The crude was then purified over silica gel (100-200 M, 9.0% MeOH-DCM) to obtain the desired product (0.037 g, 41%). ¹H NMR (400 MHz, DMSO-d6): δ 1.08 (t, J=7.20 Hz, 3H), 2.21 (s, 6H), 2.55 (m, 2H), 3.20 (m, 2H), 4.01 (t, J=6.0 Hz, 2H), 6.46 (d, J=6.80 Hz, 1H), 6.56 (s, 1H), 6.73 (br s, 1H), 7.72 (m, 2H), 7.95 (d, J=10.40 Hz, 1H) and 10.86 (br s, 1H). MS: 404.23 (M+H)⁺. Qualitative HPLC Purity (Acquity BEH C-18, 2.1×100 mm, 238 nm): 96.07% (Rt=4.42 min).

Preparation of tert-butyl 3-((4-(2-(3-ethylureido)-6-fluorobenzo[d]thiazol-5-yl)-5-yl)-2,2'-dioxo-2H-1,4'-bipyridin-1'(2'H)-yl)methyl)piperidine-1-carboxylate (IV-D)

Example 64

A solution of 1-(5-bromo-6-fluoro-benzothiazol-2-yl)-3-ethyl-urea (0.15 g, 0.47 mmol), tert-butyl 3-((2-oxo-4-(4,4,5,5-tetramethyl-1,3,2-dioxaborolan-2-yl)pyridin-1(2H)-yl)methyl)piperidine-1-carboxylate III-D (0.39 g, 0.94 mmol) and $K_3PO_4$ (0.15 g, 0.26 mmol) in DMF-$H_2O$ (5.0 mL, 3:2) was degassed by flushing with nitrogen for 15 min. Dichlorobis(triphenylphosphine)-palladium(II) (0.033 g, 0.047 mmol) was then added to the reaction mixture followed by degassing with nitrogen for another 15 min. The resulting reaction mixture was then heated to 100° C. for 2 h. After the completion of the reaction (TLC monitoring), the reaction mixture was cooled to room temperature and poured onto ice-cold water followed by extraction with EtOAc (3×50 mL). The combined organics was washed with brine, dried ($Na_2SO_4$), filtered and concentrated under reduced pressure. The crude was then purified over silica gel (100-200 M, 2.50% MeOH-DCM) to obtain the desired product (0.032 g, 11%). ¹H NMR (400 MHz, DMSO-d6): δ 1.08 (t, J=7.20 Hz, 3H), 1.19 (m, 1H), 1.33 (s, 9H), 1.67 (m, 2H), 1.88 (m, 2H), 2.30 (m, 1H), 2.79 (m, 1H), 3.20 (m, 2H), 3.73-3.82 (m, 4H), 6.49 (d, J=6.80 Hz, 1H), 6.60 (s, 1H), 6.70 (br s, 1H), 7.74 (m, 2H), 7.95 (d, J=10.80 Hz, 1H) and 10.85 (br s, 1H). LCMS: 84.22% (Rt=3.34 min).

Scheme-31:

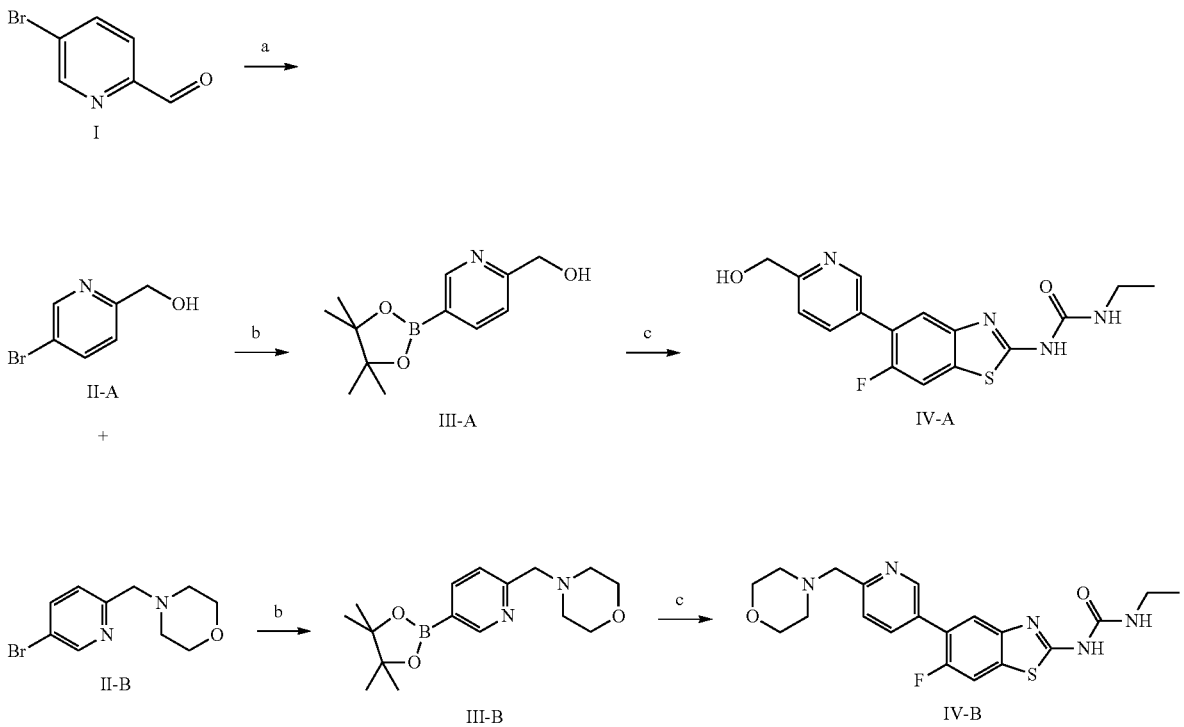

(a) Na(OAc)₃BH, glacial acetic acid, morpholine, DCM, room temperature, 4 h; (b) Bispinacolatodiboron, KOAc, tricyclohexylphosphine, Pd₂(dba)₃ 1,4-dioxane;
(c) 1-(5-bromo-6-fluoro-benzothiazol-2-yl)-3-ethyl-urea, K₃PO₄, Dichlorobis(triphenylphosphine)-palladium(II), DMF—H₂O.

Preparation of (5-bromopyridin-2-yl)methanol (II-A) and 4-((5-bromopyridin-2-yl)methyl)morpholine (II-B)

To a solution of 5-bromo-pyridine-2-carbaldehyde (0.30 g, 1.62 mmol) in DCM (15 mL) was added morpholine (0.10 g, 1.13 mmol) and glacial acetic acid (2 mL) and stirred the resulting reaction mixture for 30 min. followed by addition of sodium triacetoxyborohydride (0.86 g, 4.05 mmol). The resulting reaction mixture was stirred for 4 h at room temperature. After completion of reaction (TLC monitoring), the reaction mixture was diluted with DCM, added water and extracted the organic layer. The organic layer was dried over $Na_2SO_4$ and concentrated. The crude residue was purified over silica-gel [100-200 M, compound II-A (0.21 g, 69%) eluted in 1.50% EtOAc-hexane and compound II-B (0.12 g, 28%) eluted in 5% EtOAc-hexane.

Preparation of (5-(4,4,5,5-tetramethyl-1,3,2-dioxaborolan-2-yl)pyridin-2-yl)methanol (III-A)

A solution of (5-bromopyridin-2-yl)methanol II-A (0.20 g, 1.06 mmol), bispinacolatodiboron (0.32 g, 1.27 mmol) and KOAc (0.13 g, 1.59 mmol) in 1,4-dioxane (5.0 mL) was degassed by flushing with nitrogen for 15 min. Tricyclohexylphosphine (0.045 g, 0.16 mmol) and tris(dibenzyledineacetone)dipalladium(0) (0.055 g, 0.053 mmol) was then added to the reaction mixture, which was again degassed by nitrogen for 15 min. The resulting reaction mixture was heated to 80° C. for 16 h. After the completion of the reaction (TLC monitoring), the reaction mixture was filtered through celite bed and the filtrate was concentrated to get the crude residue that was carried forward to the next step without further purification. MS: 236.20 (M+H)$^+$.

Preparation of 4-((5-(4,4,5,5-tetramethyl-1,3,2-dioxaborolan-2-yl)pyridin-2-yl)methyl)morpholine (III-B)

A solution of 4-((5-bromopyridin-2-yl)methyl)morpholine II-B (0.10 g, 0.39 mmol), bispinacolatodiboron (0.12 g, 0.47 mmol) and KOAc (0.048 g, 0.59 mmol) in 1,4-dioxane (5.0 mL) was degassed by flushing with nitrogen for 15 min. Tricyclohexylphosphine (0.017 g, 0.05 mmol) and tris(dibenzyledineacetone)dipalladium(0) (0.02 g, 0.02 mmol) was then added to the reaction mixture, which was again degassed by nitrogen for 15 min. The resulting reaction mixture was heated to 80° C. for 8 h. After the completion of the reaction (TLC monitoring), the reaction mixture was filtered through celite bed and the filtrate was concentrated to get the crude residue that was carried forward to the next step without further purification. MS: 305.20 (M+H)$^+$.

Preparation of 1-ethyl-3-(6-fluoro-5-(6-(hydroxymethyl)pyridin-3-yl)benzo[d]thiazol-2-yl)urea (IV-A)

Example 65

A solution of 1-(5-bromo-6-fluoro-benzothiazol-2-yl)-3-ethyl-urea (0.10 g, 0.31 mmol), (5-(4,4,5,5-tetramethyl-1,3,2-dioxaborolan-2-yl)pyridin-2-yl)methanol III-A (0.15 g, 0.63 mmol) and $K_3PO_4$ (0.13 g, 0.62 mmol) in DMF-$H_2O$ (6.0 mL, 4:2) was degassed by flushing with nitrogen for 15 min. Dichlorobis(triphenylphosphine)-palladium(II) (0.022 g, 0.03 mmol) was then added to the reaction mixture followed by degassing with nitrogen for another 15 min. The resulting reaction mixture was then heated to 80° C. for 2 h. After the completion of the reaction (TLC monitoring), the reaction mixture was cooled to room temperature and poured onto ice-cold water followed by extraction with EtOAc (3×50 mL). The combined organics was washed with brine, dried ($Na_2SO_4$), filtered and concentrated under reduced pressure. The crude was then purified over silica gel (100-200 M, 2.80% MeOH-DCM) to obtain the desired product (0.050 g, 46%). $^1$H NMR (400 MHz, DMSO-d6): δ 1.09 (t, J=7.20 Hz, 3H), 3.20 (m, 2H), 4.63 (d, J=6.0 Hz, 2H), 5.49 (t, J=5.60 Hz, 1H), 6.71 (br s, 1H), 7.56 (d, J=8.0 Hz, 1H), 7.77 (d, J=6.80 Hz, 1H), 7.96 (d, J=10.40 Hz, 1H), 8.0 (m, 1H), 8.68 (s, 1H) and 10.79 (br s, 1H). MS: 347.17 (M+H)$^+$. Qualitative HPLC Purity (Acquity BEH C-18, 2.1×100 mm, 248 nm): 96.75% (Rt=4.75 min).

Preparation of 1-ethyl-3-(6-fluoro-5-(6-(morpholinomethyl)pyridin-3-yl)benzo[d]thiazol-2-yl)urea (IV-B)

Example 66

A solution of 1-(5-bromo-6-fluoro-benzothiazol-2-yl)-3-ethyl-urea (0.07 g, 0.22 mmol), 4-((5-(4,4,5,5-tetramethyl-1,3,2-dioxaborolan-2-yl)pyridin-2-yl)methyl)morpholine III-A (0.134 g, 0.44 mmol) and $K_3PO_4$ (0.094 g, 0.44 mmol) in DMF-$H_2O$ (5.0 mL, 3:2) was degassed by flushing with nitrogen for 15 min. Dichlorobis(triphenylphosphine)-palladium(II) (0.014 g, 0.02 mmol) was then added to the reaction mixture followed by degassing with nitrogen for another 15 min. The resulting reaction mixture was then heated to 80° C. for 2 h. After the completion of the reaction (TLC monitoring), the reaction mixture was cooled to room temperature and poured onto ice-cold water followed by extraction with EtOAc (3×50 mL). The combined organics was washed with brine, dried ($Na_2SO_4$), filtered and concentrated under reduced pressure. The crude was then purified over silica gel (100-200 M, 5.0% MeOH-DCM) to obtain the desired product (0.007 g, 8%). $^1$H NMR (400 MHz, DMSO-d6): δ 1.09 (t, J=7.20 Hz, 3H), 2.45 (m, 4H), 3.20 (m, 2H), 3.61 (m, 4H), 3.64 (s, 2H), 6.71 (br s, 1H), 7.57 (d, J=8.0 Hz, 1H), 7.77 (d, J=6.80 Hz, 1H), 7.93-8.0 (m, 2H), 8.70 (s, 1H) and 10.80 (br s, 1H). MS: 416.24 (M+H)$^+$. Qualitative HPLC Purity (Acquity BEH C-18, 2.1×100 mm, 249 nm): 92.05% (Rt=5.35 min).

Scheme-32:

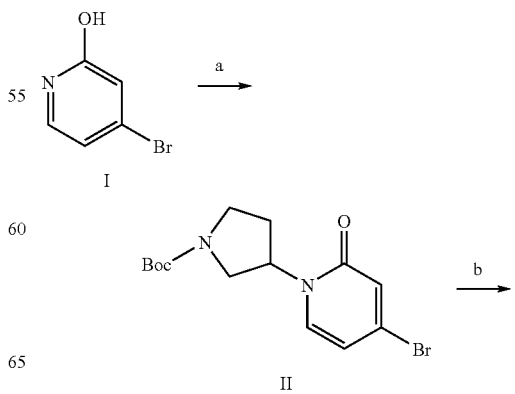

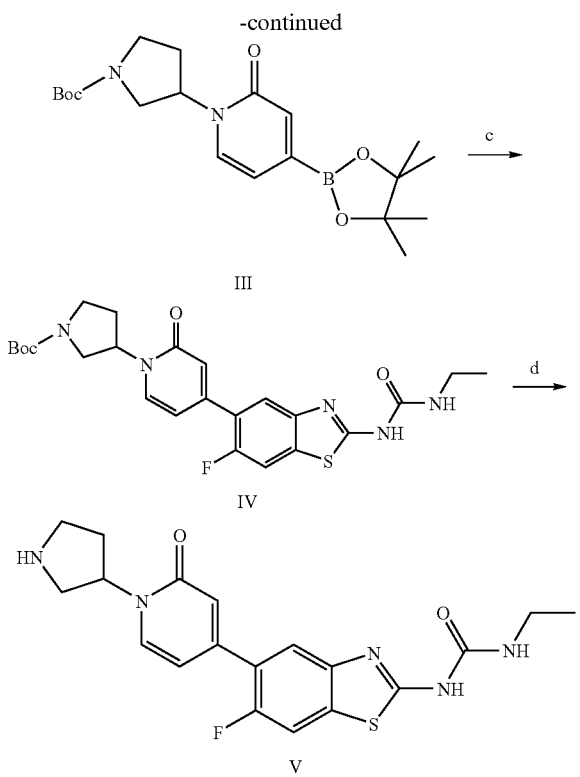

(a) 1-Boc-3-hydroxypyrrolidine, Triphenylphosphine, DIAD, THF; (b) Bispinacolatodiboron, KOAc, tricyclohexylphosphine, Pd$_2$(dba)$_3$, 1,4-dioxane; (c) 1-(5-bromo-6-fluoro-benzothiazol-2-yl)-3-ethyl-urea, K$_3$PO$_4$, Dichlorobis(triphenylphosphine)-palladium(II), DMF—H$_2$O; (d) HCl-1,4-dioxane.

Preparation of tert-butyl 3-(4-bromo-2-oxopyridin-1 (2H)-yl)pyrrolidine-1-carboxylate (II)

To an ice cold solution of triphenylphosphine (0.17 g, 0.63 mmol) in THF (10.0 mL) was added DIAD (0.12 mL, 0.63 mmol) and the resulting solution was stirred at the same temperature for 15 min. after which a yellow precipitate was formed. 1-Boc-3-hydroxypyrrolidine (0.10 g, 0.53 mmol) was then added to the reaction mixture and allowed to stir for 20 min followed by addition of 4-bromo-2-hydroxypyridine (0.093 g, 0.53 mmol). The resulting reaction mixture was stirred for 16 h at room temperature. After completion of reaction (TLC monitoring), the reaction mixture was diluted with water and extracted with EtOAc (3×50 ml). The combined organics was dried (Na$_2$SO$_4$), filtered and concentrated. The residue was purified over silica gel (100-200 M, 0.5% MeOH-DCM) to obtain the desired product (0.20 g, quantitative yield). MS: 343.10 (M+H)$^+$.

Preparation of tert-butyl 3-(2-oxo-4-(4,4,5,5-tetramethyl-1,3,2-dioxaborolan-2-yl)pyridin-1(2H)-yl)pyrrolidine-1-carboxylate (III)

A solution of tert-butyl 3-(4-bromo-2-oxopyridin-1(2H)-yl)pyrrolidine-1-carboxylate (0.20 g, 0.58 mmol), bispinacolatodiboron (0.29 g, 1.16 mmol) and KOAc (0.17 g, 1.74 mmol) in 1,4-dioxane (7.0 mL) was degassed by flushing with nitrogen for 15 min. Tricyclohexylphosphine (0.025 g, 0.87 mmol) and tris(dibenzyledineacetone)dipalladium(0) (0.053 g, 0.058 mmol) was then added to the reaction mixture, which was again degassed by nitrogen for 15 min. The resulting reaction mixture was heated to 80° C. for 2 h. After the completion of the reaction (TLC monitoring), the reaction mixture was filtered through celite bed and the filtrate was concentrated to get the crude residue that was carried forward to the next step without further purification. MS: 391.20 (M+H)$^+$.

Preparation of tert-butyl 3-(4-(2-(3-ethylureido)-6-fluorobenzo[d]thiazol-5-yl)-2-oxopyridin-1(2H)-yl) pyrrolidine-1-carboxylate (IV)

A solution of 1-(5-bromo-6-fluoro-benzothiazol-2-yl)-3-ethyl-urea (0.07 g, 0.31 mmol), tert-butyl 3-(2-oxo-4-(4,4,5,5-tetramethyl-1,3,2-dioxaborolan-2-yl)pyridin-1(2H)-yl) pyrrolidine-1-carboxylate (0.24 g, 0.62 mmol) and K$_3$PO$_4$ (0.13 g, 0.62 mmol) in DMF-H$_2$O (5.0 mL, 3:2) was degassed by flushing with nitrogen for 15 min. Dichlorobis(triphenylphosphine)-palladium(II) (0.022 g, 0.03 mmol) was then added to the reaction mixture followed by degassing with nitrogen for another 15 min. The resulting reaction mixture was then heated to 80° C. for 2 h. After the completion of the reaction (TLC monitoring), the reaction mixture was cooled to room temperature and poured onto ice-cold water followed by extraction with EtOAc (3×50 mL). The combined organics was washed with brine, dried (Na$_2$SO$_4$), filtered and concentrated under reduced pressure. The crude was then purified over silica gel (100-200 M, 1.50% MeOH-DCM) to obtain the desired product (0.056 g, 36%). MS: 502.20 (M+H)$^+$.

Preparation of 1-ethyl-3-(6-fluoro-5-(2-oxo-1-(pyrrolidin-3-yl)-1,2-dihydropyridin-4-yl)benzo[d]thiazol-2-yl)urea (V)

Example 67

A solution of tert-butyl 3-(4-(2-(3-ethylureido)-6-fluorobenzo[d]thiazol-5-yl)-2-oxopyridin-1(2H)-yl)pyrrolidine-1-carboxylate (0.055 g, 0.11 mmol) in HCl-1,4-dioxane (3.0 mL) was stirred for 30 min at room temperature. After the completion of reaction (TLC monitoring), the solvent was evaporated and the residue was triturated with ether to obtain the desired product (0.01 g, 45%). $^1$H NMR (400 MHz, DMSO-d6): δ 1.10 (t, J=7.20 Hz, 3H), 1.30 (m, 1H), 1.81 (m, 1H), 2.27 (m, 1H), 3.15 (m, 2H), 3.20 (m, 2H), 3.40 (m, 1H), 5.63 (m, 1H), 6.85 (br s, 1H), 7.01 (s, 1H), 7.29 (m, 1H), 7.79 (d, J=6.80 Hz, 1H), 7.98 (d, J=10.80 Hz, 1H), 8.28 (d, J=5.20 Hz, 1H), 9.13 (br s, 1H) and 10.90 (br s, 1H). LCMS: 402.09 (86.80%).

Scheme-33:

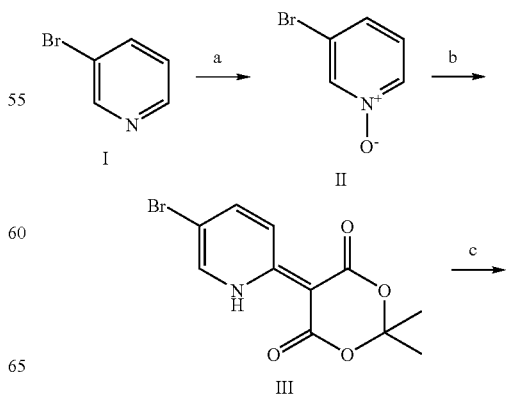

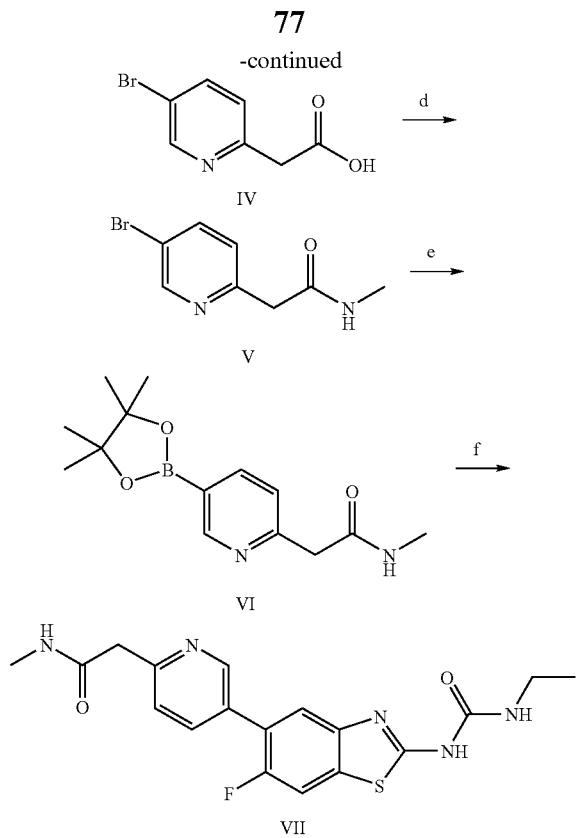

(a) m-CPBA, DCM; (b) Meldrum's acid, acetic anhydride; (c) Conc. HCl 80° C.; (d) Methylamine, HOBt, EDCI•HCl; (e) Pd$_2$(dba)$_3$, tricyclohexylphosphine, KOAc, 1,4-1,4-dioxane, 80° C., 8-10 h; (f) 1-(5-bromo-6-fluoro-benzothiazol-2-yl)-3-ethyl-urea, K$_3$PO$_4$, PdCl$_2$(PPh$_3$)$_2$, DMF—H$_2$O.

Synthesis up to intermediate IV:
[(5-Bromo-pyridin-2-yl)-acetic acid]

As per ref: *Tetrahedron*, 53, 24, 1997, 8257-8268.

Preparation of [2-(5-bromo-pyridin-2-yl)-N-methyl-acetamide] (V)

To a suspension of 5-bromo-pyridin-2-yl-acetic acid (0.87 g, 4.0 mmol) in THF (12 mL) was added HOBt (0.74 g, 4.8 mmol) and EDCI.HCl (0.85 g, 4.4 mmol). The resulting reaction mixture was stirred for 15-20 min at room temperature followed by drop-wise addition of methylamine (2.0 M in THF, 4.05 mL, 8.0 mmol). The resulting mixture was then continued to stir for 6-7 h at room temperature. After completion of reaction, water was added and extracted with EtOAc. The crude residue was purified over silica (60-120 M, 2.50% MeOH-DCM) to obtain the pale-yellow solid compound (0.25 g, 27%). $^1$H NMR (400 MHz, DMSO-d6): δ 2.58 (d, J=4.80 Hz, 3H), 3.57 (s, 2H), 7.33 (m, 1H), 7.96 (d, J=2.40 Hz and 8.40 Hz, 1H), 8.00 (br s, 1H) and 8.58 (d, J=2.40 Hz, 1H). MS: 229.11 (M+H$^+$).

Preparation of N-methyl-2-[5-(4,4,5,5-tetramethyl-[1,3,2]dioxaborolan-2-yl)-pyridin-2-yl]-acetamide (VI)

A solution of 2-(5-bromo-pyridin-2-yl)-N-methyl-acetamide] (0.5 g, 0.22 mmol) in 1,4-1,4-dioxane was degassed by bubbling nitrogen for 15-20 min followed by sequential addition of Pd$_2$(dba)$_3$ (0.01 g, 0.01 mmol), bispinacolatodiboron (0.06 g, 0.24 mmol), tricyclohexyl phosphine (0.007 g 0.03 mmol) and potassium acetate (0.03 g, 0.033 mmol). The reaction mixture was again degassed for 15-20 min and then heated up to 80° C. for 16 h. After completion of reaction (TLC monitoring), the reaction mixture was cooled, diluted with ethyl acetate and filtered through celite bed. The filtrate was dried over Na$_2$SO$_4$, filtered, concentrated and washed with hexane. The crude oily compound (60 mg) was used further without purification. MS: 277.26 (M+H$^+$).

Preparation of 2-{5-[2-(3-ethyl-ureido)-6-fluoro-benzothiazol-5-yl]-pyridin-2-yl}-N-methyl-acetamide (VII)

Example 68

A solution of 1-(5-bromo-6-fluoro-benzothiazol-2-yl)-3-ethyl-urea (0.07 g, 0.22 mmol), N-methyl-2-[5-(4,4,5,5-tetramethyl-[1,3,2]dioxaborolan-2-yl)-pyridin-2-yl]-acetamide VI (0.122 g, 0.44 mmol) and K$_3$PO$_4$ (0.094 g, 0.44 mmol) in DMF-H$_2$O (8.0 mL, 5:3) was degassed by flushing with nitrogen for 15 min. Dichlorobis(triphenylphosphine)-palladium (II) (0.016 g, 0.022 mmol) was then added to the reaction mixture followed by degassing with nitrogen for another 15 min. The resulting reaction mixture was then heated to 100° C. for 6 h. After the completion of the reaction (TLC monitoring), the reaction mixture was cooled to room temperature and poured onto ice-cold water followed by extraction with EtOAc (3×50 mL). The combined organics was washed with brine, dried (Na$_2$SO$_4$), filtered and concentrated under reduced pressure. The crude was then purified over silica gel (230-400 M, 4% MeOH-DCM) to obtain the desired product (0.006 g, 7%). $^1$H NMR (DMSO-d6, 400 MHz): δ 1.09 (t, J=6.80 Hz, 3H), 2.60 (d, J=3.60 Hz, 3H), 3.18 (m, 2H), 3.65 (s, 2H), 6.73 (br s, 1H), 7.45 (d, J=8.00 Hz, 1H), 7.77 (d, J=6.40 Hz, 1H), 7.96 (d, J=9.20 Hz, 2H), 8.08 (br s, 1H), 8.68 (s, 1H) and 10.81 (br s, 1H). MS: 388.21 (M+H$^+$). Qualitative HPLC Purity (Acquity BEH C-18, 2.1×100 mm, 249 nm): 97.02% (Rt=4.69 min).

Scheme-34:

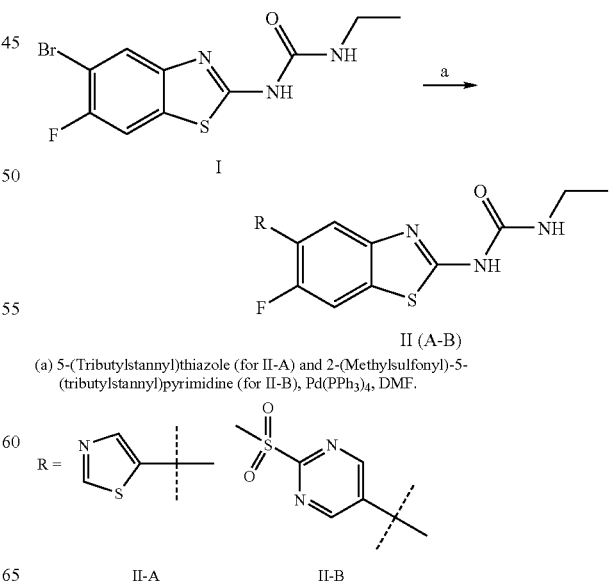

(a) 5-(Tributylstannyl)thiazole (for II-A) and 2-(Methylsulfonyl)-5-(tributylstannyl)pyrimidine (for II-B), Pd(PPh$_3$)$_4$, DMF.

Preparation of 1-ethyl-3-(6-fluoro-5-(thiazol-5-yl)benzo[d]thiazol-2-yl)urea (II-A)

Example 69

To a solution of 1-(5-bromo-6-fluoro-benzothiazol-2-yl)-3-ethyl-urea (0.10 g, 0.31 mmol) in DMF (4.0 mL) was added 5-(tributylstannyl)thiazole (0.18 g, 0.47 mmol) and the resulting solution was degassed by flushing with nitrogen for 15 min. followed by addition of Pd(PPh$_3$)$_4$ (0.036 g, 0.03 mmol). The resulting reaction mixture was again degassed with nitrogen for 15 min. and then heated to 100° C. for 1 h. After the completion of the reaction (TLC monitoring), the reaction mixture was cooled to room temperature and poured onto ice-cold water followed by extraction with EtOAc (3×50 mL). The combined organics was washed with brine, dried (Na$_2$SO$_4$), filtered and concentrated under reduced pressure. The crude was then purified over silica gel (100-200 M, 2.0% MeOH-DCM) to obtain the desired product (0.033 g, 33%). $^1$H NMR (DMSO-d6, 400 MHz): δ 1.09 (t, J=7.20 Hz, 3H), 3.20 (m, 2H), 6.72 (br s, 1H), 7.97-8.04 (m, 2H), 8.43 (s, 1H), 9.19 (s, 1H) and 10.82 (br s, 1H). MS: 323.13 (M+H)$^+$. Qualitative HPLC Purity (Acquity BEH C-18, 2.1×100 mm, 262 nm): 88.55% (Rt=5.18 min).

Preparation of 1-ethyl-3-(6-fluoro-5-(2-(methylsulfonyl)pyrimidin-5-yl)benzo[d]thiazol-2-yl)urea (II-B)

Example 70

To a solution of 1-(5-bromo-6-fluoro-benzothiazol-2-yl)-3-ethyl-urea (0.06 g, 0.19 mmol) in DMF (4.0 mL) was added 2-(methylsulfonyl)-5-(tributylstannyl)pyrimidine (0.13 g, 0.28 mmol) and the resulting solution was degassed by flushing with nitrogen for 15 min. followed by addition of Pd(PPh$_3$)$_4$ (0.022 g, 0.019 mmol). The resulting reaction mixture was again degassed with nitrogen for 15 min. and then heated to 100° C. for 3 h. After the completion of the reaction (TLC monitoring), the reaction mixture was cooled to room temperature and poured onto ice-cold water followed by extraction with EtOAc (3×50 mL). The combined organics was washed with brine, dried (Na$_2$SO$_4$), filtered and concentrated under reduced pressure. The crude was then purified over silica gel (230-400 M, 1.60% MeOH-DCM) to obtain the desired product (0.007 g, 10%). $^1$H NMR (DMSO-d6, 400 MHz): δ 1.09 (t, J=7.20 Hz, 3H), 3.19 (m, 2H), 3.47 (s, 3H), 6.72 (br s, 1H), 8.03 (d, J=6.80 Hz, 1H), 8.08 (d, J=10.40 Hz, 1H), 9.34 (s, 2H) and 10.86 (br s, 1H). MS: 393.95 (M−H)$^+$. LCMS: 395.99 (M+H)$^+$, 90.39%.

Scheme-35:

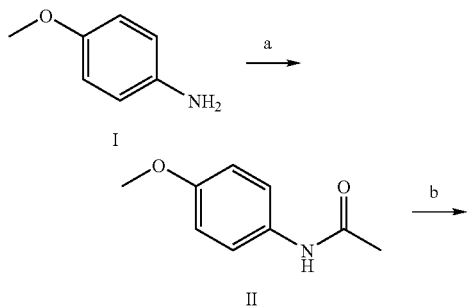

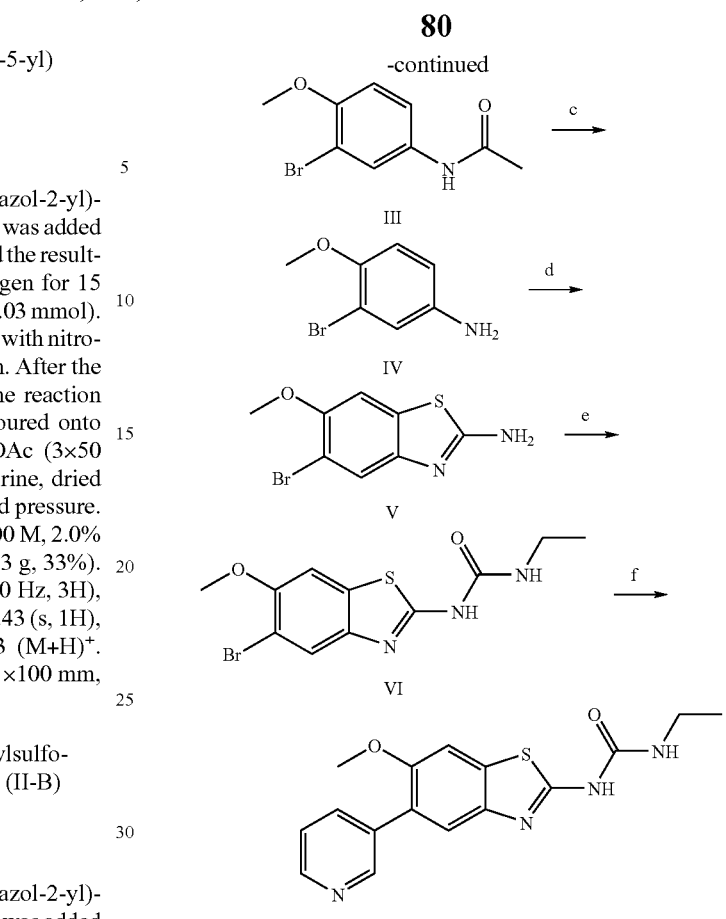

(a) Et$_3$N, Acetyl chloride, DCM; (b) Br$_2$, AcOH, 65° C.; (c) EtOH, HCl, 80° C.; (d) (i) Ammonium thiocyanate, (ii) Br$_2$, AcOH; (e) Ethylisocyante, 1,4-dioxane, 80° C.; (f) Pyridine-3-boronic acid, PdCl$_2$(dppf), K$_3$PO$_4$, 1,4-dioxane, MeOH.

Preparation of N-(4-methoxyphenyl)acetamide (II)

To an ice-cold solution of p-anisidine (25 g, 203.0 mmol) in DCM (300.0 mL) was added triethyl amine (90.0 mL, 609.0 mmol) dropwise and the reaction mixture was stirred at the same temperature for 15 min. Acetyl chloride (23.0 mL, 304.50 mmol) was then added and the reaction mixture was continued to stir at room temperature for 1 h. After the completion of the reaction (TLC monitoring), water (500 mL) was added and extracted with DCM (2×300 mL). The combined organics was washed with brine, dried (Na$_2$SO$_4$), filtered and concentrated under reduced pressure to obtain the desired product (30.0 g, 90%). $^1$H NMR (400 MHz, DMSO-d6): δ 1.99 (s, 3H), 3.70 (s, 3H), 6.86 (d, J=8.80 Hz, 2H), 7.48 (d, J=8.80 Hz, 2H) and 9.77 (br s, 1H).

Preparation of N-(3-bromo-4-methoxyphenyl)acetamide (III)

To a solution of N-(4-methoxyphenyl)acetamide II (7.50 g, 45.40 mmol) in acetic acid (50 mL) was added a solution of Br$_2$ (4.70 mL, 90.80 mmol) in acetic acid (10.0 mL). The resulting reaction mixture was then heated to 65° C. for 4 h. After the completion of the reaction (TLC monitoring), acetic acid was distilled off, cooled the residue to 0° C. and then basified with aqueous NH$_3$ till pH 12 followed by extraction with EtOAc (2×500.0 mL). The combined organics was washed with brine, dried (Na$_2$SO$_4$), filtered and concentrated under reduced pressure. The crude residue was purified over silica gel (60-120 M, 25-30% EtOAc-Hexane) to obtain the desired product (5.0 g, 45%). $^1$H NMR (400 MHz, DMSO-d6): δ 2.0 (s, 3H), 3.79 (s, 3H), 7.06 (d, J=8.80 Hz, 1H), 7.44 (dd, J=2.40 and 8.80 Hz, 1H), 7.91 (d, J=2.40 Hz, 1H) and 9.92 (br s, 1H). MS: 244.15 (M+H)$^+$.

Preparation of 3-bromo-4-methoxyaniline (IV)

To a solution of N-(3-bromo-4-methoxyphenyl)acetamide III (5.0 g, 20.50 mmol) in EtOH (40.0 mL) was added concentrated HCl (20.0 mL) and heated the reaction mixture to 80° C. for 4-5 h. After the completion of the reaction (TLC monitoring), EtOH was distilled off and the residue was cooled to 0° C. followed by basification with aqueous NH$_3$ till pH 12 and extraction with EtOAc (2×250 mL). The combined organics was washed with brine, dried (Na$_2$SO$_4$), filtered and concentrated under reduced pressure to obtain the desired product (3.56 g, 87%). $^1$H NMR (400 MHz, DMSO-d6): δ 3.67 (s, 3H), 4.88 (br s, 2H), 6.54 (dd, J=2.40 and 8.40 Hz, 1H) and 6.80 (m, 2H). MS: 202.17 (M+H)$^+$.

Preparation of 5-bromo-6-methoxybenzo[d]thiazol-2-amine (V)

To a solution of 3-bromo-4-methoxyaniline IV (2.0 g, 9.90 mmol) in AcOH (25.0 mL) was added ammonium thiocyanate (3.80 g, 49.50 mmol) and the reaction mixture was stirred at room temperature for 1 h. The reaction mixture was then cooled to 0° C. followed by addition of a solution of Br$_2$ (0.60 mL, 11.0 mmol) in AcOH (10.0 mL). The reaction mixture was then allowed to stir at room temperature for 2 h. After the completion of the reaction (TLC monitoring), AcOH was distilled off, and the residue was cooled to 0° C. followed by basification with aqueous NH$_3$ till pH 12 and extraction with EtOAc (2×250 mL). The combined organics was washed with brine, dried (Na$_2$SO$_4$), filtered and concentrated under reduced pressure to obtain the desired product (2.0 g, 78%). $^1$H NMR (400 MHz, DMSO-d6): δ 3.80 (s, 3H), 7.41 (br s, 2H), 7.49 (s, 1H) and 7.50 (s, 1H).

Preparation of 1-(5-bromo-6-methoxybenzo[d]thiazol-2-yl)-3-ethylurea (VI)

To a solution of 5-bromo-6-methoxybenzo[d]thiazol-2-amine V (2.0 g, 7.72 mmol) in 1,4-dioxane (20.0 mL) was added ethylisocyanate (3.0 mL, 38.60 mmol) and heated the resulting reaction mixture to 80° C. for 16 h. After the completion of the reaction (TLC monitoring), 1,4-dioxane was distilled off followed by co-distillation with n-hexane (2 times). The residue was then stirred with water at 90° C. for 2 h followed by filtration to obtain the desired product that was further washed with hot water and then dried. The residue was finally washed with ether to obtain the desired product (2.10 g, 83%). $^1$H NMR (400 MHz, DMSO-d6): δ 1.07 (t, J=7.20 Hz, 3H), 3.17 (quintet, J=6.80 Hz, 2H), 3.86 (s, 3H), 6.65 (br s, 1H), 7.68 (s, 1H), 7.80 (s, 1H) and 10.67 (br s, 1H). MS: 330.08 (M+H)$^+$.

Preparation of 1-ethyl-3-(6-methoxy-5-(pyridin-3-yl) benzo[d]thiazol-2-yl)urea (VII)

Example 71

A solution of 1-(5-bromo-6-methoxybenzo[d]thiazol-2-yl)-3-ethylurea VI (0.20 g, 0.60 mmol), pyridine-3-boronic acid (0.11 g, 0.90 mmol) and K$_3$PO$_4$ (0.20 g, 0.90 mmol) in 1,4-dioxane-MeOH (8.0 mL, 5:3) was degassed by flushing with nitrogen for 15 min. [1,1'-Bis(diphenylphosphino)-ferrocene]dichloropalladium(II), complex with dichloromethane (0.05 g, 0.06 mmol) was then added to the reaction mixture followed by degassing with nitrogen for another 15 min. The resulting reaction mixture was then heated to 80° C. for 2-3 h. After the completion of the reaction (TLC monitoring), the reaction mixture was cooled to room temperature and poured onto ice-cold water followed by extraction with EtOAc (2×100 mL). The combined organics was washed with brine, dried (Na$_2$SO$_4$), filtered and concentrated under reduced pressure. The crude was then purified over silica gel (100-200 M, 3-4% MeOH-DCM) to obtain the desired product that was finally washed with a mixture of 50% DCM-Ether yielding 0.09 g (45%) of the product. $^1$H NMR (400 MHz, DMSO-d6): δ 1.09 (t, J=7.20 Hz, 3H), 3.18 (quintet, J=6.80 Hz, 2H), 3.81 (s, 3H), 6.67 (br s, 1H), 7.44 (m, 1H), 7.56 (s, 1H), 7.69 (s, 1H), 7.93 (m, 1H), 8.53 (d, J=3.60 z, 1H), 8.70 (s, 1H) and 10.62 (br s, 1H). MS: 329.23 (M+H)$^+$. Qualitative HPLC Purity (Acquity BEH C-18, 100×2.1 mm, 246 nm): 99.29% (Rt=4.95 min).

Scheme-36:

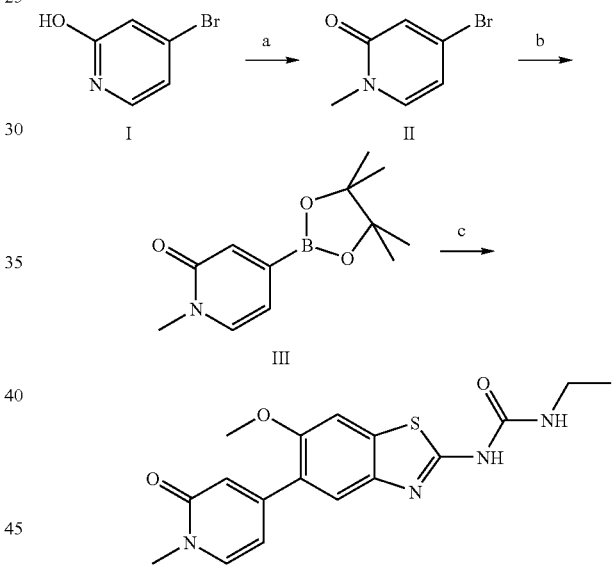

(a) MeI, NaH, THF; (b) Bispinacolatodiboron, KOAc, tricyclohexylphosphine, Pd$_2$(dba)$_3$, 1,4-dioxane; (c) 1-(5-bromo-6-methoxybenzo[d] thiazol-2-yl)-3-ethylurea, K$_3$PO$_4$, Dichlorobis(triphenylphosphine)-palladium(II), DMF—H$_2$O.

Preparation of 4-bromo-1-methylpyridin-2(1H)-one (II)

To an ice-cold solution of 2-hydroxy-4-bromopyridine (1.0 g, 5.75 mmol) in THF (20.0 mL) was added NaH (60% suspension in mineral oil, 0.23 g, 5.75 mmol) portionwise. The reaction mixture was stirred at room temperature for 15 min followed by addition of methyl iodide (1.10 mL, 17.24 mmol). The resulting reaction mixture was stirred at room temperature for 16 h. After the completion of the reaction (TLC monitoring), the reaction mixture was cooled to 0° C., added water and extracted with EtOAc (3×50 mL). The combined organics was washed with brine, dried (Na$_2$SO4), filtered and concentrated under reduced pressure to obtain the desired product (0.99 g, 92%). $^1$H NMR (400 MHz, DMSO-d6): δ 3.38 (s, 3H), 6.44 (dd, J=2.0 and 7.20 Hz, 1H), 6.69 (d, J=2.0 Hz, 1H) and 7.69 (d, J=7.20 Hz, 1H).

Preparation of 1-methyl-4-(4,4,5,5-tetramethyl-1,3,2-dioxaborolan-2-yl)pyridin-2(1H)-one (III)

A solution of 4-bromo-1-methylpyridin-2(1H)-one II (0.50 g, 2.66 mmol), bispinacolatodiboron (0.74 g, 2.93 mmol) and KOAc (0.39 g, 3.99 mmol) in 1,4-dioxane (10.0 mL) was degassed by flushing with nitrogen for 15 min. Tricyclohexylphosphine (0.090 g, 0.32 mmol) and tris(dibenzylideneacetone)dipalladium(0) (0.14 g, 0.13 mmol) was then added to the reaction mixture, which was again degassed by nitrogen for 15 min. The resulting reaction mixture was heated to 80-85° C. for 3 h. After the completion of the reaction (TLC monitoring), the reaction mixture was filtered through celite bed and the filtrate was concentrated to get the crude residue that was carried forward to the next step without further purification. MS: 236.23 (M+H)+.

Preparation of 1-ethyl-3-(6-methoxy-5-(1-methyl-2-oxo-1,2-dihydropyridin-4-yl)benzo[d]thiazol-2-yl) urea (IV)

Example 72

A solution of 1-(5-bromo-6-methoxybenzo[d]thiazol-2-yl)-3-ethylurea (0.10 g, 0.30 mmol), 1-methyl-4-(4,4,5,5-tetramethyl-1,3,2-dioxaborolan-2-yl) pyridin-2(1H)-one III (0.08 g, 0.33 mmol) and K$_3$PO$_4$ (0.10 g, 0.45 mmol) in DMF-H$_2$O (5.0 mL, 3:2) was degassed by flushing with nitrogen for 15 min. Dichlorobis(triphenylphosphine)-palladium(II) (0.02 g, 0.03 mmol) was then added to the reaction mixture followed by degassing with nitrogen for another 15 min. The resulting reaction mixture was then heated to 80° C. for 2 h. After the completion of the reaction (TLC monitoring), the reaction mixture was cooled to room temperature and poured onto ice-cold water followed by extraction with EtOAc (2×100 mL). The combined organics was washed with brine, dried (Na$_2$SO$_4$), filtered and concentrated under reduced pressure. The crude was then purified over silica gel (100-200 M, 3-4% MeOH-DCM) to obtain the desired product that was finally washed with a mixture of 50% DCM-Ether yielding 0.018 g (16%) of the product. $^1$H NMR (400 MHz, DMSO-d6): δ 1.08 (t, J=7.20 Hz, 3H), 3.21 (quintet, J=6.80 Hz, 2H), 3.44 (s, 3H), 3.81 (s, 3H), 6.39 (dd, J=1.60 and 6.80 Hz, 1H), 6.48 (d, J=1.20 Hz, 1H), 6.67 (br s, 1H), 7.51. (s, 1H), 7.67 (m, 2H) and 10.64 (br s, 1H). MS: 359.20 (M+H)+. Qualitative HPLC Purity (Acquity BEH C-18, 100×2.1 mm, 237 nm): 94.71% (Rt=4.52 min).

Scheme-37:

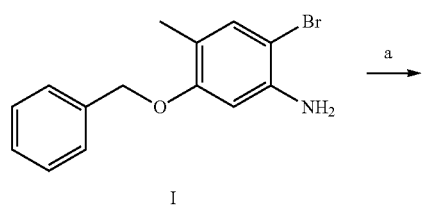

I

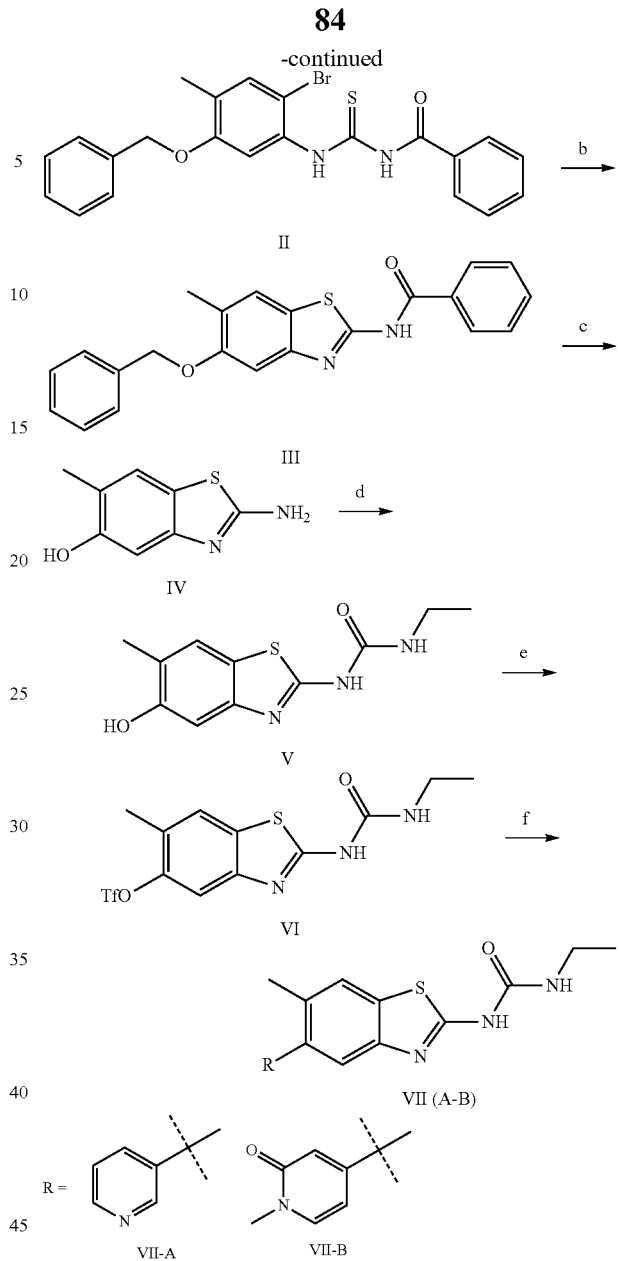

(a) Benzoylisothiocyanate, acetone; (b) Pd$_2$(dba)$_3$, dppf, KO$^t$Bu, 1,4-dioxane, 80° C., 20 h; (c) 70% Conc. H$_2$SO$_4$, 140° C., 1 h; (d) Ethylisocyanate, 1,4- dioxane, 70° C., 8-10 h (e) N-Phenyltriflimide, DIPEA, DMF; (f) pyridine-3-boronic acid (for VII-A), K$_3$PO$_4$, PdCl$_2$(dppf), 1,4-dioxane:methanol, 80° C., 2 h, or bis(neopentylglycolatodiboron, KOAc, DMSO, 4-bromo-1-methylpyridin-2(1H)-one, Cs$_2$CO$_3$, Pd(PPh$_3$)$_4$, 80° C., 16 h.

Preparation of 1-Benzoyl-3-(5-benzyloxy-2-bromo-4-methyl-phenyl)-thiourea (II)

To a solution of 5-benzyloxy-2-bromo-4-methyl-phenylamine (0.50 g, 1.71 mmol) in acetone (20 mL) was added benzoylisothiocyanate (0.28 mL, 2.08 mmol) dropwise at room temperature. The resulting reaction mixture was stirred for 30 min. at the same temperature. After completion of reaction (TLC monitoring), acetone was distilled off, the solid residue was stirred in hexane for 5-10 min and then filtered to obtain the desired product as white solid (0.70 g, 88%). $^1$H NMR (400 MHz, DMSO-d6): δ 2.20 (s, 3H), 5.10 (s, 2H), 7.33 (m, 1H), 7.40 (t, J=7.20 Hz, 2H), 7.48 (d, J=7.60

Hz, 2H), 7.55 (m, 3H), 7.67 (m, 1H), 7.73 (s, 1H), 8.0 (d, J=7.20 Hz, 2H), 11.81 (br s, 1H) and 12.59 (br s, 1H).

Preparation of N-(5-Benzyloxy-6-methyl-benzothiazol-2-yl)-benzamide (III)

To a solution of 1-benzoyl-3-(5-benzyloxy-2-bromo-4-methyl-phenyl)-thiourea II (1.0 g, 2.20 mmol) in 1,4-dioxane (30 mL) was added sequentially $Pd_2(dba)_3$ (0.12 g, 0.12 mmol), dppf (0.07 g, 0.12 mmol) and KO$^t$Bu (0.75 g, 3.30 mmol) at room temperature under $N_2$ atmosphere. The resulting reaction mixture was heated at 80° C. for 6 h. After completion of reaction (TLC monitoring), the reaction mixture was diluted with EtOAc and filtered through celite bed-bed. The filtrate was concentrated and purified over silica gel (100-200 M, 20% EtOAc-Hexane) to obtain the desired product (0.50 g, 61%). $^1$H NMR (400 MHz, DMSO-d6): δ 2.31 (s, 3H), 5.23 (s, 2H), 7.33 (m, 1H), 7.39 (m, 3H), 7.52 (m, 2H), 7.54 (m, 2H), 7.64 (m, 1H), 7.76 (s, 1H), 8.13 (d, J=7.60 Hz, 2H) and 12.77 (br s, 1H). MS: 375.19 (M+H)$^+$.

Preparation of 2-amino-6-methyl-benzothiazol-5-ol (IV)

To an ice-cooled solution of N-(5-benzyloxy-6-methyl-benzothiazol-2-yl)-benzamide (0.60 g, 1.60 mmol) was added 70% aq. $H_2SO_4$ (5-6 mL). The resulting mixture was heated to 140° C. for 1 h. After completion of reaction (TLC monitoring), the reaction mixture was basified with aq. $Na_2CO_3$ solution (pH 10) and extracted with EtOAc (2×300 mL). The organic layers were combined and washed with brine solution, dried over $Na_2SO_4$, filtered and concentrated to obtain the desired product as a white solid (0.20 g, 70%). MS: 181.16 (M+H)$^+$.

Preparation of 1-ethyl-3-(5-hydroxy-6-methyl-benzothiazol-2-yl)-urea (V)

To the solution of 2-amino-6-methyl-benzothiazol-5-ol (0.20 g, 1.11 mmol) in 1,4-dioxane (5 mL) was added ethyl-isocyanate (0.13 mL, 1.68 mmol) at room temperature. The resulting mixture was heated to 60-65° C. for 16 h. After completion of reaction (TLC monitoring), 1,4-dioxane was distilled off and co-evaporated with hexane (twice). The solid residue was treated with water to 60-70° C. for 2-4 h. The resulting solid was filtered off and dried under vacuum to obtain the white solid compound (0.17 g, 61%). $^1$H NMR (DMSO-d6, 400 MHz): δ 1.07 (t, J=7.20 Hz, 3H), 2.17 (s, 3H), 3.16 (m, 2H), 6.68 (br s, 1H), 7.00 (s, 1H), 7.47 (s, 1H), 9.33 (s, 1H), and 10.43 (br s, 1H), MS: 252.18 (M+H$^+$).

Preparation of 2-(3-ethylureido)-6-methylbenzo[d]thiazol-5-yl trifluoromethanesulfonate (VI)

To a solution of 1-ethyl-3-(5-hydroxy-6-methyl-benzothiazol-2-yl)-urea (0.185 g, 0.74 mmol) in DMF (3 ml) was added DIPEA (0.22 mL, 1.21 mmol) and the resulting solution was stirred at room temperature for 5 min. followed by portion-wise addition of N-phenyltriflimide (0.36 g, 0.99 mmol). The reaction mixture was stirred for 2 h at room temperature. After completion of reaction (TLC monitoring), the reaction mixture was quenched with cold water and extracted with EtOAc. The organic layers were combined, dried over $Na_2SO_4$ and evaporated upto dryness. The crude residue was purified over silica gel (100-200 M, 1.5% MeOH-DCM) to obtain the desired product as white solid compound (0.10 g, 38%). MS: 384.11 (M+H$^+$).

Preparation of 1-ethyl-3-(6-methyl-5-(pyridin-3-yl) benzo[d]thiazol-2-yl)urea (VII-A)

Example 73

To a solution of 2-(3-ethylureido)-6-methylbenzo[d]thiazol-5-yl trifluoromethanesulfonate VI (0.08 g, 0.21 mmol) in 1,4-dioxane:MeOH (8.0 mL, 5:3) was added pyridine-3-boronic acid (0.03 g, 0.25 mmol) and potassium phosphate (0.05 g, 0.25 mmol) at room temperature under $N_2$ atmosphere. The resulting mixture was degassed for 15 min. followed by addition of $PdCl_2$(dppf) (0.025 g, 0.03 mmol) and again degassed for 15 min. The reaction mixture was then heated to 80° C. for 2 h. After completion of reaction (TLC monitoring), the reaction mixture was diluted with methanol and filtered through celite bed-bed. The filtrate was distilled off, the crude residue was purified over silica gel (100-200 M, 2.5%) MeOH-DCM) to obtain the desired product as off-white solid (0.015 g, 23%). $^1$H NMR (DMSO-d$_6$, 400 MHz): δ 1.08 (t, J=7.20 Hz, 3H), 2.32 (s, 3H), 3.20 (m, 2H), 6.70 (br s, 1H), 7.46 (s, 2H), 7.55 (m, 1H), 7.84 (m, 2H), 8.59 (s, 1H), and 10.70 (br s, 1H). MS: 313.15 (M+H$^+$). Qualitative HPLC Purity (Acquity BEH C-18, 2.1×100 mm, 220 nm): 90.14% (Rt=5.22 min).

Preparation of 1-ethyl-3-(6-methyl-5-(1-methyl-2-oxo-1,2-dihydropyridin-4-yl)benzo[d]thiazol-2-yl) urea (VII-B)

Example 74

To a solution of 2-(3-ethylureido)-6-methylbenzo[d]thiazol-5-yl trifluoromethanesulfonate VI (0.122 g, 0.32 mmol) in DMSO (8 mL) was added KOAc (0.09 g, 0.95 mmol) and bis(neopentyl glycolato)diboron (0.15 g, 0.64 mmol) at room temperature. The resulting mixture was degassed by nitrogen for 15-20 min. followed by the addition of $PdCl_2$.dppf (0.03 g, 0.03 mmol). The reaction mixture was again degassed for 15-20 min and then heated up to 80° C. for 3 h. After completion of reaction (TLC monitoring), the reaction mixture was cooled to room temperature followed by addition of 4-bromo-1-methylpyridin-2(1H)-one (0.12 g, 0.64 mmol) and $Cs_2CO_3$ (0.16 g, 3.7 M in $H_2O$). The resulting mixture was degassed for 10-15 min. followed by the addition of $Pd(PPh_3)_4$ (0.04 g, 0.03 mmol) and again degassed for 15-20 min and finally heated to 80° C. for 16 h. After completion of reaction (TLC monitoring), water was added to the reaction mixture and extracted with EtOAc (3×50 mL). The combined organics was dried over $Na_2SO_4$ and concentrated. The crude residue was purified over silica gel (100-200 M, 2-2.5% MeOH-DCM) to obtain the desired product as white solid (0.025 g, 24%). $^1$H NMR (DMSO-d6, 400 MHz): δ 1.08 (t, J=7.20 Hz, 3H), 2.31 (s, 3H), 3.19 (m, 2H), 3.46 (s, 3H), 6.27 (dd, J=1.60 and 6.80 Hz, 1H), 6.32 (s, 1H), 6.70 (br s, 1H), 7.41 (s, 1H), 7.74 (d, J=6.80 Hz, 1H), 7.78 (s, 1H) and 10.71 (br s, 1H). MS: 343.18 (M+H$^+$). Qualitative HPLC Purity (Acquity BEH C-18, 2.1×100 mm, 237 nm): 98.53% (Rt=4.65 min).

Scheme-38:

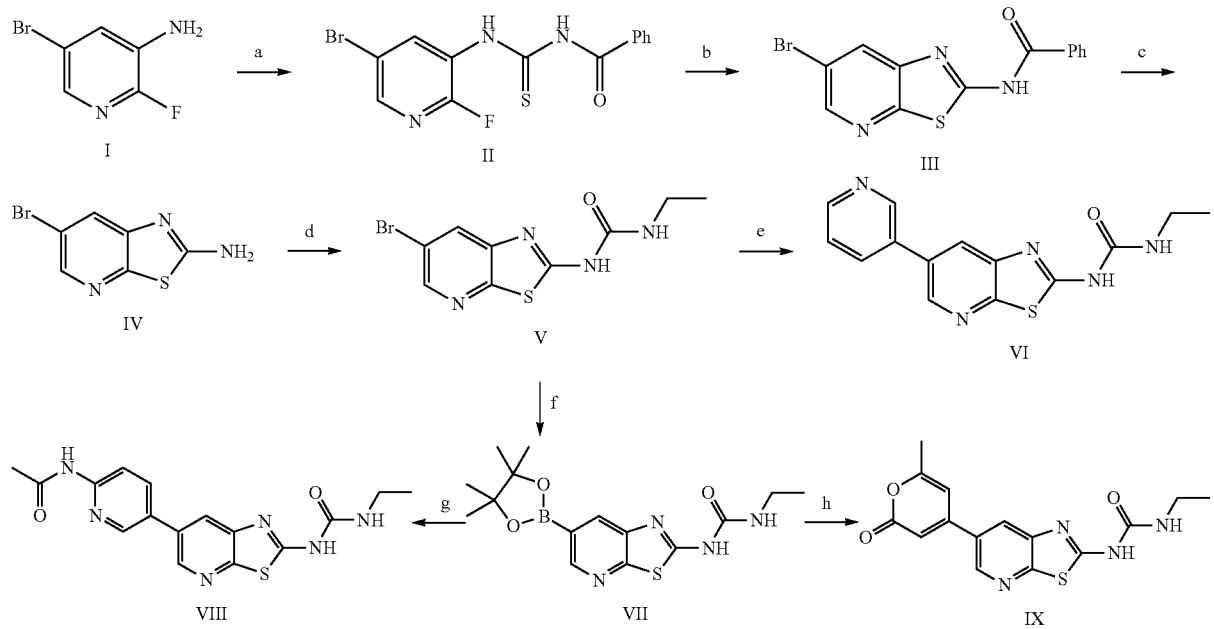

(a) Benzoylisothiocyanate, acetone, room temperature, 30 min; (b) NaOH—THF; (c) 70% $H_2SO_4$, 100° C., 45 min; (d) Ethylisocyanate, 1,4-dioxane; (e) pyridine-3-boronic acid, $K_3PO_4$, $PdCl_2(PPh_3)_2$, DMF—$H_2O$; (f) Bispinacolatodiboron, KOAc, tricyclohexylphosphine, $Pd_2(dba)_3$, 1,4-dioxane; (g) N-(5-bromopyridin-2-yl)acetamide, $K_3PO_4$, $PdCl_2(PPh_3)_2$, DMF—$H_2O$; (h) 4-bromo-6-methyl-2H-pyran-2-one, $K_3PO_4$, $PdCl_2(dppf)$, DMF—$H_2O$, 80° C., 16 h.

Preparation of N-(5-bromo-2-fluoropyridin-3-ylcarbamothioyl)benzamide (II)

To a solution of 3-amino-5-bromo-2-fluoropyridine (1.0 g, 5.23 mmol) in acetone (15.0 mL) was added benzoylisothiocyanate (0.85 mL, 6.25 mmol) and the resulting reaction mixture was stirred at room temperature for 30 min. After the completion of the reaction (TLC monitoring), acetone was removed under reduced pressure and the residue was washed with hexane and filtered to obtain the desired product (1.68 g, 91%). $^1$H NMR (400 MHz, DMSO-d6): δ 7.55 (t, J=7.60 Hz, 2H), 7.68 (t, J=7.60 Hz, 1H), 8.0 (d, J=7.60 Hz, 2H), 8.31 (s, 1H), 8.84 (dd, J=2.0 and 8.40 Hz, 1H), 12.03 (br s, 1H) and 12.60 (br s, 1H).

Preparation of N-(6-bromothiazolo[5,4-b]pyridin-2-yl)benzamide (III)

To an ice-cold solution of N-(5-bromo-2-fluoropyridin-3-ylcarbamothioyl)benzamide II (1.80 g, 5.08 mmol) in THF (20.0 mL) was added a solution of NaOH (1.0 g, 22.0 mmol, dissolved in 10.0 mL $H_2O$). The reaction mixture was then heated to 60° C. for 16 h. After the completion of the reaction (TLC monitoring), the reaction mixture was concentrated, added water and extracted with EtOAc (3×150 mL). The combined organics was washed with brine, dried ($Na_2SO_4$), filtered and concentrated under reduced pressure to obtain the desired product (1.60 g, 95%). $^1$H NMR (400 MHz, DMSO-d6): δ 7.42 (m, 3H), 7.82 (d, J=2.0 Hz, 1H), 8.14 (m, 2H) and 8.18 (d, J=2.0 Hz, 1H).

Preparation of 6-bromothiazolo[5,4-b]pyridin-2-amine (IV)

A solution of N-(6-bromothiazolo[5,4-b]pyridin-2-yl)benzamide III (2.0 g, 5.98 mmol) in 70% $H_2SO_4$ (10.0 mL) was heated to 140° C. for 1 h. After the completion of the reaction (TLC monitoring), the reaction mixture was poured onto crushed ice, basified with 30% aqueous NaOH solution till pH 8.0 and extracted with EtOAc (3×150 mL). The combined organics was washed with brine, dried ($Na_2SO_4$), filtered and concentrated under reduced pressure to obtain the desired product (1.34 g, 98%). $^1$H NMR (400 MHz, DMSO-d6): δ 7.85 (d, J=2.0 Hz, 1H), 8.05 (br s, 2H) and 8.18 (d, J=2.0 Hz, 1H).

Preparation of 1-(6-bromothiazolo[5,4-b]pyridin-2-yl)-3-ethylurea (V)

To a solution of 6-bromothiazolo[5,4-b]pyridin-2-amine IV (1.30 g, 5.55 mmol) in 1,4-dioxane (20.0 mL) was added ethylisocyanate (2.19 mL, 27.07 mmol) and the resulting reaction mixture was heated to 80° C. for 8 h. After the completion of the reaction (TLC monitoring), 1,4-dioxane was distilled off followed by co-distillation with n-hexane (2 times). The residue was then stirred with water at 90° C. for 2 h followed by filtration to obtain the desired product that was further washed with hot water and then dried. The residue was finally washed with ether to obtain the desired product (1.40 g, 83%). $^1$H NMR (400 MHz, DMSO-d6): δ 1.10 (t, J=7.20 Hz, 3H), 3.20 (quintet, J=7.20 Hz, 2H), 6.76 (br s, 1H), 8.24 (d, J=2.0 Hz, 1H), 8.45 (d, J=2.0 Hz, 1H) and 11.05 (br s, 1H).

Preparation of 1-ethyl-3-(6-(pyridin-3-yl)thiazolo[5,4-b]pyridin-2-yl)urea (VI)

Example 75

A solution of 1-(6-bromothiazolo[5,4-b]pyridin-2-yl)-3-ethylurea (0.05 g, 0.17 mmol), pyridine-3-boronic acid (0.025 g, 0.20 mmol) and $K_3PO_4$ (0.053 g, 0.25 mmol) in DMF-$H_2O$ (5.0 mL, 3:2) was degassed by flushing with nitrogen for 15 min. Dichlorobis(triphenylphosphine)-palladium (II) (0.012 g, 0.016 mmol) was then added to the reaction mixture followed by degassing with nitrogen for another 15 min. The resulting reaction mixture was then heated to 80° C. for 4 h. After the completion of the reaction (TLC monitoring), the reaction mixture was cooled to room temperature and poured onto ice-cold water followed by extraction with EtOAc (2×100 mL). The combined organics was washed with brine, dried (Na$_2$SO$_4$), filtered and concentrated under reduced pressure. The crude was then purified over silica gel (100-200 M, 2.40% MeOH-DCM) to obtain the desired product (0.003 g (7%). $^1$H NMR (400 MHz, DMSO-d6): δ 1.10 (t, J=7.20 Hz, 3H), 3.18 (m, 2H), 6.77 (m, 1H), 7.55 (m, 1H), 8.22 (d, J=8.40 Hz, 1H), 8.31 (d, J=1.60 Hz, 1H), 8.63 (d, J=5.20 Hz, 1H), 8.72 (d, J=2.0 Hz, 1H), 9.01 (d, J=1.60 Hz, 1H), and 10.97 (br s, 1H). MS: 300.11 (M+H)$^+$. Qualitative HPLC Purity (Acquity BEH C-18, 100×2.1 mm, 245 nm): 97.04% (Rt=4.40 min).

Preparation of 1-ethyl-3-(6-(4,4,5,5-tetramethyl-1,3,2-dioxaborolan-2-yl)thiazolo[5,4-b]pyridin-2-yl)urea (VII)

A solution of 1-(6-bromothiazolo[5,4-b]pyridin-2-yl)-3-ethylurea V (0.20 g, 0.66 mmol), bispinacolatodiboron (0.38 g, 1.32 mmol) and KOAc (0.164 g, 2.0 mmol) in 1,4-dioxane (10.0 mL) was degassed by flushing with nitrogen for 15 min. Tricyclohexylphosphine (0.03 g, 0.10 mmol) and tris(dibenzylideneacetone)dipalladium(0) (0.06 g, 0.066 mmol) was then added to the reaction mixture, which was again degassed by nitrogen for 15 min. The resulting reaction mixture was heated to 80-85° C. for 2 h. After the completion of the reaction (TLC monitoring), the reaction mixture was filtered through celite bed and the filtrate was concentrated to get the crude residue that was carried forward to the next step without further purification. MS: 349.23 (M+H)$^+$.

Preparation of N-(5-(2-(3-ethylureido)thiazolo[5,4-b]pyridin-6-yl)pyridin-2-yl)acetamide (VIII)

Example 76

A solution of N-(5-bromopyridin-2-yl)acetamide (0.06 g, 0.28 mmol), 1-ethyl-3-(6-(4,4,5,5-tetramethyl-1,3,2-dioxaborolan-2-yl) thiazolo[5,4-b]pyridin-2-yl)urea (0.15 g, 0.42 mmol) and K$_3$PO$_4$ (0.18 g, 0.84 mmol) in DMF-H$_2$O (5.0 mL, 3:2) was degassed by flushing with nitrogen for 15 min. Dichlorobis(triphenylphosphine)-palladium(II) (0.03 g, 0.04 mmol) was then added to the reaction mixture followed by degassing with nitrogen for another 15 min. The resulting reaction mixture was then heated to 80° C. for 16 h. After the completion of the reaction (TLC monitoring), the reaction mixture was cooled to room temperature and poured onto ice-cold water followed by extraction with EtOAc (2×100 mL). The combined organics was washed with brine, dried (Na$_2$SO$_4$), filtered and concentrated under reduced pressure. The crude was then purified over silica gel (100-200 M, 2.80% MeOH-DCM) to obtain the desired product (0.007 g (5%). $^1$H NMR (400 MHz, DMSO-d6): δ 1.11 (t, J=7.20 Hz, 3H), 2.12 (s, 3H), 3.18 (m, 2H), 6.76 (m, 1H), 8.17-8.28 (m, 3H), 8.71 (d, J=1.60 Hz, 1H), 8.75 (s, 1H), 10.72 (s, 1H) and 10.96 (br s, 1H). MS: 357.15 (M+H)$^+$. Qualitative HPLC Purity (Acquity BEH C-18, 100×2.1 mm, 238 nm): 89.81% (Rt=4.37 min).

Preparation of 1-ethyl-3-(6-(6-methyl-2-oxo-2H-pyran-4-yl) thiazolo[5,4-b]pyridin-2-yl)urea (IX)

Example 77

A solution of 4-bromo-6-methyl-2H-pyran-2-one (0.055 g, 0.30 mmol), 1-ethyl-3-(6-(4,4,5,5-tetramethyl-1,3,2-dioxaborolan-2-yl) thiazolo[5,4-b]pyridin-2-yl)urea (0.15 g, 0.42 mmol) and K$_3$PO$_4$ (0.185 g, 0.87 mmol) in DMF-H$_2$O (5.0 mL, 3:2) was degassed by flushing with nitrogen for 15 min. [1,1'-Bis(diphenylphosphino)-ferrocene]dichloropalladium (II), complex with dichloromethane (0.021 g, 0.028 mmol) was then added to the reaction mixture followed by degassing with nitrogen for another 15 min. The resulting reaction mixture was then heated to 80° C. for 16 h. After the completion of the reaction (TLC monitoring), the reaction mixture was cooled to room temperature and poured onto ice-cold water followed by extraction with EtOAc (2×100 mL). The combined organics was washed with brine, dried (Na$_2$SO$_4$), filtered and concentrated under reduced pressure. The crude was then purified over silica gel (100-200 M, 4.20% MeOH-DCM) to obtain the desired product (0.032 g (33%). $^1$H NMR (400 MHz, DMSO-d6): δ 1.11 (t, J=6.80 Hz, 3H), 2.31 (s, 3H), 3.21 (quintet, J=7.20 Hz, 2H), 6.71 (s, 1H), 6.75 (m, 1H), 6.90 (s, 1H), 8.40 (s, 1H), 8.79 (s, 1H) and 11.07 (br s, 1H). MS: 331.10 (M+H)$^+$. Qualitative HPLC Purity (Acquity BEH C-18, 100×2.1 mm, 261 nm): 96.37% (Rt=4.72 min).

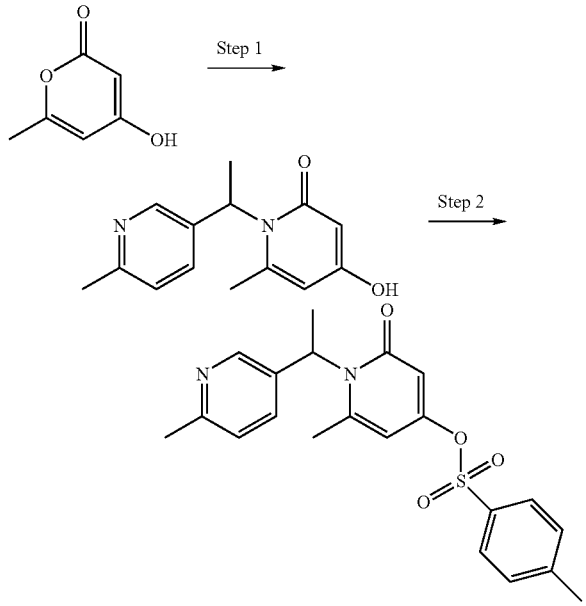

Scheme-39

Preparation of 4-Hydroxy-6-methyl-1-[1-(6-methyl-pyridin-3-yl)-ethyl]-1H-pyridin-2-one (Step 1)

A stirred mixture of 4-Hydroxy-6-methyl-2-pyrone (1.394 g, 11.1 mmol) and 1-(6-Methyl-pyridin-3-yl)-ethylamine (1.806 g, 13.3 mmol) in water (18 ml) was boiled under reflux for 65 h. The mixture was cooled to ambient temperature and the supernatant liquid was decanted off to leave a dark semi-solid residue. This was triturated with ethyl acetate to give 4-Hydroxy-6-methyl-1-[1-(6-methyl-pyridin-3-yl)-ethyl]-1H-pyridin-2-one as a grey solid (475 mg) which was used in the next step without further purification. LC-MS m/z 245 [M+H]$^+$ Rt=1.21 min.

Preparation of Toluene-4-sulfonic acid 6-methyl-1-[1-(6-methyl-pyridin-3-yl)-ethyl]-2-oxo-1,2-dihydro-pyridin-4-yl ester (Step 2)

A stirred mixture of the product from Step 1 (475 mg, 1.947 mmol) and 4-methylbenzenesulfonyl chloride (371 mg, 1.947 mmol) in anhydrous dichloromethane (16 ml) was treated with anhydrous triethylamine (0.81 ml, 5.839 ml) and stirring was continued at ambient temperature for 18 h. The reaction mixture was diluted with dichloromethane (150 ml), washed with water (100 ml) followed by brine (100 ml) and dried (MgSO₄). The solvent was removed in vacuo and the residue purified by flash silica chromatography eluting with ethyl acetate to give toluene-4-sulfonic acid 6-methyl-1-[1-(6-methyl-pyridin-3-yl)-ethyl]-2-oxo-1,2-dihydro-pyridin-4-yl ester (609 mg) as a colourless gum which solidified on standing. LC-MS m/z 399 [M+H]⁺ Rt=2.10 min.

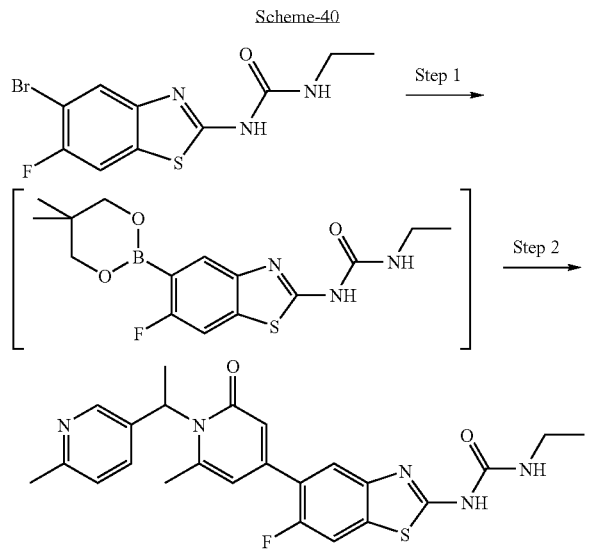

Preparation of 1-[5-(5,5-Dimethyl-[1,3,2]dioxaborinan-2-yl)-6-fluoro-benzothiazol-2-yl]-3-ethyl-urea (Step 1)

A stirred mixture of 1-(5-Bromo-6-fluoro-benzothiazol-2-yl)-3-ethyl-urea (100 mg, 0.314 mmol), bis(neopentyl)glycolato diboron (70 mg, 0.314 mmol), potassium acetate (91 mg, 0.952 mmol) and 1,1'-bis(diphenylphosphino)ferrocene palladium(II)chloride, complex (26 mg, 0.0314 mmol) in anhydrous N,N-dimethylformamide (4.1 ml) was purged with nitrogen for 15 minutes. The reaction vessel was sealed and heated at 80° C. for 3 h.

Preparation of 1-Ethyl-3-(6-fluoro-5-{6-methyl-1-[1-(6-methyl-pyridin-3-yl)-ethyl]-2-oxo-1,2-dihydro-pyridin-4-yl}-benzothiazol-2-yl)-urea (Step 2)

Example 78

The reaction mixture from Step 1 was cooled to ambient temperature. Toluene-4-sulfonic acid 6-methyl-1-[1-(6-methyl-pyridin-3-yl)-ethyl]-2-oxo-1,2-dihydro-pyridin-4-yl ester (125 mg, 0.314 mmol) was added followed by aqueous cesium carbonate solution (3.7 M, 0.12 ml, 0.470 mmol) and 1,1'-bis(diphenylphosphino)ferrocene palladium(II)chloride, complex (26 mg, 0.0314 mmol). The reaction mixture was purged with nitrogen for 5 minutes, sealed and heated at 80° C. for 5 h. The reaction mixture was cooled to ambient temperature, diluted with water (100 ml) and extracted with ethyl acetate (3×50 ml). The combined extracts were washed with brine and dried (MgSO₄). The solvent was removed in vacuo and the residue purified by flash silica chromatography eluting first with ethyl acetate and then with 0 to 5% (7 N methanolic ammonia in dichloromethane to give 1-ethyl-3-(6-fluoro-5-{6-methyl-1-[1-(6-methyl-pyridin-3-yl)-ethyl]-2-oxo-1,2-dihydro-pyridin-4-yl}-benzothiazol-2-yl)-urea (Example 78) as a pale brown solid (30 mg). LC-MS m/z 466 [M+H]⁺ Rt=2.65 min.

Scheme-41
Preparation of 4-Bromo-1-(3-methoxy-pyridin-2-ylmethyl)-1H-pyridin-2-one (3-Methoxy-pyridin-2-yl)-methanol (227 mg, 1.63 mmol), 2-hydroxy-4-bromopyridine (282 mg, 1.63 mmol) and triphenyl phosphine (416 mg, 1.63 mmol) were stirred in dry dichloromethane (10 ml) at 0° C. under an atmosphere of nitrogen. Diethyl azodicarboxylate (242 mg, 1.63 mmol) was added at 0° C. then the reaction was allowed to attain room with stirring overnight. A saturated aqueous solution of sodium hydrogen carbonate was added (10 ml) and the layers were separated. The aqueous portion was extracted with dichloromethane (2×10 ml) and the organic portions were combined, dried (MgSO₄) and concentrated under reduced pressure. The crude product was purified by flash silica chromatography eluting first with 0-100% ethyl acetate in petrol and then 10% 7 N methanolic ammonia in dichloromethane to give the 4-bromo-1-(3-methoxy-pyridin-2-ylmethyl)-1H-pyridin-2-one in 57% purity contaminated with 23% 2-hydroxy-4-bromopyridine and 20% triphenyl phosphine oxide by LC-MS (340 mg). The product was used directly in the next step. LC-MS m/z 297 [M+H]⁺ Rt=2.05 min

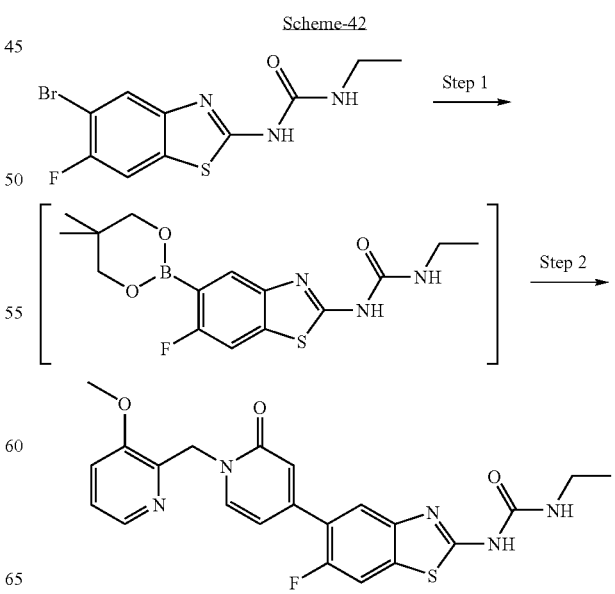

Preparation of 1-[5-(5,5-Dimethyl-[1,3,2]dioxaborinan-2-yl)-6-fluoro-benzothiazol-2-yl]-3-ethyl-urea (Step 1)

A stirred mixture of 1-(5-Bromo-6-fluoro-benzothiazol-2-yl)-3-ethyl-urea (100 mg, 0.314 mmol), bis(neopentyl)glycolato diboron (70 mg, 0.314 mmol), potassium acetate (91 mg, 0.952 mmol) and 1,1'-bis(diphenylphosphino)ferrocene palladium(II)chloride, complex (26 mg, 0.0314 mmol) in anhydrous N,N-dimethylformamide (4.1 ml) was purged with nitrogen for 15 minutes. The reaction vessel was sealed and heated at 80° C. for 3 h.

Preparation of 1-Ethyl-3-{6-fluoro-5-[1-(3-methoxy-pyridin-2-ylmethyl)-2-oxo-1,2-dihydro-pyridin-4-yl]-benzothiazol-2-yl}-urea (Step 2)

Example 79

The reaction mixture from Step 1 was cooled to ambient temperature. The mixture containing 4-Bromo-1-(3-methoxy-pyridin-2-ylmethyl)-1H-pyridin-2-one (114 mg) was added followed by aqueous cesium carbonate solution (3.7 M, 0.25 ml, 0.930 mmol) and 1,1'-bis(diphenylphosphino)ferrocene palladium(II)chloride complex (26 mg, 0.0314 mmol). The reaction mixture was purged with nitrogen for 5 minutes, sealed and heated at 80° C. for 5 h. The reaction mixture was cooled to ambient temperature, diluted with water (12 ml) and extracted with dichloromethane (3×12 ml). The combined extracts were washed with brine, dried (MgSO$_4$) and concentrated under reduced pressure. The crude product was triturated in dichloromethane-methanol (9:1) and the resulting solid was collected by filtration to afford 1-Ethyl-3-{6-fluoro-5-[1-(3-methoxy-pyridin-2-ylmethyl)-2-oxo-1,2-dihydro-pyridin-4-yl]-benzothiazol-2-yl}-urea (Example 79) (10 mg) as a white solid. The filtrate was concentrated under reduced pressure and purified by flash silica chromatography eluting with 0 to 5% 7 N methanolic ammonia in dichloromethane to give a further 8 mg of product as a white solid. LC-MS m/z 454 [M+H]$^+$ Rt=2.64 min.

Biological Data

Minimum Inhibitory Concentration (MIC) Testing

Compounds of this invention were tested for antimicrobial activity by susceptibility testing in liquid or on solid media. MICs for compounds against each strain were determined by the broth microdilution or agar dilution method according to the guidelines of the Clinical Laboratories and Standards Institute, formerly the National Committee for Clinical Laboratory Standards (Clinical Laboratories and Standards Institute. *Methods for Dilution Antimicrobial Susceptibility Tests for Bacteria That Grow Aerobically; Approved Standard—Seventh Edition*. Document M7-A7. CLSI, Wayne, Pa., 2006; Clinical Laboratories and Standards Institute. *Methods for Antimicrobial Susceptibility Testing of Anaerobic Bacteria; Approved Standard—Sixth Edition*. Document M11-A6. CLSI, Wayne, Pa., 2004).

Compounds of the current invention were found to have antimicrobial activity in the MIC assays described above.

Gyrase ATPase Assay

Gyrase converts ATP into ADP and inorganic phosphate. The released phosphate can be detected by the addition of malachite green solution and measured by monitoring the increase in absorbance at 600 nm.

The ATPase assay is carried out in a buffer containing 4.8 μg/ml Gyrase enzyme (A$_2$B$_2$ complex from *Escherichia coli*), 0.08 μg/ml ssDNA, 35 mM Tris pH 7.5, 24 mM KCl, 2 mM MgCl$_2$, 6.5% Glycerol, 2 mM DTT, 1.8 mM Spermidine, 0.5 mg/ml BSA, and 5% DMSO solution containing the inhibitor. The reaction is started by adding ATP to a final concentration of 1 mM and allowed to incubate at 30° C. for 60 minutes. The reaction is stopped by adding 200 μl of malachite green solution (0.034% malachite green, 10 mM ammonium molybdate, 1 M HCl, 3.4% ethanol, 0.01% tween 20). Colour is allowed to develop for 5 minutes and the absorbance at 600 nm is measured spectrophotometrically. The IC$_{50}$ values are determined from the absorbance readings using no compound and no enzyme controls.

All Example compounds above of the current invention were found to inhibit the gyrase ATPase assay described above, with 50% inhibitory concentrations (IC$_{50}$) of less than 0.75 micro molar.

All of the Examples inhibited the growth of bacteria. Table 1 shows the MIC value for each Example against *Enterococcus faecalis* ATCC 29212 in the MIC Assay described above. Examples with activity "C" demonstrate MICs of 2-16 μg/ml. Examples with activity "B" demonstrate MICs of 0.25-1 μg/ml. Examples with activity "A" demonstrate MICs of <0.25 μg/ml.

TABLE 1

MICs against *Enterococcus faecalis*

| Example number | Activity |
|---|---|
| 1 | B |
| 2 | C |
| 3 | B |
| 4 | B |
| 5 | C |
| 6 | C |
| 7 | C |
| 8 | C |
| 9 | C |
| 10 | C |
| 11 | C |
| 12 | C |
| 13 | C |
| 14 | C |
| 15 | C |
| 16 | C |
| 17 | C |
| 18 | C |
| 19 | B |
| 20 | B |
| 21 | C |
| 22 | C |
| 23 | C |
| 24 | C |
| 25 | B |
| 26 | C |
| 27 | C |
| 28 | C |
| 29 | C |
| 30 | B |
| 31 | B |
| 32 | C |
| 33 | B |
| 34 | B |
| 35 | B |
| 36 | C |
| 37 | C |
| 38 | B |
| 39 | C |
| 40 | B |
| 41 | C |
| 42 | C |
| 43 | B |
| 44 | A |
| 45 | B |
| 46 | B |
| 47 | C |

TABLE 1-continued

MICs against *Enterococcus faecalis*

| Example number | Activity |
|---|---|
| 48 | B |
| 49 | B |
| 50 | C |
| 51 | C |
| 52 | B |
| 53 | C |
| 54 | C |
| 55 | B |
| 56 | C |
| 57 | C |
| 58 | B |
| 59 | B |
| 60 | B |
| 61 | B |
| 62 | B |
| 63 | C |
| 64 | B |
| 65 | B |
| 66 | C |
| 67 | C |
| 68 | C |
| 69 | C |
| 70 | C |
| 71 | B |
| 72 | B |
| 73 | C |
| 74 | B |
| 75 | C |
| 76 | C |
| 77 | C |
| 78 | B |
| 79 | A |

Some of the Example compounds were also tested for activity against other bacterial species. For example, Table 2 shows the MICs of Example 3 against various bacterial species. Activity "C" demonstrates an MIC of 2-16 μg/ml. Activity "B" demonstrates an MIC of 0.25-1 μg/ml. Activity "A" demonstrates an MIC of <0.25 μg/ml.

TABLE 2

MICs against various bacteria

| Species | Isolate ID | Activity |
|---|---|---|
| *Enterococcus faecalis* (VRE) | ATCC 51299 | C |
| *Enterococcus faecium* (VRE) | ATCC 700221 | C |
| *Haemophilus influenzae* | ATCC 49247 | C |
| *Moraxella catarrhalis* | ATCC 25240 | B |
| *Staphylococcus aureus* | ATCC 29213 | B |
| *Staphylococcus epidermidis* | ATCC 12228 | B |
| *Staphylococcus haemolyticus* | ATCC 29970 | B |
| *Streptococcus agalactiae* | ATCC 13813 | B |
| *Streptococcus mutans* | ATCC 35668 | B |
| *Streptococcus pneumoniae* | ATCC 49619 | A |
| *Streptococcus pyogenes* | ATCC 51339 | B |

Some of the Example compounds were also tested for activity against clinical isolates of various bacterial species. For example, Table 3 shows the $MIC_{90}$s of Example 49 against various bacterial species.

TABLE 3

| MICs against various clinical isolates Species | Number of isolates | MIC range (μg/ml) | $MIC_{90}$ (μg/ml) |
|---|---|---|---|
| *Staphylococcus aureus* | 10 | 0.03-0.12 | 0.06 |
| *Staphylococcus epidermidis* | 10 | 0.008-0.06 | 0.03 |
| *Streptococcus pyogenes* | 10 | 0.12-0.5 | 0.25 |
| *Streptococcus pneumoniae* | 10 | 0.008-0.03 | 0.015 |
| *Propionibacterium acnes* | 5 | 1 | 1 |
| *Enterococcus faecium* | 10 | 0.25-0.5 | 0.5 |
| *Enterococcus faecalis* | 10 | 0.06-0.5 | 0.25 |

The invention claimed is:

1. A compound of formula (I) or a salt or N-oxide thereof:

$$R_2 \text{—benzothiazole—NH—X—[Alk]}_m\text{-Q} \quad (I)$$

wherein:

m is 0 or 1;

Q is hydrogen or cyclopropyl;

Alk is an unsubstituted $C_1$-$C_6$ alkyl;

X is —C(=O)$NR_6$—, or —C(=O)O— wherein $R_6$ is hydrogen, optionally substituted $C_1$-$C_6$ alkyl, $C_2$-$C_6$ alkenyl or $C_2$-$C_6$ alkynyl;

$Z_1$ is —N= or —CH=

$Z_2$ is —N= or —C($R_1$)=;

$R_1$ is hydrogen, methyl, ethyl, ethenyl, ethynyl, methoxy, mercapto, mercaptomethyl, halo, fully or partially fluorinated ($C_1$-$C_2$)alkyl, ($C_1$-$C_2$)alkoxy or ($C_1$-$C_2$)alkylthio, nitro, or nitrile (—CN);

$R_2$ is a group $Q^1$-$[Alk^1]_q$-$Q^2$-, wherein q is 0 or 1;

$Alk^1$ is an optionally substituted, divalent, straight chain or branched $C_1$-$C_6$ alkylene, or $C_2$-$C_6$ alkenylene or $C_2$-$C_6$ alkynylene radical which may contain or terminate in an ether (—O—), thioether (—S—) or amino (—NR)— link;

$Q^2$ is an optionally substituted divalent monocyclic carbocyclic or heterocyclic radical having 5 or 6 ring atoms or an optionally substituted divalent bicyclic carbocyclic or heterocyclic radical having 9 or 10 ring atoms;

$Q^1$ is hydrogen, an optional substituent, or an optionally substituted carbocyclic or heterocyclic radical having 3-7 ring atoms.

2. A compound as claimed in claim 1 wherein $Z_1$ is —CH=.

3. A compound as claimed in claim 1 wherein $Z_2$ is —CH=.

4. A compound as claimed in claim 1 wherein $Z_2$ is —CF=.

5. A compound as claimed in claim 1 wherein $Z_1$ and $Z_2$ are both —CH=.

6. A compound as claimed in claim 1 wherein $Z_1$ is —CH= and $Z_2$ is —CF=.

7. A compound as claimed in claim 1 wherein m is 1 and Q is hydrogen.

8. A compound as claimed in claim 1 wherein X is —C(O)NH—.

9. A compound as claimed in claim 1 wherein m is 1, Q is hydrogen, Alk is —$CH_2CH_2$—, and X is —C(O)NH—.

10. A compound as claimed in claim 1 wherein, in the substituent $R_2$ of the said compound, $Q^2$ is an optionally substituted pyridine, pyrimidine, pyrazine, pyran-2-one, pyrimidine-4-one or pyridine-2-one ring.

11. A compound as claimed in claim 1 wherein, in the substituent $R_2$ of the said compound, $Q^2$ is an optionally substituted pyridine-3-yl ring, an optionally substituted pyrimidine-5-yl ring, an optionally substituted pyrazine-2-yl ring, an optionally substituted pyran-2-one-4-yl ring or an optionally substituted pyridine-2-one-4-yl ring.

12. A compound as claimed in claim 1 wherein, in the substituent $R_2$ of the said compound, $Alk^1$ is present and is an optionally substituted divalent $C_1$-$C_3$ alkylene radical.

13. A compound as claimed in claim 1 wherein, in the substituent $R_2$ of the said compound, $Q^1$ is a group of formula —$NR^AR^B$, wherein $R^A$ and $R^B$ are independently hydrogen or a ($C_1$-$C_6$)alkyl, hydroxy($C_1$-$C_6$)alkyl, or ($C_1$-$C_3$)alkoxy($C_1$-$C_3$)alkyl group.

14. A compound as claimed in claim 1 wherein, in the substituent $R_2$ of the said compound, $Q^1$ is a group of formula —$NR^AR^B$, wherein $R^A$ and $R^B$ taken together with that nitrogen form a cyclic amino ring.

15. A compound as claimed in claim 1 wherein the cyclic amino ring is a morpholinyl, piperidinyl, or piperazinyl ring.

16. A compound as claimed in claim 1 wherein, in the substituent $R_2$ of the said compound, $Q^2$ is an optionally substituted pyridinyl, pyrimidinyl or pyrazinyl radical, q is 0 and $Q^1$ is an optionally substituted heterocyclic radical having 3-7 ring atoms.

17. A compound as claimed in claim 16 wherein $Q^1$ is an optionally substituted oxadiazolyl or tetrazolyl radical.

18. A compound as claimed in claim 16 wherein $Q^1$ is an optionally substituted piperidinyl or pyrrolidinyl radical.

19. A compound as claimed in claim 18 wherein $Q^1$ is substituted by —COOH.

20. A compound as claimed in claim 1 wherein, in the substituent $R_2$ of the said compound, $Q^2$ is an optionally substituted pyrimidine-4-one or pyridine-2-one, q is 1 and $Q^1$ is an optionally substituted heterocyclic radical having 3-7 ring atoms.

21. A compound as claimed in claim 20 wherein, $Alk^1$ is —$CH_2$— and $Q^1$ is an optionally substituted pyridinyl radical.

22. A compound as claimed in claim 1 selected from the group consisting of:
1-ethyl-3-(5-pyridin-3-yl-benzothiazol-2-yl)-urea
2-{5-[2-(3-ethyl-ureido)-benzothiazol-5-yl]-pyridin-2-yl}-N-methyl-acetamide
1-ethyl-3-[5-(1-methyl-2-oxo-1,2-dihydro-pyridin-4-yl)-benzothiazol-2-yl]-urea
1-ethyl-3-(6-fluoro-5-pyridin-3-yl-benzothiazol-2-yl)-urea
1-(5-([1,2,4]triazolo[4,3-a]pyridin-6-yl)benzo[d]thiazol-2-yl)-3-ethylurea
1-ethyl-3-(5-(imidazo[1,2-a]pyridin-6-yl)benzo[d]thiazol-2-yl)urea
1-ethyl-3-(5-(tetrazolo[1,5-a]pyridin-6-yl)benzo[d]thiazol-2-yl)urea
1-(5-(3,4-dihydro-2H-pyrido[3,2-b][1,4]oxazin-7-yl)benzo[d]thiazol-2-yl)-3-ethylurea
1-ethyl-3-(5-(6-(hydroxymethyl)pyridin-3-yl)benzo[d]thiazol-2-yl)urea
1-ethyl-3-(5-(5-(2-oxopyridin-1(2H)-yl)pyrazin-2-yl)benzo[d]thiazol-2-yl)urea
1-ethyl-3-(5-(2-(hydroxymethyl)-1-methyl-1H-imidazol-5-yl)benzo[d]thiazol-2-yl)urea
1-ethyl-2-(5-(2-(3-ethylureido)benzo[d]thiazol-5-yl)-2-oxopyridin-1(2H)-yl)acetate
1-(5-(1-(2-ethoxyethyl)-6-oxo-1,6-dihydropyridin-3-yl)benzo[d]thiazol-2-yl)-3-ethylurea
1-ethyl-3-(5-(6-methyl-2-oxo-2H-pyran-4-yl)benzo[d]thiazol-2-yl)urea
methyl 5-(2-(3-ethylureido)benzo[d]thiazol-5-yl)picolinate
1-ethyl-3-(5-(1-(2-morpholinoethyl)-1H-pyrazol-4-yl)benzo[d]thiazol-2-yl)urea
1-(5-(1H-pyrazol-3-yl)benzo[d]thiazol-2-yl)-3-ethylurea
1-ethyl-3-(5-(1-methyl-1H-pyrazol-4-yl)benzo[d]thiazol-2-yl)urea
1-ethyl-3-(5-(4-methyl-3,4-dihydro-2H-pyrido[3,2-b][1,4]oxazin-7-yl)benzo[d]thiazol-2-yl)urea
1-ethyl-3-(5-(isoquinolin-4-yl)benzo[d]thiazol-2-yl)urea
1-(5-(1H-pyrazol-4-yl)benzo[d]thiazol-2-yl)-3-ethylurea
1-ethyl-3-(5-(2-methoxythiazol-5-yl)benzo[d]thiazol-2-yl)urea
1-ethyl-3-(5-(2-hydroxythiazol-5-yl)benzo[d]thiazol-2-yl)urea
1-ethyl-3-(5-(imidazo[1,2-a]pyridin-3-yl)benzo[d]thiazol-2-yl)urea
1-(5-([1,2,4]triazolo[1,5-a]pyridin-6-yl)benzo[d]thiazol-2-yl)-3-ethylurea
N-(5-(2-(3-ethylureido)benzo[d]thiazol-5-yl)pyridin-2-yl)acetamide
1-ethyl-3-(5-(6-morpholinopyridin-3-yl)benzo[d]thiazol-2-yl)urea
1-(5-(2-(1H-imidazol-1-yl)pyrimidin-5-yl)benzo[d]thiazol-2-yl)-3-ethylurea
1-ethyl-3-(5-(2-oxo-1,2-dihydropyridin-4-yl)benzo[d]thiazol-2-yl)urea
1-ethyl-3-(5-(6-(2-methyl-2H-tetrazol-5-yl)pyridin-3-yl)benzo[d]thiazol-2-yl)urea
1-ethyl-3-(5-(1-(2-methoxyethyl)-6-methyl-2-oxo-1,2-dihydropyridin-4-yl)benzo[d]thiazol-2-yl)urea
1-ethyl-3-(5-(1-(2-hydroxyethyl)-6-methyl-2-oxo-1,2-dihydropyridin-4-yl)benzo[d]thiazol-2-yl)urea
1-ethyl-3-(5-(6-methyl-1-((6-methylpyridin-2-yl)methyl)-2-oxo-1,2-dihydropyridin-4-yl)benzo[d]thiazol-2-yl)urea
1-ethyl-3-(5-(6-methyl-2-oxo-1-(pyridin-3-ylmethyl)-1,2-dihydropyridin-4-yl)benzo[d]thiazol-2-yl)urea
1-ethyl-3-(5-(6-methyl-2-oxo-1-(pyridin-2-ylmethyl)-1,2-dihydropyridin-4-yl)benzo[d]thiazol-2-yl)urea
1-ethyl-3-(5-(6-methyl-2-oxo-1-(1-(pyridin-2-yl)ethyl)-1,2-dihydropyridin-4-yl)benzo[d]thiazol-2-yl)urea
ethyl 7-(2-(3-ethylureido)benzo[d]thiazol-5-yl)-1-methyl-4-oxo-1,4-dihydroquinoline-3-carboxylate
N-(5-(2-(3-ethylureido)-6-fluorobenzo[d]thiazol-5-yl)pyridin-2-yl)acetamide
ethyl 2-(4-(2-(3-ethylureido)-6-fluorobenzo[d]thiazol-5-yl)-1H-pyrazol-1-yl)acetate
1-ethyl-3-(6-fluoro-5-(6-methyl-2-oxo-2H-pyran-4-yl)benzo[d]thiazol-2-yl)urea
1-ethyl-3-(6-fluoro-5-(2-(4-(2-hydroxyethyl)piperazin-1-yl)pyrimidin-5-yl)benzo[d]thiazol-2-yl)urea
1-ethyl-3-(6-fluoro-5-(2-(piperazin-1-yl)pyrimidin-5-yl)benzo[d]thiazol-2-yl)urea hydrochloride salt
methyl 1-(5-(2-(3-ethylureido)-6-fluorobenzo[d]thiazol-5-yl)pyrimidin-2-yl)piperidine-4-carboxylate
1-(5-(2-(3-ethylureido)-6-fluorobenzo[d]thiazol-5-yl)pyrimidin-2-yl)piperidine-4-carboxylic acid
methyl 1-(5-(2-(3-ethylureido)-6-fluorobenzo[d]thiazol-5-yl)pyrimidin-2-yl)piperidine-3-carboxylate 1-(5-(2-(3-ethylureido)-6-fluorobenzo[d]thiazol-5-yl)pyrimidin-2-yl)piperidine-3-carboxylic acid methyl 2-(4-(2-(3-ethylureido)-6-fluorobenzo[d]thiazol-5-yl)-1H-pyrazol-1-yl)propanoate 1-ethyl-3-(6-fluoro-5-(1H-pyrrolo[2,3-b]pyridin-3-yl)benzo[d]thiazol-2-yl)urea 1-ethyl-3-(6-fluoro-5-(6-methyl-2-oxo-1-(pyridin-3-ylmethyl)-1,2-dihydropyridin-4-yl)benzo[d]thiazol-2-yl)urea 1-ethyl-3-(6-fluoro-5-(6-methyl-1-((1-methylpyrrolidin-3-yl)methyl)-2-oxo-1,2-dihydropyridin-4-yl)benzo[d]thiazol-2-yl)urea 1-ethyl-3-(6-fluoro-5-(6-methyl-1-((1-methylpiperidin-2-yl)methyl)-2-oxo-1,2-dihydropyridin-4-yl)benzo[d]thiazol-2-yl)urea 1-ethyl-3-(6-fluoro-5-(6-methyl-1-((1-methyl-1H-imidazol-4-yl)methyl)-2-oxo-1,2-dihydropyridin-4-yl)benzo[d]thiazol-2-yl)urea tert-butyl 2-((4-(2-(3-ethylureido)-6-fluorobenzo[d]thiazol-5-yl)-6-methyl-2-oxopyridin-1(2H)-yl)methyl)pyrrolidine-1-carboxylate 1-(5-(1-(3-(dimethylamino)propyl)-6-methyl-2-oxo-1,2-dihydropyridin-4-yl)-6-fluorobenzo[d]thiazol-2-yl)-3-ethylurea 1-ethyl-3-(6-fluoro-5-(6-(5-methyl-1,2,4-oxadiazol-3-yl)pyridin-3-yl)benzo[d]thiazol-2-yl)urea 1-ethyl-3-[6-fluoro-5-(4-methoxy-pyridin-2-yl)-benzothiazol-2-yl]-urea 1-ethyl-3-(6-fluoro-5-(2-(4-methylpiperazin-1-yl)pyrimidin-5-yl)benzo[d]thiazol-2-yl)urea 1-ethyl-3-(6-fluoro-5-(5-methoxypyridin-3-yl)benzo[d]thiazol-2-yl)urea 1-ethyl-3-(6-fluoro-5-(5-hydroxypyridin-3-yl)benzo[d]thiazol-2-yl)urea 5-(2-(3-ethylureido)-6-fluorobenzo[d]thiazol-5-yl)-N'-hydroxypicolinimidamide 1-ethyl-3-(6-fluoro-5-(1-methyl-2-oxo-1,2-dihydropyridin-4-yl)benzo[d]thiazol-2-yl)urea 1-ethyl-3-(6-fluoro-5-(1-(2-morpholinoethyl)-2-oxo-1,2-dihydropyridin-4-yl)benzo[d]thiazol-2-yl)urea 1-(5-(1-(2-(dimethylamino)ethyl)-2-oxo-1,2-dihydropyridin-4-yl)-6-fluorobenzo[d]thiazol-2-yl)-3-ethylurea tert-butyl 3-((4-(2-(3-ethylureido)-6-fluorobenzo[d]thiazol-5-yl)-2,2'-dioxo-2H-1,4'-bipyridin-1'(2'H)-yl)methyl)piperidine-1-carboxylate 1-ethyl-3-(6-fluoro-5-(6-(hydroxymethyl)pyridin-3-yl)benzo[d]thiazol-2-yl)urea 1-ethyl-3-(6-fluoro-5-(6-(morpholinomethyl)pyridin-3-yl)benzo[d]thiazol-2-yl)urea 1-ethyl-3-(6-fluoro-5-(2-oxo-1-(pyrrolidin-3-yl)-1,2-dihydropyridin-4-yl)benzo[d]thiazol-2-yl)urea 2-{5-[2-(3-ethyl-ureido)-6-fluoro-benzothiazol-5-yl]-pyridin-2-yl}-N-methyl-acetamide 1-ethyl-3-(6-fluoro-5-(thiazol-5-yl)benzo[d]thiazol-2-yl)urea 1-ethyl-3-(6-fluoro-5-(2-(methylsulfonyl)pyrimidin-5-yl)benzo[d]thiazol-2-yl)urea 1-ethyl-3-(6-methoxy-5-(pyridin-3-yl)benzo[d]thiazol-2-yl)urea 1-ethyl-3-(6-methoxy-5-(1-methyl-2-oxo-1,2-dihydropyridin-4-yl)benzo[d]thiazol-2-yl)urea 1-ethyl-3-(6-methyl-5-(pyridin-3-yl)benzo[d]thiazol-2-yl)urea 1-ethyl-3-(6-methyl-5-(1-methyl-2-oxo-1,2-dihydropyridin-4-yl)benzo[d]thiazol-2-yl)urea 1-ethyl-3-(6-(pyridin-3-yl)thiazolo[5,4-b]pyridin-2-yl)urea N-(5-(2-(3-ethylureido)thiazolo[5,4-b]pyridin-6-yl)pyridin-2-yl)acetamide 1-ethyl-3-(6-(6-methyl-2-oxo-2H-pyran-4-yl)thiazolo[5,4-b]pyridin-2-yl)urea 1-Ethyl-3-(6-fluoro-5-{6-methyl-1-[1-(6-methyl-pyridin-3-yl)-ethyl]-2-oxo-1,2-dihydro-pyridin-4-yl}-benzothiazol-2-yl)-urea and 1-Ethyl-3-{6-fluoro-5-[1-(3-methoxy-pyridin-2-ylmethyl)-2-oxo-1,2-dihydro-pyridin-4-yl]-benzothiazol-2-yl}-urea.

23. An antibacterial composition comprising a compound as claimed in claim 1, together with one or more pharmaceutically acceptable carriers and/or excipients.

* * * * *